US009321840B2

(12) United States Patent
Burkly et al.

(10) Patent No.: US 9,321,840 B2
(45) Date of Patent: Apr. 26, 2016

(54) BINDING PROTEINS, INCLUDING ANTIBODIES, ANTIBODY DERIVATIVES AND ANTIBODY FRAGMENTS, THAT SPECIFICALLY BIND CD154 AND USES THEREOF

(71) Applicants: UCB PHARMA S.A., Brussels (BE); BIOGEN IDEC MA INC., Cambridge, MA (US)

(72) Inventors: Linda C. Burkly, West Newton, MA (US); Janine L. Ferrant-Orgettas, Gloucester, MA (US); Ellen A. Garber, Cambridge, MA (US); Yen-Ming Hsu, Lexington, MA (US); Lihe Su, Reading, MA (US); Frederick R. Taylor, Milton, MA (US); Ralph Adams, Berkshire (GB); Derek Thomas Brown, Berkshire (GB); Andrew George Popplewell, Berkshire (GB); Martyn Kim Robinson, Berkshire (GB); Anthony Shock, Berkshire (GB); Kerry Louise Tyson, Berkshire (GB)

(73) Assignees: UCB BIOPHARMA SPRL, Brussels (BE); BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/309,118

(22) Filed: Jun. 19, 2014

(65) Prior Publication Data
US 2014/0302016 A1  Oct. 9, 2014

Related U.S. Application Data

(60) Division of application No. 13/656,922, filed on Oct. 22, 2012, now Pat. No. 8,784,823, which is a continuation of application No. 12/532,517, filed as application No. PCT/US2008/003735 on Mar. 21, 2008, now Pat. No. 8,293,237.

(60) Provisional application No. 60/920,495, filed on Mar. 27, 2007, provisional application No. 60/919,938, filed on Mar. 22, 2007, provisional application No. 60/919,816, filed on Mar. 22, 2007.

(51) Int. Cl.
*C07K 16/28* (2006.01)
*A61K 39/00* (2006.01)

(52) U.S. Cl.
CPC ....... *C07K 16/2875* (2013.01); *A61K 2039/505* (2013.01); *C07K 2317/24* (2013.01); *C07K 2317/55* (2013.01); *C07K 2317/71* (2013.01); *C07K 2317/92* (2013.01)

(58) Field of Classification Search
CPC ........... C07K 16/2875; C07K 2317/24; C07K 2317/55; A61K 2039/505
USPC ........ 424/172.1; 530/387.3, 389.1; 536/23.53
See application file for complete search history.

(56) References Cited

U.S. PATENT DOCUMENTS

| 8,293,237 | B2 | 10/2012 | Burkly et al. |
| 8,784,823 | B2 | 7/2014 | Burkly et al. |
| 2014/0141468 | A1* | 5/2014 | Ellis et al. ................... 435/69.6 |

FOREIGN PATENT DOCUMENTS

| EA | 007905 | 2/2007 |
| WO | WO 01/68860 | 9/2001 |
| WO | WO 02/18445 | 3/2002 |
| WO | WO 02/18446 | 3/2002 |
| WO | WO 03/031475 | 4/2003 |
| WO | WO 03/48306 | 6/2003 |
| WO | WO 2004/003019 | 1/2004 |
| WO | WO 2004/051268 | 6/2004 |
| WO | WO 2004/072116 | 8/2004 |
| WO | WO 2005/003175 | 1/2005 |
| WO | WO 2005/011376 | 2/2005 |
| WO | WO 2005/035572 | 4/2005 |
| WO | WO 2006/030220 | 3/2006 |
| WO | WO 2006/033702 | 3/2006 |
| WO | WO-2008/118356 | 10/2008 |

OTHER PUBLICATIONS

Casset, F. et al. "A peptide mimetic of an anti-CD4 monoclonal antibody by rational design" *Biochemical and Biophysical Research Communications*, 2003, pp. 198-205, vol. 307.
Smith-Gill, S. J. et al. "Contributions of Immunoglobulin Heavy and Light Chains to Antibody Specificity for Lysozyme and Two Haptens" *Journal of Immunology*, Dec. 15, 1987, pp. 4135-4144, vol. 139.
Song, M.-K. et al. "Light Chain of Natural Antibody Plays a Dominant Role in Protein Antigen Binding" *Biochemical and Biophysical Research Communications*, 2000, pp. 390-394, vol. 268.
Chen, Y. et al. "Selection and Analysis of an Optimized Anti-VEGF Antibody: Crystal Structure of an Affinity-matured Fab in Complex with Antigen" *J. Mol. Biol.*, 1999, pp. 865-881, vol. 293.
Ward, E. et al. "Binding activities of a repertoire of single immunoglobulin variable domains secreted from *Escherichia coli*" *Nature*, Oct. 12, 1989, pp. 544-546, vol. 341.
Kobayashi, H. et al. "Tryptophan H33 plays an important role in pyrimidine (6-4) pyrimidone photoproduct binding by a high-affinity antibody" *Protein Engineering*, 1999, pp. 879-884, vol. 12, No. 10.

(Continued)

*Primary Examiner* — Lynn Bristol
(74) *Attorney, Agent, or Firm* — Saliwanchik, Lloyd & Eisenchenk

(57) ABSTRACT

This invention provides binding proteins, including antibodies, antibody derivatives and antibody fragments, that specifically bind a CD154 (CD40L) protein. This invention also provides a chimeric, humanized or fully human antibody, antibody derivative or antibody fragment that specifically binds to an epitope to which a humanized Fab fragment comprising a variable heavy chain sequence according to SEQ ID NO: 1 and comprising a variable light chain sequence according to SEQ ID NO: 2 specifically binds. CD154 binding proteins of this invention may elicit reduced effector function relative to a second anti-CD154 antibody. CD154 binding proteins of this invention are useful in diagnostic and therapeutic methods, such as in the treatment and prevention of diseases including those that involve undesirable immune responses that are mediated by CD154-CD40 interactions.

15 Claims, 37 Drawing Sheets

(56) References Cited

OTHER PUBLICATIONS

Kumar, S. et al. "Molecular Cloning and Expression of the Fabs of Human Autoantibodies in Escherichia coli" *Journal of Biological Chemistry*, Nov. 10, 2000, pp. 35129-35136, vol. 275, No. 45.

MacCallum, R. M. et al. "Antibody-antigen Interactions: Contact Analysis and Binding Site Topography" *J. Mol. Biol.*, 1998, pp. 732-745, vol. 262.

Vajdos, F. F. et al. "Comprehensive Functional Maps of the Antigen-binding Site of an Anti-ErbB2 Antibody Obtained with Shotgun Scanning Mutagenesis" *J. Mol. Biol.*, 2002, pp. 415-428, vol. 320.

Colman, P. M. "Effects of amino acid sequence changes on antibody-antigen interactions" *Research in Immunology*, 1994, pp. 33-36, vol. 145.

Holm, P. et al. "Functional mapping and single chain construction of the anti-cytokeratin 8 monoclonal antibody TS1" *Molecular Immunology*, 2007, pp. 1075-1084, vol. 44.

Jang, Y.-J. et al. "The structural basis for DNA binding by an anti-DNA autoantibody" *Molecular Immunology*, 1998, pp. 1207-1217, vol. 35.

Wu, H. et al. "Humanization of a Murine Monoclonal Antibody by Simultaneous Optimization of Framework and CDR Residues" *J. Mol. Biol.*, 1999, pp. 151-162, vol. 294.

De Pascalis, R. et al. "Grafting of "Abbreviated" Complementarity-Determining Regions Containing Specificity-Determining Residues Essential for Ligand Contact to Engineer a Less Immunogenic Humanized Monoclonal Antibody" *Journal of Immunology*, 2002, pp. 3076-3084, vol. 169.

Burks, E. A. et al. "In vitro scanning saturation mutagenesis of an antibody binding pocket" *Proc. Natl. Acad. Sci. USA*, Jan. 1997, pp. 412-417, vol. 94.

Brummell, D. A. et al. "Probing the combining site of an anti-carbohydrate antibody by saturation-mutagenesis: role of the heavy-chain CDR3 residues" *Biochemistry*, Feb. 2, 1993, pp. 1180-1187, vol. 32, No. 4.

Brorson, K. et al. "Mutational Analysis of Avidity and Fine Specificity of Anti-Levan Antibodies" *Journal of Immunology*, 1999, pp. 6694-6701, vol. 163.

Rudikoff, S. et al. "Single amino acid substitution altering antigen-binding specificity" *Proc. Natl. Acad. Sci. USA*, Mar. 1982, pp. 1979-1983, vol. 79.

Brams, P. et al. "A humanized anti-human CD154 monoclonal antibody blocks CD154-CD40 mediated human B cell activation" *International Immunopharmacology*, 2001, pp. 277-294, vol. 1.

Boumpas, D.T. et al. "A Short Course of BG9588 (Anti-CD40 Ligand Antibody) Improves Serologic Activity and Decreases Hematuria in Patients With Proliferative Lupus Glomerulonephritis" *Arthritis & Rheumatism*, Mar. 2003, vol. 48, No. 3, pp. 719-727.

Durie, F.H. et al. "Prevention of Collagen-Induced Arthritis with an Antibody to gp39, the Ligand for CD40" *Science*, Sep. 3, 1993, vol. 261, pp. 1328-1330.

Ferrant, J.L. et al. "The contribution of Fc effector mechanisms in the efficacy of anti-CD154 immunotherapy depends on the nature of the immune challenge" *International Immunology*, Oct. 5, 2004, vol. 16, No. 11, pp. 1583-1594.

Kuwana, M. et al. "Effect of a single injection of humanized anti-CD154 monoclonal antibody on the platelet-specific autoimmune response in patients with immune thrombocytopenic purpura" *Blood*, Feb. 15, 2004, vol. 103, No. 4, pp. 1229-1236.

Quezada, S.A. et al. "Distinct Mechanisms of Action of Anti-CD154 in Early Versus Late Treatment of Murine Lupus Nephritis" *Arthritis & Rheumatism*, Sep. 2003, vol. 48, No. 9, pp. 2541-2554.

Kalled, S. L. et al. "Apoptosis and Altered Dendritic Cell Homeostasis in Lupus Nephritis Are Limited by Anti-CD154 Treatment" *The Journal of Immunology*, 2001, pp. 1740-1747, vol. 167.

Cordeiro, A. C. et al. "Novel Therapies in Lupus—Focus on Nephritis" *Acta Reumatol Port.* 2008, pp. 157-169, vol. 33, No. 2.

Toubi, E. et al. "The Role of CD40-CD 154 Interactions in Autoimmunity and the Benefit of Disrupting this Pathway" *Immunity*, 2004, pp. 457-464, vol. 37, Nos. 6-7. Abstract Only.

Peters, A. et al. "CD40 and Autoimmunity: The Dark Side of a Great Activator" *Semin Immunol.*, Oct. 2009, pp. 293-300, vol. 21, No. 5.

* cited by examiner

FIGURE 1

CDR sequences for anti-CD154 antibody 342

| Sequence ID Number | Description | Sequence |
|---|---|---|
| SEQ ID NO: 3 | CDR-H1 | GFSSTNYHVH |
| SEQ ID NO: 4 | CDR-H2 | VIWGDGDTSYNSVLKS |
| SEQ ID NO: 5 | CDR-H3 | QLTHYYVLAA |
| SEQ ID NO: 6 | CDR-L1 | RASEDLYYNLA |
| SEQ ID NO: 7 | CDR-L2 | DTYRLAD |
| SEQ ID NO: 8 | CDR-L3 | QQYYKFPFT |

CDR sequences for anti-CD154 antibody 381

| Sequence ID Number | Description | Sequence |
|---|---|---|
| SEQ ID NO: 42 | CDR-H1 | GFTFSDYYMA |
| SEQ ID NO: 43 | CDR-H2 | SISYEGSSTYYGDSVKG |
| SEQ ID NO: 44 | CDR-H3 | HDDSPGYYFDY |
| SEQ ID NO: 45 | CDR-L1 | LAGEDISNVLA |
| SEQ ID NO: 46 | CDR-L2 | AANRLQD |
| SEQ ID NO: 47 | CDR-L3 | QQTFRYPLT |

CDR sequences for anti-CD154 antibody 338

| Sequence ID Number | Description | Sequence |
|---|---|---|
| SEQ ID NO: 48 | CDR-H1 | GFSLTSHHIS |
| SEQ ID NO: 49 | CDR-H2 | VMWNDGGTLYNSALKS |
| SEQ ID NO: 50 | CDR-H3 | GKMHYYVLDA |
| SEQ ID NO: 51 | CDR-L1 | RTSEDIYSNLA |
| SEQ ID NO: 52 | CDR-L2 | DTNRLAD |
| SEQ ID NO: 53 | CDR-L3 | QHYSNFPWT |

FIGURE 2

Rat anti-CD154 342 antibody sequences

| Sequence ID Number | Description | Sequence |
|---|---|---|
| SEQ ID NO: 29 (heavy 342 in Figure 9) | RAT 342 Ab VH region | QVQLKESGPGLVQPSETLSLTCTVSGFSSTNYHVHWVRQPPG KSLEWMGVIWGDGDTSYNSVLKSRLSITRDTSRSQVFLKMSS LQTEDTATYYCARQLTHYYVLAAWGQGASVTVS |
| SEQ ID NO: 34 | RAT 342 Ab VH region with signal sequence | atggctgtcctggtgctgttgctctgcctgatgacatttcca agctgtgtcctgtcccaggtgcagctgaaggagtcaggacct ggcctggtgcagccctcagagaccctgtctctcacctgcact gtctctggttctcatcaaccaattatcatgtgcactgggtt cgacagcctccaggaaaaagtcttgagtggatgggagtaata tggggtgatggagacacatcatataattcagttctcaaatcc cgactgagcatcaccagggacacctccaggagccaagttttc ttaaaaatgagcagtctgcaaacggaggacactgccacctac tattgtgccaggcaattgactcattactatgttctggctgcc tggggtcaaggagcttcagtcactgtctcg |
| SEQ ID NO: 32 | RAT 342 Ab VH region without signal sequence | caggtgcagctgaaggagtcaggacctggcctggtgcagccc tcagagaccctgtctctcacctgcactgtctctggttctca tcaaccaattatcatgtgcactgggttcgacagcctccagga aaaagtcttgagtggatgggagtaatatggggtgatggagac acatcatataattcagttctcaaatcccgactgagcatcacc agggacacctccaggagccaagttttcttaaaaatgagcagt ctgcaaacggaggacactgccacctactattgtgccaggcaa ttgactcattactatgttctggctgcctggggtcaaggagct tcagtcactgtctcg |
| SEQ ID NO: 30 (light 342 in Figure 9) | RAT 342 Ab VL region | DIQMTQSPASLSASLGETVTVECRASEDLYYNLAWYQRKPGN SPQLLIYDTYRLADGVPSRFSGSGSGTQYSLKINTLPSGDVA SYFCQQYYKFPFTFGSGTKLELK |
| SEQ ID NO: 33 | RAT 342 Ab VL region with signal sequence | atgggtgtgcccactcatctcctggggttgttgctactgtgg attacagatgccatatgtgacatccagatgacacagtctcca gcttccctgtctgcatctctgggagaaactgtcaccgtcgaa tgtcgagcaagtgaggacctttactataatttagcgtggtat cagcggaaaccagggaactctcctcaactcctgatctatgat acatataggttggcagatggggtcccatcacggttcagtggc agtgggtctggcacacagtattctctaaagataaacaccctg ccatctggagatgtcgcaagttatttctgtcaacagtattac aaatttccattcacgttcggctcagggaccaagctggaactg aaa |
| SEQ ID NO: 31 | RAT 342 Ab VL region without signal sequence | gacatccagatgacacagtctccagcttccctgtctgcatct ctgggagaaactgtcaccgtcgaatgtcgagcaagtgaggac ctttactataatttagcgtggtatcagcggaaaccagggaac tctcctcaactcctgatctatgatacatataggttggcagat ggggtcccatcacggttcagtggcagtgggtctggcacacag tattctctaaagataaacaccctgccatctggagatgtcgca agttatttctgtcaacagtattacaaatttccattcacgttc ggctcagggaccaagctggaactgaaa |

FIGURE 3

Acceptor Framework Sequences

| Sequence ID Number | Description | Sequence |
|---|---|---|
| SEQ ID NO: 35 (2 1 1 O12 in Figure 9) | Human VK1 2-1-(1) O12 JK1 acceptor framework | DIQMTQSPSSLSASVGDRVTITCRASQSISSYLNWYQ QKPGKAPKLLIYAASSLQSGVPSRFSGSGSGTDFTLT ISSLQPEDFATYYCQQSYSTPWTFGQGTKVEIK |
| SEQ ID NO: 36 | Human VK1 2-1-(1) O12 JK1 acceptor framework | gacatccagatgacccagtctccatcctccctgt ctgcatctgtaggagacagagtcaccatcacttg ccgggcaagtcagagcattagcagctatttaaat tggtatcagcagaaaccagggaaagcccctaagc tcctgatctatgctgcatccagtttgcaaagtgg ggtcccatcaaggttcagtggcagtggatctggg acagatttcactctcaccatcagcagtctgcaac ctgaagatttgcaacttactactgtcaacagag ttacagtacccttggacgttcggccaagggacc aaggtggaaatcaaa |
| SEQ ID NO: 37 (1-1 3-66 in Figure 9) | Human VH3 1-1 3-66 JH4 acceptor framework | EVQLVESGGGLVQPGGSLRLSCAASGFTVSSNYMSWV RQAPGKGLEWVSVIYSGGSTYYADSVKGRFTISRDNS KNTLYLQMNSLRAEDTAVYYCARYFDYWGQGTLVTVS |
| SEQ ID NO: 38 | Human VH3 1-1 3-66 JH4 acceptor framework | gaggtgcagctggtggagtctgggggaggcttgg tccagcctggggggtccctgagactctcctgtgc agcctctggattcaccgtcagtagcaactacatg agctgggtccgccaggctccagggaaggggctgg agtgggtctcagttatttatagcggtggtagcac atactacgcagactccgtgaagggcagattcacc atctccagagacaattccaagaacacgctgtatc ttcaaatgaacagcctgagagccgaggacacggc tgtgtattactgtgcgagatactttgactactgg ggccagggaaccctggtcaccgtctcc |
| SEQ ID NO: 39 (1-1 4-59 in Figure 9) | Human VH4 1-1 4-59 JH4 acceptor framework | QVQLQESGPGLVKPSETLSLTCTVSGGSISSYYWSWI RQPPGKGLEWIGYIYYSGSTNYNPSLKSRVTISVDTS KNQFSLKLSSVTAADTAVYYCARYFDYWGQGTLVTVS |
| SEQ ID NO: 40 | Human VH4 1-1 4-59 JH4 acceptor framework | caggtgcagctgcaggagtcgggcccaggactgg tgaagccttcggagaccctgtccctcacctgcac tgtctctggtggctccatcagtagttactactgg agctggatccggcagcccccagggaagggactgg agtggattgggtatatctattacagtgggagcac caactacaacccctccctcaagagtcgagtcacc atatcagtagacacgtccaagaaccagttctccc tgaagctgagctctgtgaccgctgcggacacggc cgtgtattactgtgcgagatactttgactactgg ggccagggaaccctggtcaccgtctcc |

FIGURE 4

342 CDR grafts based on acceptor frameworks

| Sequence ID Number | Description | Sequence |
|---|---|---|
| SEQ ID NO: 10 (VH3 gH7 in Figure 9) | Variable heavy CDR-only graft based on VH3 1-1 3-66 JH4 acceptor framework | EVQLVESGGGLVQPGGSLRLSCAASGFSSTNYHVHWVRQA PGKGLEWVSVIWGDGDTSYNSVLKSRFTISRDNSKNTLYL QMNSLRAEDTAVYYCARQLTHYYVLAAWGQGTLVTVS |
| SEQ ID NO: 20 | Variable heavy CDR-only graft based on VH3 1-1 3-66 JH4 acceptor framework | gaggtgcagctggtcgagtctggaggcgggcttgtccagc ctggtgggagcctgcgtctctcttgtgcagcgagcggctt cagctctaccaattaccatgtgcactgggtgcgtcaggca cctgggaagggcctggagtgggtgagtgttatttggggcg acggcgatacatcctacaactccgtcctgaagagccgttt caccatttccgtgacaactcaaagaatacccttacctc cagatgaactctctccgcgcagaggacacagcagtctatt actgtgcacgtcaactgacccactattacgttttggcagc ctggggtcaagggactctggtcacagtctcg |
| SEQ ID NO: 9 | Variable heavy CDR-only graft based on VH4 1-1 4-59 JH4 acceptor framework | QVQLQESGPGLVKPSETLSLTCTVSGFSSTNYHVHWI RQPPGKGLEWIGVIWGDGDTSYNSVLKSRVTISVDTS KNQFSLKLSSVTAADTAVYYCARQLTHYYVLAAWGQG TLVTVS |
| SEQ ID NO: 19 | Variable heavy CDR-only graft based on VH4 1-1 4-59 JH4 acceptor framework | caggtgcagctgcaggagtctggaccgggcttgtca agcctagtgagaccctgagcctcacttgtaccgtgag cggcttcagctctaccaattaccatgtgcactggatt cgtcagccacctgggaagggcctggagtggattggtg ttatttggggcgacggcgatacatcctacaactccgt cctgaagagccgtgtcaccatttccgttgacacctca aagaatcaattttccctcaagttgagctctgtcaccg cagcggacacagcagtctattactgtgcacgtcaact gacccactattacgttttggcagcctggggtcaaggg actctggtcacagtctcg |
| SEQ ID NO: 14 (VK1 gL3 in Figure 9) | Variable light CDR-only graft based on VK1 2-1-(1) O12 JK1 acceptor framework | DIQMTQSPSSLSASVGDRVTITCRASEDLYYNLAWYQ QKPGKAPKLLIYDTYRLADGVPSRFSGSGSGTDFTLT ISSLQPEDFATYYCQQYYKFPFTFGQGTKVEIK |
| SEQ ID NO: 16 | Variable light CDR-only graft based on VK1 2-1-(1) O12 JK1 acceptor framework | gatatccagatgacccagagtccaagcagtctctccg ccagcgtaggcgatcgtgtgactattacctgtcgtgc cagtgaggacctctattacaacctggcctggtatcag caaaaacgggcaaagccccgaagctgctcatctatg atacgtaccgctggctgacggtgtgccaagccgttt cagtggcagtggcagcggtactgactttaccctcaca atttcgtctctccagccggaagatttcgccacttact attgtcagcaatattacaagttccctttcaccttcgg tcagggcactaaagtagaaatcaaa |

FIGURE 5

342 gH1 based on acceptor frameworks

| Sequence ID Number | Description | Sequence |
|---|---|---|
| SEQ ID NO: 1 (VH3 gH1 in Figure 9) | gH1 based on VH3 1-1 3-66 JH4 acceptor framework | EVQLVESGGGLVQPGGSLRLSCAVSGFSSTNYHV HWVRQAPGKGLEWMGVIWGDGDTSYNSVLKSRFT ISRDTSKNTVYLQMNSLRAEDTAVYYCARQLTHY YVLAAWGQGTLVTVS |
| SEQ ID NO: 22 | gH1 based on VH3 1-1 3-66 JH4 acceptor framework | gaggtgcagctggtcgagtctggaggcggcttgtcc agcctggtgggagcctgcgtctctcttgtgcagtgag cggcttcagctctaccaattaccatgtgcactgggtg cgtcaggcacctgggaagggcctggagtggatgggtg ttatttggggcgacggcgatacatcctacaactccgt cctgaagagccgtttcaccatttcccgtgacacctca aagaataccgtttacctccagatgaactctctccgcg cagaggacacagcagtctattactgtgcacgtcaact gacccactattacgttttggcagcctggggtcaaggg actctggtcacagtctcg |
| SEQ ID NO: 11 (VH4 gH1 in Figure 9) | gH1 based on VH4 1-1 4-59 JH4 acceptor framework | QVQLQESGPGLVKPSETLSLTCTVSGFSSTNYHV HWIRQPPGKGLEWMGVIWGDGDTSYNSVLKSRVT ISRDTSKNQVSLKLSSVTAADTAVYYCARQLTHY YVLAAWGQGTLVTVS |
| SEQ ID NO: 21 | gH1 based on VH4 1-1 4-59 JH4 acceptor framework | caggtgcagctgcaggagtctggaccggggcttg tcaagcctagtgagaccctgagcctcacttgtac cgtgagcggcttcagctctaccaattaccatgtg cactggattcgtcagccacctgggaagggcctgg agtggatgggtgttatttggggcgacggcgatac atcctacaactccgtcctgaagagccgtgtcacc atttcccgtgacacctcaaagaatcaagtttccc tcaagttgagctctgtcaccgcagcggacacagc agtctattactgtgcacgtcaactgacccactat tacgttttggcagcctggggtcaagggactctgg tcacagtctcg |

| Sequence ID Number | Description | Sequence |
|---|---|---|
| SEQ ID NO: 2 (VK1 gL4 in Figure 9) | gL4 Variable light | DIQMTQSPSSLSASVGDRVTITCRASEDLYYNLA WYQRKPGKAPKLLIYDTYRLADGVPSRFSGSGSG TDYTLTISSLQPEDFASYYCQQYYKFPFTFGQGT KVEIK |
| SEQ ID NO: 17 | gL4 Variable light | gatatccagatgacccagagtccaagcagtctct ccgccagcgtaggcgatcgtgtgactattacctg tcgtgccagtgaggacctctattacaacctggcc tggtatcagcgtaaaccgggcaaagccccgaagc tgctcatctatgatacgtaccgcctggctgacgg tgtgccaagccgtttcagtggcagtggcagcggt actgactataccctcacaatttcgtctctccagc cggaagatttcgcctcttactattgtcagcaata ttacaagttccctttccacttcggtcagggcact aaagtagaaatcaaa |
| SEQ ID NO: 25 | gL4 Variable Light sequence with sequence encoding signal peptide underlined | <u>atgaaaaagacagctatcgcaattgcagtggcct tggctggtttcgctaccgtagcgcaagct</u>gatat ccagatgacccagagtccaagcagtctctccgcc agcgtaggcgatcgtgtgactattacctgtcgtg ccagtgaggacctctattacaacctggcctggta tcagcgtaaaccgggcaaagccccgaagctgctc atctatgatacgtaccgcctggctgacggtgtgc caagccgtttcagtggcagtggcagcggtactga ctataccctcacaatttcgtctctccagccggaa gatttcgcctcttactattgtcagcaatattaca agttccctttccacttcggtcagggcactaaagt agaaatcaaa |

FIGURE 7: 342 sequences

| Sequence ID Number | Description | Sequence |
|---|---|---|
| SEQ ID NO: 15 | 342gL4 light chain (including constant region) | DIQMTQSPSSLSASVGDRVTITCRASEDLYYNLAWYQRKPGKAPKLLIYDTYRLADGVPSRFSGSGSGTDYTLTISSLQPEDFASYYCQQYYKFPFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 18 | 342gL4 light chain (including constant region) | atgaaaaagacagctatcgcaattgcagtggccttggctggtttcgctaccgtagcgcaagctgatatccagatgacccagagtccaagcagtctctccgccagcgtaggcgatcgtgtgactattacctgtcgtgccagtgaggacctctattacaacctggctggtatcagcgtaaaccgggcaaagcccgaagctgctcatctatgatacgtaccgcctggctgacggtgtgccaagccgtttcagtggcagtggcagcggtactgactataccctcacaattcgtctctccagccggaagatttcgcctcttactattgtcagcaatattacaagttcccttttcaccttcggtcagggcactaaagtagaaatcaaacgtacggtagcggcccccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgagctcaccagtaacaaaaagttttaatagaggggagtgt |
| SEQ ID NO: 12 | 342gH1 Fab (no hinge) heavy chain (including constant region) | EVQLVESGGGLVQPGGSLRLSCAVSGFSSTNYHVHWVRQAPGKGLEWMGVIWGDGDTSYNSVLKSRFTISRDTSKNTVYLQMNSLRAEDTAVYYCARQLTHYYVLAAWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

FIGURE 7 continued

| Sequence ID Number | Description | Sequence |
|---|---|---|
| SEQ ID NO: 26 (SEQ ID NO: 23 without signal sequence) | 342gH1 Fab (no hinge) heavy chain (including constant region) | atgaagaagactgctatagcaattgcagtggcgctag ctggtttcgccaccgtggcgcaagctgaggttcagct ggtcgagtctggaggcgggcttgtccagcctggtggg agcctgcgtctctcttgtgcagtgagcggcttcagct ctaccaattaccatgtgcactgggtgcgtcaggcacc tgggaagggcctggagtggatgggtgttatttggggc gacggcgatacatcctacaactccgtcctgaagagcc gtttcaccatttccgtgacacctcaaagaataccgt ttacctccagatgaactctctccgcgcagaggacaca gcagtctattactgtgcacgtcaactgacccactatt acgttttggcagcctgggtcaaggactctggtcac agtctcgagcgcttctacaaagggcccatcggtcttc cccctggcaccctcctccaagagcacctctggggca cagcggccctgggctgcctggtcaaggactacttccc cgaaccggtgacggtgtcgtggaactcaggcgccctg accagcggcgtgcacaccttcccggctgtcctacagt cctcaggactctactccctcagcagcgtggtgaccgt gccctccagcagcttgggcacccagacctacatctgc aacgtgaatcacaagcccagcaacaccaaggtcgaca gaaagttgagcccaaatcttgt |
| SEQ ID NO: 13 | 342gH1 Fab' heavy chain (including constant region) | EVQLVESGGGLVQPGGSLRLSCAVSGFSSTNYHV HWVRQAPGKGLEWMGVIWGDGDTSYNSVLKSRFT ISRDTSKNTVYLQMNSLRAEDTAVYYCARQLTHY YVLAAWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVN HKPSNTKVDKKVEPKSCDKTHTCAA |
| SEQ ID NO: 27 (SEQ ID NO: 24 without signal sequence) | 342gH1 Fab' heavy chain (including constant region) | atgaagaagactgctatagcaattgcagtggcgctag ctggtttcgccaccgtggcgcaagctgaggttcagct ggtcgagtctggaggcgggcttgtccagcctggtggg agcctgcgtctctcttgtgcagtgagcggcttcagct ctaccaattaccatgtgcactgggtgcgtcaggcacc tgggaagggcctggagtggatgggtgttatttggggc gacggcgatacatcctacaactccgtcctgaagagcc gtttcaccatttccgtgacacctcaaagaataccgt ttacctccagatgaactctctccgcgcagaggacaca gcagtctattactgtgcacgtcaactgacccactatt acgttttggcagcctgggtcaaggactctggtcac agtctcgagcgcttctacaaagggcccatcggtcttc cccctggcaccctcctccaagagcacctctggggca cagcggccctgggctgcctggtcaaggactacttccc cgaaccggtgacggtgtcgtggaactcaggcgccctg accagcggcgtgcacaccttcccggctgtcctacagt cctcaggactctactccctcagcagcgtggtgaccgt gccctccagcagcttgggcacccagacctacatctgc aacgtgaatcacaagcccagcaacaccaaggtcgaca gaaagttgagcccaaatcttgtgacaaaactcacac atgcgccgcg |

FIGURE 8

SEQ ID NO: 28: 342gL4gH1 Fab (no hinge) vector DNA sequence

```
   1  atgaaaaaga cagctatcgc aattgcagtg gccttggctg gtttcgctac
  51  cgtagcgcaa gctGATATCc agatgaccca gagtccaagc agtctctccg
 101  ccagcgtagg cgatcgtgtg actattacct gtcgtgccag tgaggacctc
 151  tattacaacc tggcctggta tcagcgtaaa ccgggcaaag ccccgaagct
 201  gctcatctat gatacgtacc gcctggctga cggtgtgcca agccgtttca
 251  gtggcagtgg cagcggtact gactatccc tcacaatttc gtctctccag
 301  ccggaagatt tcgcctctta ctattgtcag caatattaca agttccctt
 351  caccttcggt cagggcacta aagtagaaat caaaCGTACG gtagcggccc
 401  catctgtctt catcttcccg ccatctgatg agcagttgaa atctggaact
 451  gcctctgttg tgtgcctgct gaataacttc tatcccagag aggccaaagt
 501  acagtggaag gtggataacg ccctccaatc gggtaactcc caggagagtg
 551  tcacagagca ggacagcaag gacagcacct acagcctcag cagcaccctg
 601  acgctgagca aagcagacta cgagaaacac aaagtctacg cctgcgaagt
 651  cacccatcag ggcctgagct caccagtaac aaaaagtttt aatagagggg
 701  agtgttaaaa tgaagaagac tgctatagca attgcagtgg cgctagctgg
 751  tttcgccacc gtggcgcaag ctgaggttCA GCTGgtcgag tctggaggcg
 801  ggcttgtcca gcctggtggg agcctgcgtc tctcttgtgc agtgagcggc
 851  ttcagctcta ccaattacca tgtgcactgg gtgcgtcagg cacctgggaa
 901  gggcctggag tggatggtg ttatttgggg cgacggcgat acatcctaca
 951  actccgtcct gaagagccgt ttcaccattt cccgtgacac ctcaaagaat
1001  accgtttacc tccagatgaa ctctctccgc gcagaggaca gcagtctta
1051  ttactgtgca cgtcaactga cccactatta cgttttggca gctggggtc
1101  aagggactct ggtcacagtC TCGAGcgctt ctacaaaggg cccatcggtc
1151  ttcccctgg cacctcctc caagagcacc tctggggca gcggccct
1201  gggctgcctg gtcaaggact acttccga accggtgacg tgtcgtgga
1251  actcaggcgc cctgaccagc ggcgtgcaca cttcccggc tgtcctacag
1301  tcctcaggac tctactccct cagcagcgtg gtgaccgtgc cctccagcag
1351  cttgggcacc cagacctaca tctgcaacgt gaatcacaag cccagcaaca
1401  ccaaggtcga caagaaagtt gagcccaaat cttgttaa
```

FIGURE 8 continued

SEQ ID NO: 41: 342gL4gH1 Fab' vector DNA sequence

```
   1  atgaaaaaga cagctatcgc aattgcagtg gccttggctg gtttcgctac
  51  cgtagcgcaa gctGATATCc agatgaccca gagtccaagc agtctctccg
 101  ccagcgtagg cgatcgtgtg actattacct gtcgtgccag tgaggacctc
 151  tattacaacc tggcctggta tcagcgtaaa ccgggcaaag ccccgaagct
 201  gctcatctat gatacgtacc gcctggctga cggtgtgcca agccgtttca
 251  gtggcagtgg cagcggtact gactataccc tcacaatttc gtctctccag
 301  ccggaagatt tcgcctctta ctattgtcag caatattaca agttcccttt
 351  caccttcggt cagggcacta aagtagaaat caaaCGTACG gtagcggccc
 401  catctgtctt catcttcccg ccatctgatg agcagttgaa atctggaact
 451  gcctctgttg tgtgcctgct gaataacttc tatcccagag aggccaaagt
 501  acagtggaag gtggataacg ccctccaatc gggtaactcc caggagagtg
 551  tcacagagca ggacagcaag gacagcacct acagcctcag cagcaccctg
 601  acgctgagca aagcagacta cgagaaacac aaagtctacg cctgcgaagt
 651  cacccatcag ggcctgagct caccagtaac aaaaagtttt aatagagggg
 701  agtgttaaaa tgaagaagac tgctatagca attgcagtgg cgctagctgg
 751  tttcgccacc gtggcgcaag ctgaggttCA GCTGgtcgag tctggaggcg
 801  ggcttgtcca gcctggtggg agcctgcgtc tctcttgtgc agtgagcggc
 851  ttcagctcta ccaattacca tgtgcactgg gtcgtcagg cacctgggaa
 901  gggcctggag tggatgggtg ttatttgggg cgacggcgat acatcctaca
 951  actccgtcct gaagagccgt tcaccattt ccgtgacac ctcaaagaat
1001  accgtttacc tccagatgaa ctctctccgc gcagaggaca cagcagtcta
1051  ttactgtgca cgtcaactga cccactatta cgttttggca gcctggggtc
1101  aaggactct ggtcacagtC TCGAGcgctt ctacaaaggg cccatcggtc
1151  ttccccctgg caccctcctc aagagcacc tctgggggca gcggccct
1201  gggctgcctg gtcaaggact acttccccga accggtgacg gtgtcgtgga
1251  actcaggcgc cctgaccagc ggcgtgcaca ccttccggc tgtcctacag
1301  tcctcaggac tctactccct cagcagcgtg gtgaccgtgc cctccagcag
1351  cttgggcacc cagacctaca tctgcaacgt gaatcacaag cccagcaaca
1401  ccaaggtcga caagaaagtt gagcccaaat cttgtgacaa aactcacaca
1451  tgcgccgcg
```

FIGURE 9

```
LIGHT CHAIN Grafts 342
           1       5        10        15        20        25        30        35        40        45        50        55        60        65        70        75        80        85        90        95        100       105
Light 342  DIQMTQSPASLSASLGETVTVECRASEDLYNRLAWYQRKPGNSPQLLIYDTSRLADGVPSRFSGSGSGTQYSLKINTLPSGDVASYFCQQYNKFPFTFGSGTKLELK
2 1 1 012  DIQMTQSPSSLSASVGDRVTITCRASQSISSYLNWYQQKPGKAPKLLIYAASSLQSGVPSRFSGSGSGTDFTLTISSLQPEDFATYYCQQSYSTPWTFGQGTKVEIK
                                    ||  | ||   |    |||||       ||           |                         |      | |
VK1 gL3    DIQMTQSPSSLSASVGDRVTITCRASEDLYNRLAWYQQKPGKAPKLLIYDTSRLADGVPSRFSGSGSGTDFTLTISSLQPEDFATYYCQQYNKFPFTFGQGTKVEIK
VK1 gL4    DIQMTQSPSSLSASVGDRVTITCKASEDLIYNRLAWYQRKPGKAPKLLIYDTYRLADGVPSRFSGSGSGTDYTLTISSLQPEDFASYCQQYNKFPFTFGQGTKVEIK HEAVY CHAIN VH3 Grafts 342
           1       5        10        15        20        25        30        35        40        45        50        55        60        65        70        75        80 abc 85        90        95        105       110
Heavy 342  QVQLKESGPGLVQPSETLSLTCTVSGFSSTNYYVHWVRQPPGKSLEWMGVIWGGGDTSYNSVLKSRLSITRDTSRSQVFLKMSSLQTEDTATYYCARQLTHYYVLAAWGQGASVTVS
1-1 3-66   EVQLVESGGGLVQPGGSLRLSCAASGFTVSSNYMSWVRQAPGKGLEWVSVIYSGGSTYYADSVKGRFTISRDNSKNTLYLQMNSLRAEDTAVYYCAR       YFDYWGQGTLVTVS
                                                                                                                |||||||||||||
VH3 gH7    EVQLVESGGGLVQPGGSLRLSCAASGFSSTNYYVHWVRQAPGKGLEWVSVIWGGGDTSYNSVLKSRFTISRDNSKNTLYLQMNSLRAEDTAVYYCARQLTHYYVLAAWGQGTLVTVS
VH3 gH1    EVQLVESGGGLVQPGGSLRLSCAVSGFSSTNYYVHWVRQAPGKGLEWMGVIWGGGDTSYNSVLKSRFTISRDTSKNTVYLQMNSLRAEDTAVYYCARQLTHYYVLAAWGQGTLVTVS HEAVY CHAIN VH4 Grafts 342
           1       5        10        15        20        25        30        35        40        45        50        55        60        65        70        75        80 abc 85        90        95        105       110
Heavy 342  QVQLKESGPGLVQPSETLSLTCTVSGFSSTNYYVHWVRQPPGKSLEWMGVIWGGGDTSYNSVLKSRLSITRDTSRSQVFLKMSSLQTEDTATYYCARQLTHYYVLAAWGQGASVTVS
1-1 4-59   QVQLQESGPGLVKPSETLSLTCTVSGGSISSYYWSWIRQPPGKGLEWIGYIYYSGSTNYNPSLKSRVTISVDTSKNQFSLKLSSVTAADTAVYYCAR       YFDYWGQGTLVTVS
                                                                                                                |||||||||||||
VH4 gH6    EVQLQESGPGLVKPSETLSLTCTVSGFSSTNYYVHWIRQPPGKGLEWIGVIWGGGDTSYNSVLKSRVTISVDTSKNQFSLKLSSVTAADTAVYYCARQLTHYYVLAAWGQGTLVTVS
VH4 gH1    EVQLQESGPGLVKPSETLSLTCTVSGFSSTNYYVHWIRQPPGKGLEWMGVIWGGGDTSYNSVLKSRVTISRDTSKNQFSLRLSSVTAADTAVYYCARQLTHYYVLAAWGQGTLVTVS
```

FIGURE 10: Anti-CD154 antibody 381

V<sub>L</sub> Sequence

SEQ ID NO: 54 (underlined sequence is a CDR sequence)
DIQMTQSPTS LSASLGETVS IE<u>CLAGEDIS NVLAWYQQKS GGSPQLLIYA
ANRLQDGVPS</u> RFSGSGSGTR YSLKISGMRP EDEADYFCQ<u>Q TFRYPLTFGS</u>
GTKLELK SEQ ID NO: 55
GACATCCAGA TGACACAGTC TCCAACTTCC CTGTCTGCAT CTCTCGGAGA
AACTGTCTCC ATCGAATGTC TAGCAGGTGA AGACATTTCC AATGTTTTAG
CGTGGTATCA GCAGAAGTCA GGGGGGTCTC CTCAGCTCCT GATCTATGCT
GCAAATAGGT TACAAGACGG GGTCCCCTCA CGGTTCAGTG GCAGTGGATC
TGGCACACGG TATTCTCTCA AGATCAGTGG CATGCGACCT GAAGATGAAG
CAGATTATTT CTGTCAACAG ACTTTCAGGT ATCCGCTCAC GTTCGGTTCT
GGGACCAAGC TGGAATTGAA A

V<sub>H</sub> Sequence

SEQ ID NO: 56 (underlined sequence is a CDR sequence)
EVPLVESGGG LVQPGRSMKL S<u>CVASGFTFS DYYMA</u>WVRQA PKKGLEWVAS
<u>ISYEGSSTYY GDSVKGRFTV</u> SRDIAKSTLY LQMHSLKSED TAIYYCAR<u>HD
DSPGYYFDYW</u> GQGVMVTVS SEQ ID NO: 57
GAGGTGCCGC TGGTGGAGTC TGGGGGAGGC TTAGTGCAGC CTGGAAGGTC
CATGAAACTT TCCTGTGTAG CCTCAGGATT CACTTTCAGT GACTATTACA
TGGCCTGGGT CCGCCAGGCT CCAAAGAAGG GTCTGGAGTG GGTCGCATCC
ATTAGTTATG AGGGTAGTAG TACTTACTAT GGAGACTCCG TGAAGGGCCG
ATTCACTGTC TCCAGAGATA TTGCAAAAAG CACCCTATAC CTTCAAATGC
ACAGTCTGAA GTCTGAGGAT ACGGCCATTT ATTATTGTGC ACGACATGAC
GATAGTCCAG GATACTACTT TGATTATTGG GGCCAAGGAG TCATGGTCAC
AGTCTCG

FIGURE 11: Anti-CD154 antibody 338

$V_L$ Sequence

SEQ ID NO: 58 (underlined sequence is a CDR sequence)
DIQMTQSPAS LSASLGETVT IECRTSEDIY SNLAWYRQRP GKSPQLLIYD
TNRLADGVPS RFSGSGSGTQ YSLKINSLQS EDVASYFCQH YSNFPWTFGG
DTKLELK SEQ ID NO: 59
GACATCCAGA TGACACAGTC TCCGGCTTCC CTGTCTGCAT CTCTGGGAGA
AACTGTCACC ATCGAATGTC GAACAAGTGA GGACATTTAC AGTAATTTAG
CGTGGTATCG GCAGAGACCA GGGAAGTCTC CTCAGCTCCT GATCTATGAT
ACAAATAGAT TGGCTGATGG GGTCCCGTCA CGGTTCAGTG GCAGTGGATC
TGGCACACAA TATTCTCTAA AGATAAACAG CCTGCAATCT GAAGATGTCG
CCAGCTATTT CTGTCAACAC TATAGCAATT TTCCGTGGAC CTTCGGTGGA
GACACCAAGC TGGAATTGAA A

$V_H$ Sequence

SEQ ID NO: 60 (underlined sequence is a CDR sequence)
QVQLTESGPG LVQPSQTLSL TCTVSGFSLT SHHISWVRQP PGKGLEWVGV
MWNDGGTLYN SALKSRPSIS RDTSKSQVFL KMSSLQTEDT ATYYCARGKM
HYYVLDAWGQ GASVTVS SEQ ID NO: 61
CAGGTGCAGC TGACGGAGTC AGGGCCTGGC CTGGTGCAGC CCTCACAGAC
CCTGTCTCTC ACCTGCACTG TCTCTGGGTT CTCATTAACC AGCCATCATA
TATCCTGGGT TCGACAGCCT CCAGGAAAAG GTCTGGAGTG GGTGGGAGTC
ATGTGGAATG ATGGAGGCAC ATTATATAAT TCAGCTCTCA AGTCTCGACC
GAGCATCAGT AGGGACACCT CCAAGAGTCA GGTCTTCTTA AAAATGAGCA
GTCTGCAAAC TGAAGACACA GCCACTTACT ACTGTGCCAG GGGCAAAATG
CATTACTATG TTCTGGATGC CTGGGGTCAA GGAGCTTCAG TCACTGTCTC
G

FIGURE 12
Anti-Human CD154 (CD40L) Antibodies
(Chimaeric Fab')

| Antibody | Kd Biacore (pM) | CD40 Binding IC50 (ng/ml) | ICAM-1 Upreg'n IC50 (ng/ml) |
|---|---|---|---|
| Hu5c8 (whole Ig) | 23 | 16 (n=6) | 43 (n=10) |
| CA081-00294 (294) | 107 | 26 (n=2) | 364 (n=6) |
| CA081-00295 (295) | 51 | 15 (n=2) | 138 (n=6) |
| CA081-00300 (300) | 43 | 15 (n=2) | 113 (n=7) |
| CA081-00335 (335) | 42 | - | 279 (n=3) |
| CA081-00303 (303) | 130 | 51 (n=3) | 252 (n=3) |
| CA081-00338 (338) | 15 | 6 (n=2) | 192 (n=6) |
| CA081-00342 (342) | 16 | 8 (n=5) | 53 (n=6) |
| CA081-00381 (381) | 5 | 22 (n=2) | 100 (n=2) |
| CA081-00402 (402) | 48 | 12 (n=2) | 92 (n=2) |

FIGURE 13: hu5c8 kappa light chain

SEQ ID NO: 62 (underlined sequence is the signal sequence)
<u>METDTLLLWV LLLWVPGSTG</u> DIVLTQSPAT LSVSPGERAT ISCRASQRVS
SSTYSYMHWY QQKPGQPPKL LIKYASNLES GVPARFSGSG SGTDFTLTIS
SVEPEDFATY YCQHSWEIPP TFGGGTKLEI KRTVAAPSVF IFPPSDEQLK
SGTASVVCLL NNFYPREAKV QWKVDNALQS GNSQESVTEQ DSKDSTYSLS
STLTLSKADY EKHKVYACEV THQGLSSPVT KSFNRGEC SEQ ID NO: 63 (mature protein)
DIVLTQSPAT LSVSPGERAT ISCRASQRVS SSTYSYMHWY QQKPGQPPKL
LIKYASNLES GVPARFSGSG SGTDFTLTIS SVEPEDFATY YCQHSWEIPP
TFGGGTKLEI KRTVAAPSVF IFPPSDEQLK SGTASVVCLL NNFYPREAKV
QWKVDNALQS GNSQESVTEQ DSKDSTYSLS STLTLSKADY EKHKVYACEV
THQGLSSPVT KSFNRGEC SEQ ID NO: 64 (open reading frame)
ATGGAGACAG ACACACTCCT GTTATGGGTG CTGCTGCTCT GGGTTCCAGG
TTCCACTGGT GACATTGTAC TGACACAGTC TCCTGCTACC TTATCTGTAT
CTCCGGGAGA GAGGGCCACC ATCTCATGCA GGGCCAGCCA ACGTGTCAGT
TCATCTACCT ATAGTTATAT GCACTGGTAC CAACAGAAAC CAGGACAGCC
ACCCAAACTC CTCATCAAGT ATGCATCCAA CCTAGAATCT GGGGTCCCTG
CCAGGTTCAG TGGCAGTGGG TCTGGGACTG ACTTCACCCT CACCATCTCT
TCTGTGGAGC CGGAGGATTT TGCAACATAT TACTGTCAGC ACAGTTGGGA
GATTCCTCCG ACGTTCGGTG AGGGACCAA GCTGGAGATC AAACGAACTG
TGGCTGCACC ATCTGTCTTC ATCTTCCCGC CATCTGATGA GCAGTTGAAA
TCTGGAACTG CCTCTGTTGT GTGCCTGCTG AATAACTTCT ATCCCAGAGA
GGCCAAAGTA CAGTGGAAGG TGGATAACGC CCTCCAATCG GGTAACTCCC
AGGAGAGTGT CACAGAGCAG GACAGCAAGG ACAGCACCTA CAGCCTCAGC
AGCACCCTGA CGCTGAGCAA AGCAGACTAC GAGAAACACA AAGTCTACGC
CTGCGAAGTC ACCCATCAGG GCCTGAGCTC GCCCGTCACA AAGAGCTTCA
ACAGGGGAGA GTGTTAG

FIGURE 14: hu5c8 aglyP-huIgG4 heavy chain

SEQ ID NO: 65 (underlined sequence is the signal sequence)
```
MDWTWRVFCL LAVAPGAHSQ VQLVQSGAEV VKPGASVKLS CKASGYIFTS
YYMYWVKQAP GQGLEWIGEI NPSNGDTNFN EKFKSKATLT VDKSASTAYM
ELSSLRSEDT AVYYCTRSDG RNDMDSWGQG TLVTVSSAST KGPSVFPLAP
CSRSTSESTA ALGCLVKDYF PEPVTVSWNS GALTSGVHTF PAVLQSSGLY
SLSSVVTVPS SSLGTKTYTC NVDHKPSNTK VDKRVESKYG PPCPPCPAPE
FLGGPSVFLF PPKPKDTLMI SRTPEVTCVV VDVSQEDPEV QFNWYVDGVE
VHNAKTKPRE EQFNSAYRVV SVLTVLHQDW LNGKEYKCKV SNKGLPSSIE
KTISKAKGQP REPQVYTLPP SQEEMTKNQV SLTCLVKGFY PSDIAVEWES
NGQPENNYKT TPPVLDSDGS FFLYSRLTVD KSRWQEGNVF SCSVMHEALH
NHYTQKSLSL SLG
```

SEQ ID NO: 66 (mature protein: S228P/T299A mutations are underlined and in bold)
```
QVQLVQSGAE VVKPGASVKL SCKASGYIFT SYYMYWVKQA PGQGLEWIGE
INPSNGDTNF NEKFKSKATL TVDKSASTAY MELSSLRSED TAVYYCTRSD
GRNDMDSWGQ GTLVTVSSAS TKGPSVFPLA PCSRSTSEST AALGCLVKDY
FPEPVTVSWN SGALTSGVHT FPAVLQSSGL YSLSSVVTVP SSSLGTKTYT
CNVDHKPSNT KVDKRVESKY GPPCPPCPAP EFLGGPSVFL FPPKPKDTLM
ISRTPEVTCV VVDVSQEDPE VQFNWYVDGV EVHNAKTKPR EEQFNSAYRV
VSVLTVLHQD WLNGKEYKCK VSNKGLPSSI EKTISKAKGQ PREPQVYTLP
PSQEEMTKNQ VSLTCLVKGF YPSDIAVEWE SNGQPENNYK TTPPVLDSDG
SFFLYSRLTV DKSRWQEGNV FSCSVMHEAL HNHYTQKSLS LSLG
```

SEQ ID NO: 67
```
ATGGACTGGA CCTGGAGGGT CTTCTGCTTG CTGGCTGTAG CACCAGGTGC
CCACTCCCAG GTCCAACTGG TGCAGTCAGG GGCTGAAGTG GTGAAGCCTG
GGCTTCAGT GAAGTTGTCC TGCAAGGCTT CTGGCTACAT CTTCACCAGT
TATTATATGT ACTGGGTGAA GCAGGCGCCC GGACAAGGCC TTGAGTGGAT
TGGAGAGATT AATCCTAGCA ATGGTGATAC TAACTTCAAT GAGAAGTTCA
AGAGTAAGGC CACACTGACT GTAGACAAAT CCGCCAGCAC AGCATACATG
GAGCTCAGCA GCCTGAGGTC TGAGGACACT GCGGTCTATT ACTGTACAAG
ATCGGACGGT AGAAATGATA TGGACTCCTG GGGCCAAGGG ACCCTGGTCA
CCGTCTCCTC AGCTTCCACC AAGGGCCCAT CCGTCTTCCC CCTGGCGCCC
TGCTCCAGAT CTACCTCCGA GAGCACAGCC GCCCTGGGCT GCCTGGTCAA
GGACTACTTC CCCGAACCGG TGACGGTGTC GTGGAACTCA GGCGCCCTGA
CCAGCGGCGT GCACACCTTC CCGGCTGTCC TACAGTCCTC AGGACTCTAC
TCCCTCAGCA GCGTGGTGAC CGTGCCCTCC AGCAGCTTGG CACGAAGAC
CTACACCTGC AACGTAGATC ACAAGCCCAG CAACACCAAG GTGGACAAGA
GAGTTGAGTC CAAATATGGT CCCCCATGCC CACCGTGCCC AGCACCTGAG
TTCCTGGGGG GACCATCAGT CTTCCTGTTC CCCCCAAAAC CCAAGGACAC
TCTCATGATC TCCCGGACCC CTGAGGTCAC GTGCGTGGTG GTGGACGTGA
GCCAGGAAGA CCCCGAGGTC CAGTTCAACT GGTACGTGGA TGGCGTGGAG
```

FIGURE 14 continued

```
GTGCATAATG CCAAGACAAA GCCGCGGGAG GAGCAGTTCA ACAGCGCGTA
CCGTGTGGTC AGCGTCCTCA CCGTCCTGCA CCAGGACTGG CTGAACGGCA
AGGAGTACAA GTGCAAGGTC TCCAACAAAG GCCTCCCGTC CTCCATCGAG
AAAACCATCT CCAAAGCCAA AGGGCAGCCC CGAGAGCCAC AAGTGTACAC
CCTGCCCCCA TCCCAGGAGG AGATGACCAA GAACCAGGTC AGCCTGACCT
GCCTGGTCAA AGGCTTCTAC CCCAGCGACA TCGCCGTGGA GTGGGAGAGC
AATGGGCAGC CGGAGAACAA CTACAAGACC ACGCCTCCCG TCCTCGATTC
CGACGGCTCC TTCTTCCTCT ACAGCAGGCT AACCGTGGAC AAGAGCAGGT
GGCAGGAGGG GAATGTCTTC TCATGCTCCG TGATGCATGA GGCTCTGCAC
AACCACTACA CACAGAAGAG CCTCTCCCTG TCTCTGGGTT GA
```

FIGURE 15: hu342 kappa light chain

SEQ ID NO: 68 (underlined sequence is the signal sequence)
<u>MDMRVPAQLL GLLLLWLRGA R</u>CDIQMTQSP SSLSASVGDR VTITCRASED
LYYNLAWYQR KPGKAPKLLI YDTYRLADGV PSRFSGSGSG TDYTLTISSL
QPEDFASYYC QQYYKFPFTF GQGTKVEIKR TVAAPSVFIF PPSDEQLKSG
TASVVCLLNN FYPREAKVQW KVDNALQSGN SQESVTEQDS KDSTYSLSST
LTLSKADYEK HKVYACEVTH QGLSSPVTKS FNRGEC SEQ ID NO: 69 (mature protein)
DIQMTQSPSS LSASVGDRVT ITCRASEDLY YNLAWYQRKP GKAPKLLIYD
TYRLADGVPS RFSGSGSGTD YTLTISSLQP EDFASYYCQQ YYKFPFTFGQ
GTKVEIKRTV AAPSVFIFPP SDEQLKSGTA SVVCLLNNFY PREAKVQWKV
DNALQSGNSQ ESVTEQDSKD STYSLSSTLT LSKADYEKHK VYACEVTHQG
LSSPVTKSFN RGEC SEQ ID NO: 70 (open reading frame)
ATGGACATGA GGGTCCCCGC TCAGCTCCTG GGGCTCCTGC TACTCTGGCT
CCGAGGTGCC AGATGTGATA TCCAGATGAC CCAGAGTCCA AGCAGTCTCT
CCGCCAGCGT AGGCGATCGT GTGACTATTA CCTGTCGTGC CAGTGAGGAC
CTCTATTACA ACCTGGCCTG GTATCAGCGT AAACCGGGCA AGCCCCGAA
GCTGCTCATC TATGATACGT ACCGCCTGGC TGACGGTGTG CCAAGCCGTT
TCAGTGGCAG TGGCAGCGGT ACTGACTATA CCCTCACAAT TTCGTCTCTC
CAGCCGGAAG ATTTCGCCTC TTACTATTGT CAGCAATATT ACAAGTTCCC
TTTCACCTTC GGTCAGGGCA CTAAAGTAGA AATCAAACGT ACGGTGGCTG
CACCATCTGT CTTCATCTTC CCGCCATCTG ATGAGCAGTT GAAATCTGGA
ACTGCCTCTG TTGTGTGCCT GCTGAATAAC TTCTATCCCA GAGAGGCCAA
AGTACAGTGG AAGGTGGATA ACGCCCTCCA ATCGGGTAAC TCCCAGGAGA
GTGTCACAGA GCAGGACAGC AAGGACAGCA CCTACAGCCT CAGCAGCACC
CTGACGCTGA GCAAAGCAGA CTACGAGAAA CACAAAGTCT ACGCCTGCGA
AGTCACCCAT CAGGGCCTGA GCTCGCCCGT CACAAAGAGC TTCAACAGGG
GAGAGTGTTA G

FIGURE 16: hu342 aglyP-huIgG4 heavy chain

SEQ ID NO: 71 (underlined sequence is the signal sequence)
MDWTWRVFCL LAVAPGAHSE VQLVESGGGL VQPGGSLRLS CAVSGFSSTN
YHVHWVRQAP GKGLEWMGVI WGDGDTSYNS VLKSRFTISR DTSKNTVYLQ
MNSLRAEDTA VYYCARQLTH YYVLAAWGQG TLVTVSSAST KGPSVFPLAP
CSRSTSESTA ALGCLVKDYF PEPVTVSWNS GALTSGVHTF PAVLQSSGLY
SLSSVVTVPS SSLGTKTYTC NVDHKPSNTK VDKRVESKYG PPCPPCPAPE
FLGGPSVFLF PPKPKDTLMI SRTPEVTCVV VDVSQEDPEV QFNWYVDGVE
VHNAKTKPRE EQFNSAYRVV SVLTVLHQDW LNGKEYKCKV SNKGLPSSIE
KTISKAKGQP REPQVYTLPP SQEEMTKNQV SLTCLVKGFY PSDIAVEWES
NGQPENNYKT TPPVLDSDGS FFLYSRLTVD KSRWQEGNVF SCSVMHEALH
NHYTQKSLSL SLG SEQ ID NO: 72 (mature protein: S228P/T299A mutations are underlined and in bold)
EVQLVESGGG LVQPGGSLRL SCAVSGFSST NYHVHWVRQA PGKGLEWMGV
IWGDGDTSYN SVLKSRFTIS RDTSKNTVYL QMNSLRAEDT AVYYCARQLT
HYYVLAAWGQ GTLVTVSSAS TKGPSVFPLA PCSRSTSEST AALGCLVKDY
FPEPVTVSWN SGALTSGVHT FPAVLQSSGL YSLSSVVTVP SSSLGTKTYT
CNVDHKPSNT KVDKRVESKY GPPCPPCPAP EFLGGPSVFL FPPKPKDTLM
ISRTPEVTCV VVDVSQEDPE VQFNWYVDGV EVHNAKTKPR EEQFNSAYRV
VSVLTVLHQD WLNGKEYKCK VSNKGLPSSI EKTISKAKGQ PREPQVYTLP
PSQEEMTKNQ VSLTCLVKGF YPSDIAVEWE SNGQPENNYK TTPPVLDSDG
SFFLYSRLTV DKSRWQEGNV FSCSVMHEAL HNHYTQKSLS LSLG SEQ ID NO: 73
ATGGACTGGA CCTGGAGGGT CTTCTGCTTG CTGGCTGTAG CACCAGGTGC
CCACTCCGAA GTACAATTGG TCGAGTCTGG AGGCGGGCTT GTCCAGCCTG
GTGGGAGCCT GCGTCTCTCT TGTGCAGTGA GCGGCTTCAG CTCTACCAAT
TACCATGTGC ACTGGGTGCG TCAGGCACCT GGGAAGGGCC TGGAGTGGAT
GGGTGTTATT TGGGGCGACG GCGATACATC CTACAACTCC GTCCTGAAGA
GCCGTTTCAC CATTTCCCGT GACACCTCAA AGAATACCGT TTACCTCCAG
ATGAACTCTC TCCGCGCAGA GGACACAGCA GTCTATTACT GTGCACGTCA
ACTGACCCAC TATTACGTTT TGGCAGCCTG GGGTCAAGGG ACTCTGGTCA
CAGTCTCGAG CGCTTCAACC AAGGGCCCAT CCGTCTTCCC CCTGGCGCCC
TGCTCCAGAT CTACCTCCGA GAGCACAGCC GCCCTGGGCT GCCTGGTCAA
GGACTACTTC CCCGAACCGG TGACGGTGTC GTGGAACTCA GGCGCCCTGA
CCAGCGGCGT GCACACCTTC CCGGCTGTCC TACAGTCCTC AGGACTCTAC
TCCCTCAGCA GCGTGGTGAC CGTGCCTCC AGCAGCTTGG GCACGAAGAC
CTACACCTGC AACGTAGATC ACAAGCCCAG CAACACCAAG GTGGACAAGA
GAGTTGAGTC CAAATATGGT CCCCCATGCC CACCGTGCCC AGCACCTGAG
TTCCTGGGGG GACCATCAGT CTTCCTGTTC CCCCCAAAAC CCAAGGACAC
TCTCATGATC TCCCGGACCC CTGAGGTCAC GTGCGTGGTG GTGGACGTGA

FIGURE 16 continued

```
GCCAGGAAGA CCCCGAGGTC CAGTTCAACT GGTACGTGGA TGGCGTGGAG
GTGCATAATG CCAAGACAAA GCCGCGGGAG GAGCAGTTCA ACAGCGCGTA
CCGTGTGGTC AGCGTCCTCA CCGTCCTGCA CCAGGACTGG CTGAACGGCA
AGGAGTACAA GTGCAAGGTC TCCAACAAAG GCCTCCCGTC CTCCATCGAG
AAAACCATCT CCAAAGCCAA AGGGCAGCCC CGAGAGCCAC AAGTGTACAC
CCTGCCCCCA TCCCAGGAGG AGATGACCAA GAACCAGGTC AGCCTGACCT
GCCTGGTCAA AGGCTTCTAC CCCAGCGACA TCGCCGTGGA GTGGGAGAGC
AATGGGCAGC CGGAGAACAA CTACAAGACC ACGCCTCCCG TCCTCGATTC
CGACGGCTCC TTCTTCCTCT ACAGCAGGCT AACCGTGGAC AAGAGCAGGT
GGCAGGAGGG GAATGTCTTC TCATGCTCCG TGATGCATGA GGCTCTGCAC
AACCACTACA CACAGAAGAG CCTCTCCCTG TCTCTGGGTT GA
```

FIGURE 18

Activity Profile of 342 Fab' & Fab'-PEG Entities

342 = gL4gH1 graft

|  | Kd Biacore (pM) | CD40 Binding IC50 (ng/ml) | ICAM-1 Upreg'n IC50 (ng/ml) | Competition Binding Assay IC50 (pM) |
|---|---|---|---|---|
| hu5c8 IgG1 | 25 | 31 | 37 | 54 |
| 342 Fab' | 28 | 12 | 40 | 24 |
| 342 Fab'-PEG | 50 | 35 | 127 | 113 |
| 342 Di-Fab' | nd | 9 | 22 | nd |
| 342 Di-Fab'-PEG | 45 | 32 | 58 | 26 |
| 342 Tri-Fab' | nd | 9 | 31 | nd |
| 342 Tri-Fab'-PEG | nd | 8 | 36 | nd |
| 342 aglycosyl IgG4 | nd | 25 | 48 | 35 |

FIGURE 19: Inhibition of IgG Immune Response to Tetanus Toxoid in Cynomolgus Monkeys
Primary Immune Response to TT
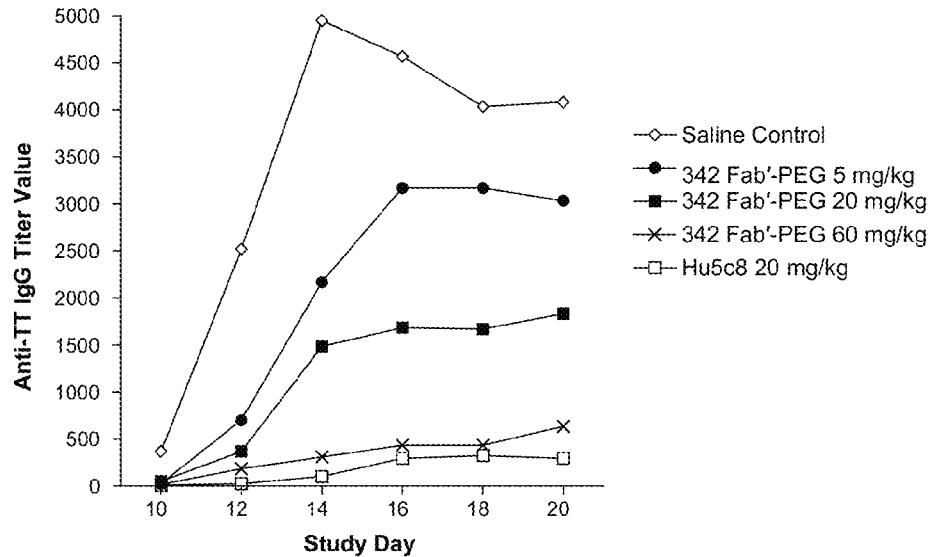
Immune Response to TT at Days 30-50
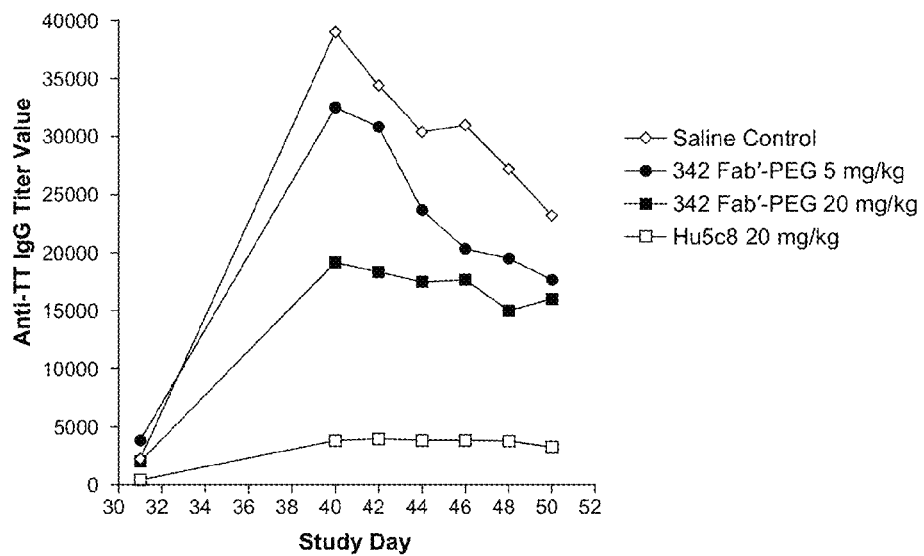

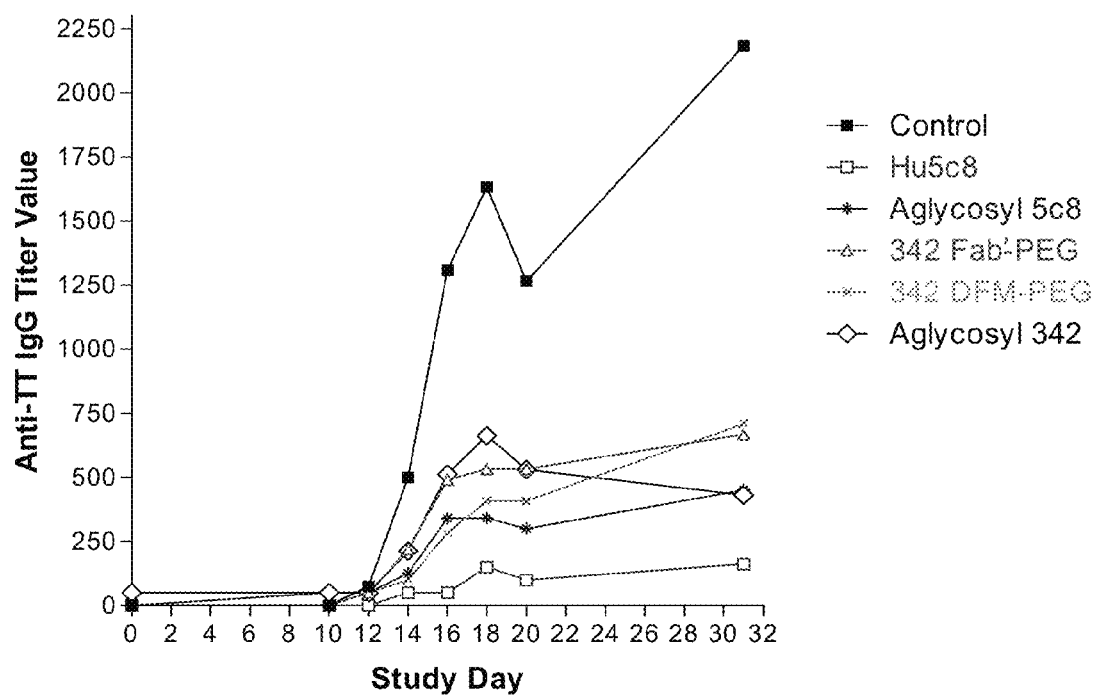
FIGURE 20: Inhibition of IgG Immune Response to Tetanus Toxoid in Cynomolgus Monkeys

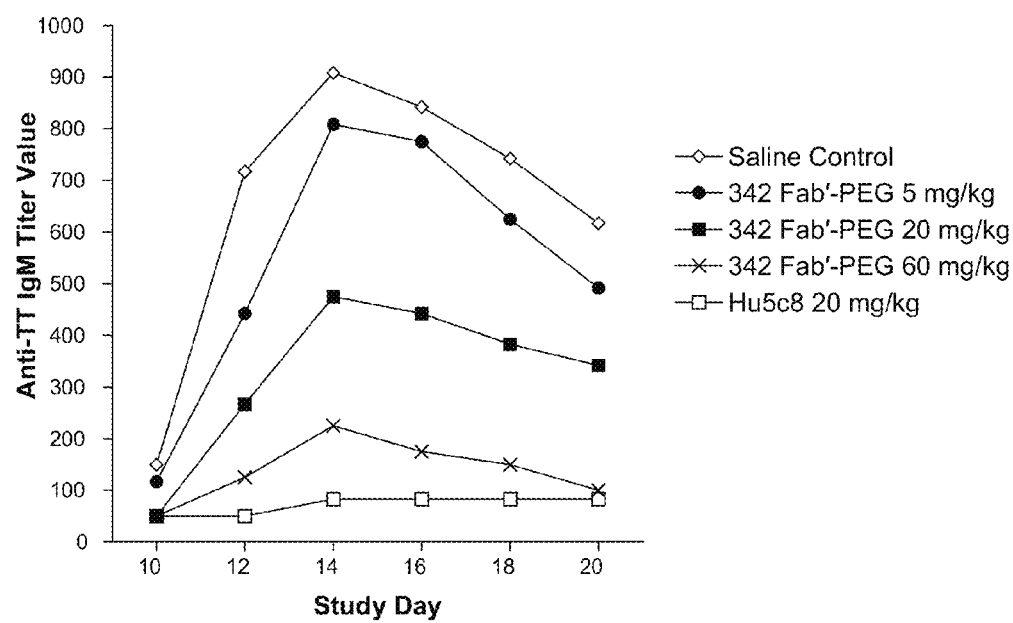
FIGURE 21: Primary IgM Immune Response to Tetanus Toxoid in Cynomolgus Monkeys

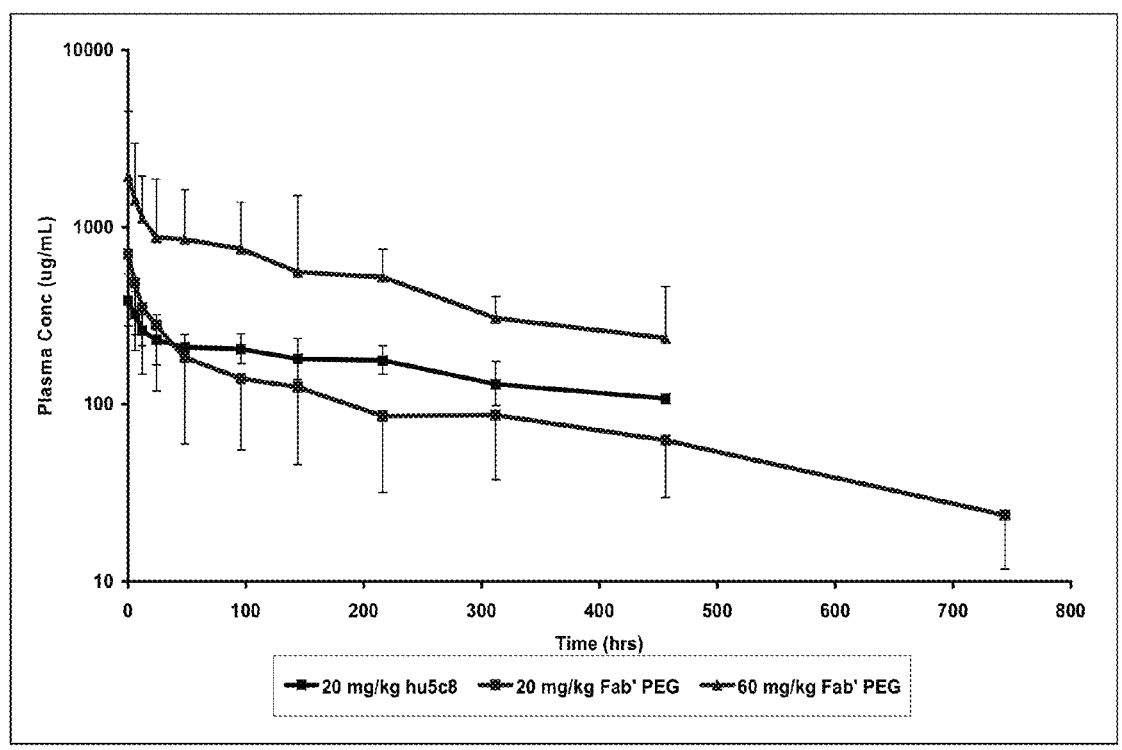
FIGURE 22: Pharmacokinetics of 342 Fab'-PEG in Cynomolgus Monkeys

FIGURE 25
A.
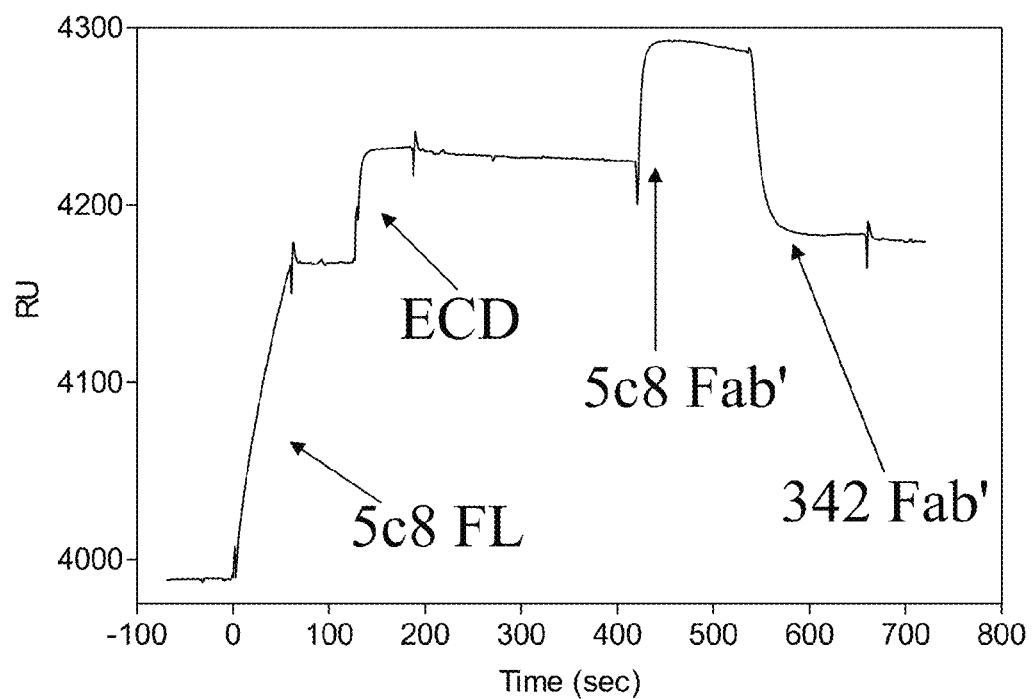
B.
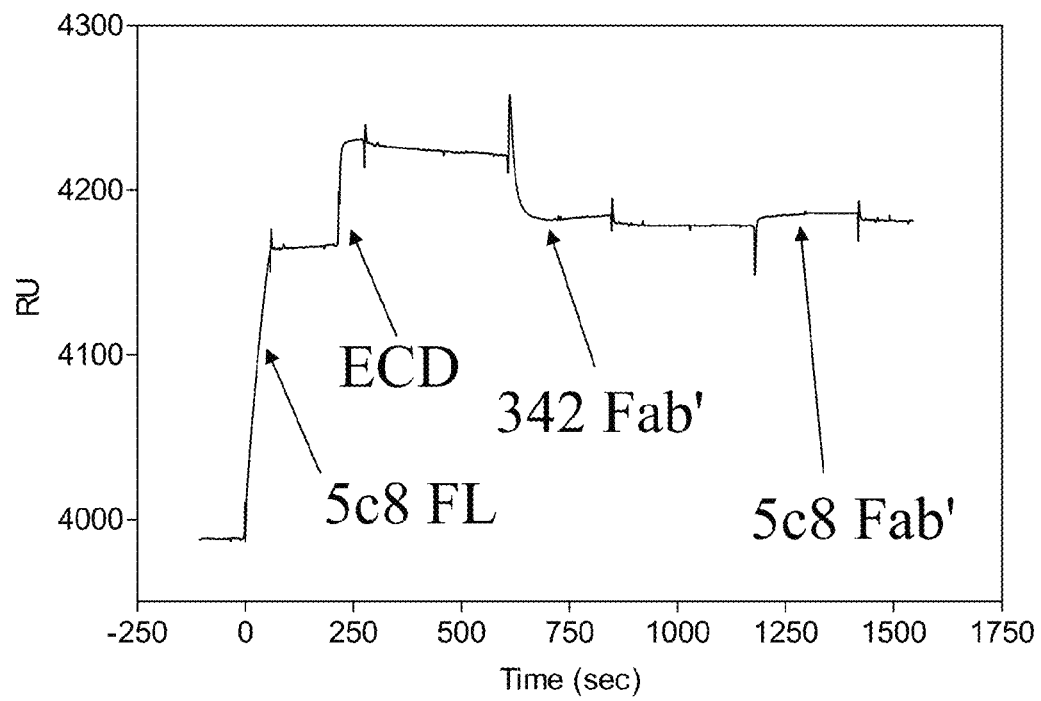

C.

FIGURE 25 continued
D.
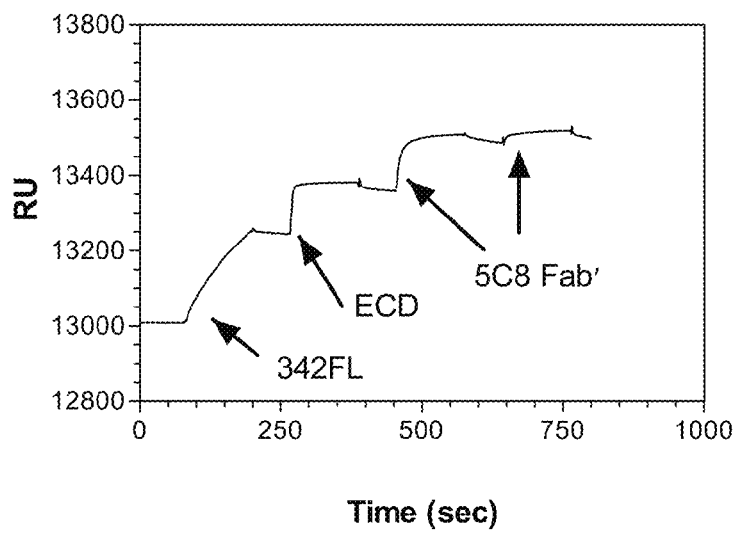
E.
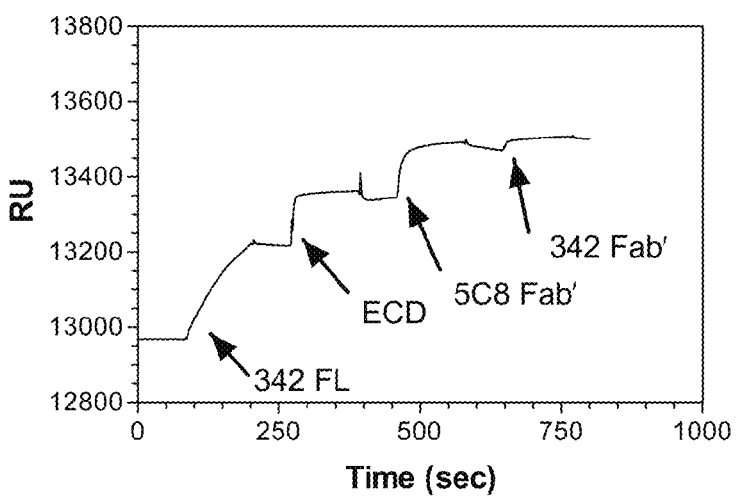
F.
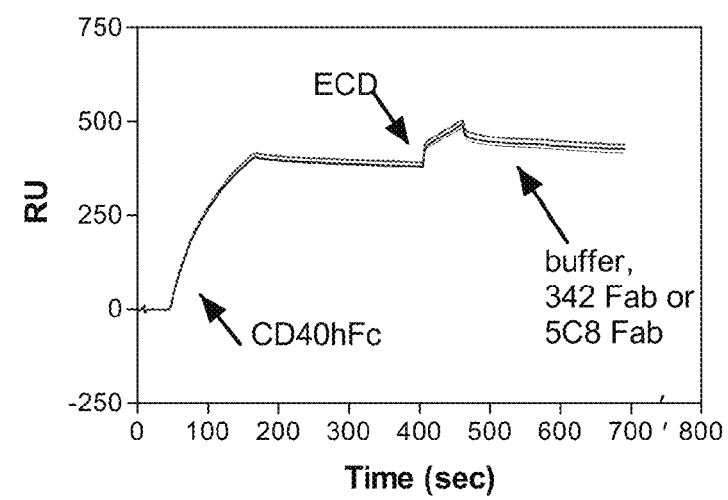

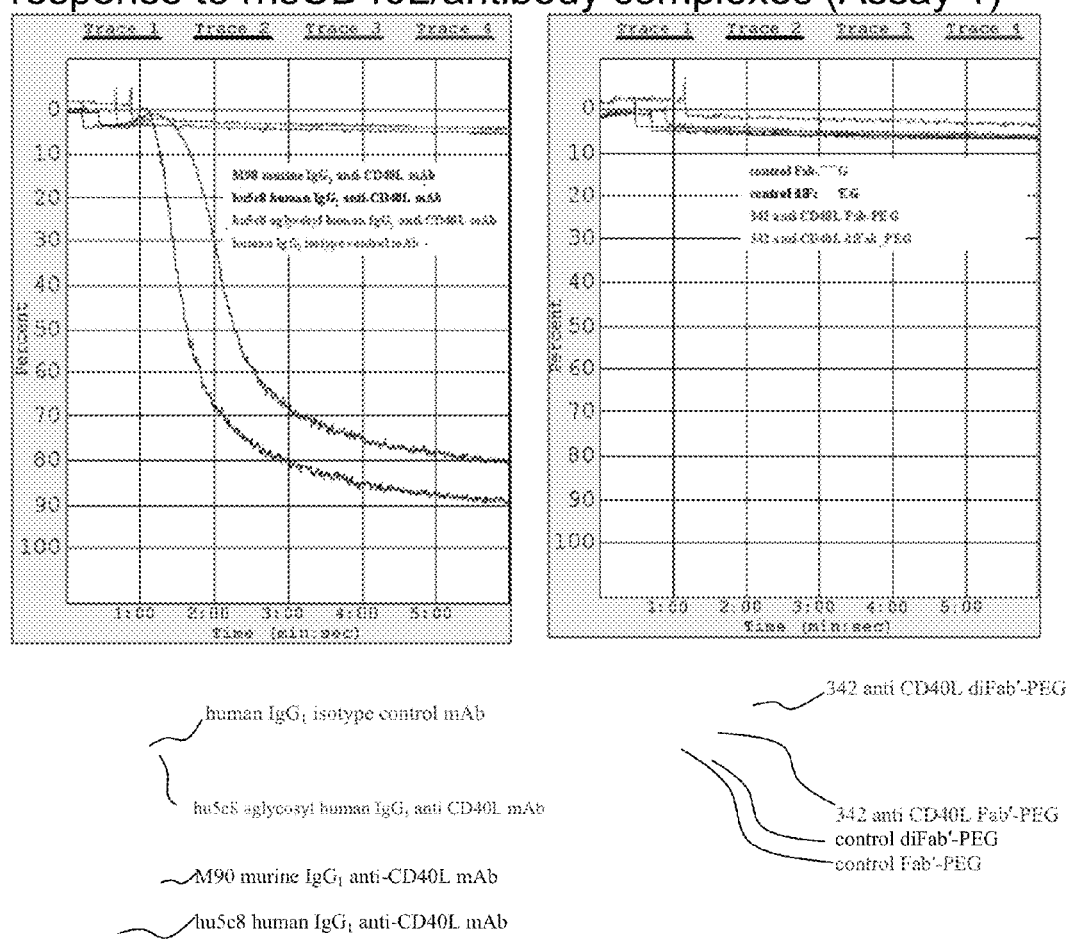
FIGURE 26: Representative platelet aggregation in response to rhsCD40L/antibody complexes (Assay 1)

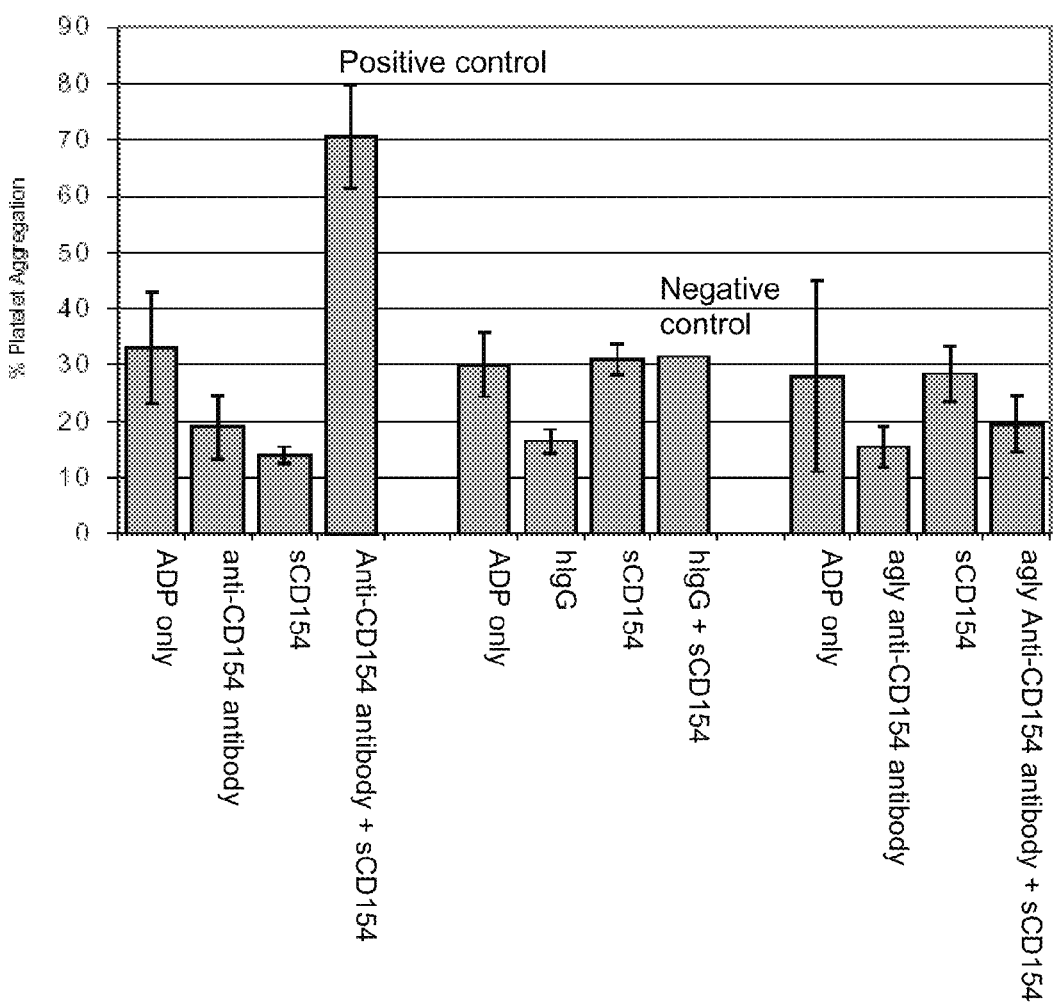
FIGURE 27: Representative platelet aggregation in response to control and anti-CD154 antibodies (Assay 2)

FIGURE 28

```
                            1           3                1
Human_Soluble_CD40L    GDQNPQIA AHVISEASSK TTSVLQWAEK GYYTMSNNLV TLENGKQLTV
Mouse_Soluble_CD40L    GDEDPQIA AHVVSEANSN AASVLQWAKK GYYTMKSNLV MLENGKQLTV 5    | |         2        6    |  6      5          6
Human_Soluble_CD40L    KRQGLYYIYA QVTFCSNREA SSQAPFIASL CLKSPGRFER ILLRAANTHS
Mouse_Soluble_CD40L    KREGLYYVYT QVTFCSNREP SSQRPFIVGL WLKPSSGSER ILLRAANTHS 2   |     5             3    4         |
Human_Soluble_CD40L    SARPCGQQSI HLGGVFELQP GASVFVNVTD PSQVSHGTGF TSFGLLKL
Mouse_Soluble_CD40L    SSQLCEQQSV HLGGVFELQA GASVFVNVTE ASQVIHRVGF SSFGLLKL
```

FIGURE 29
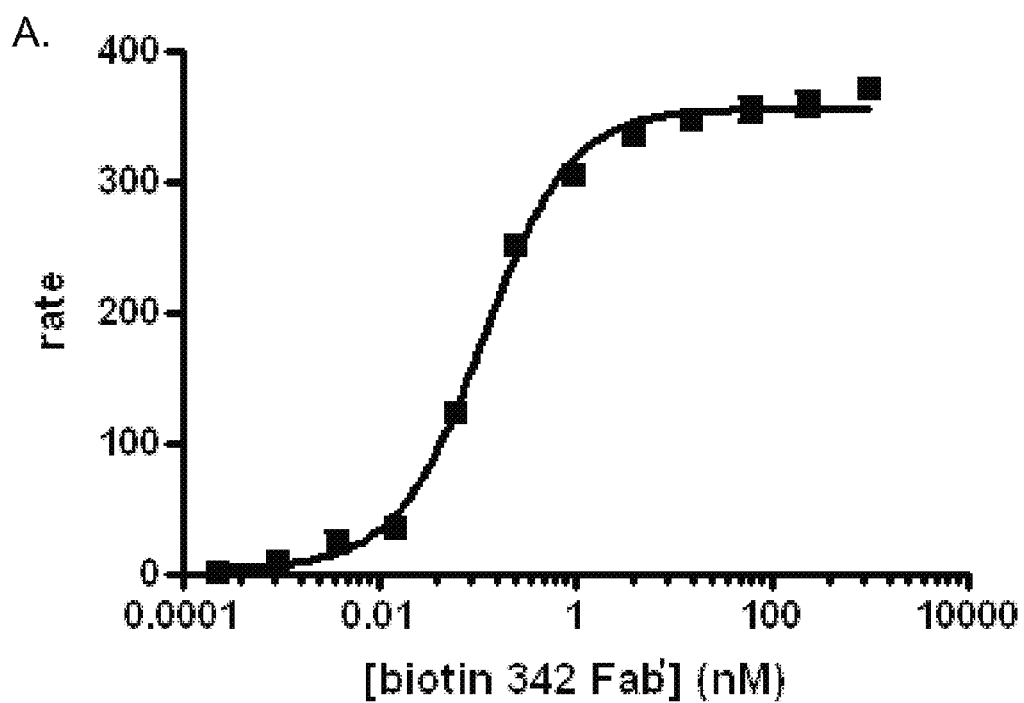
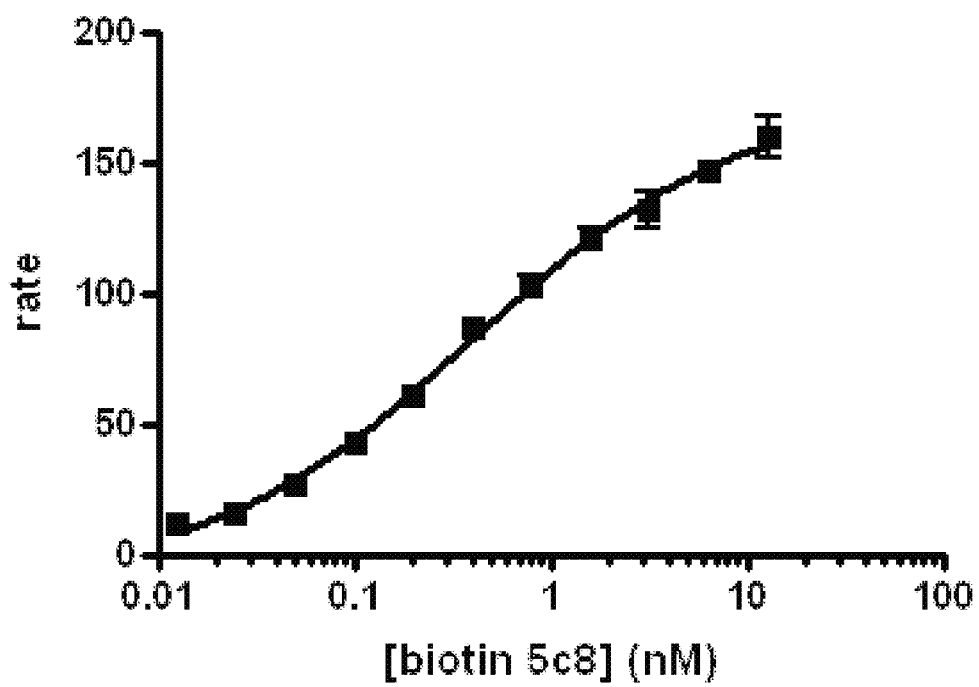

FIGURE 29 continued
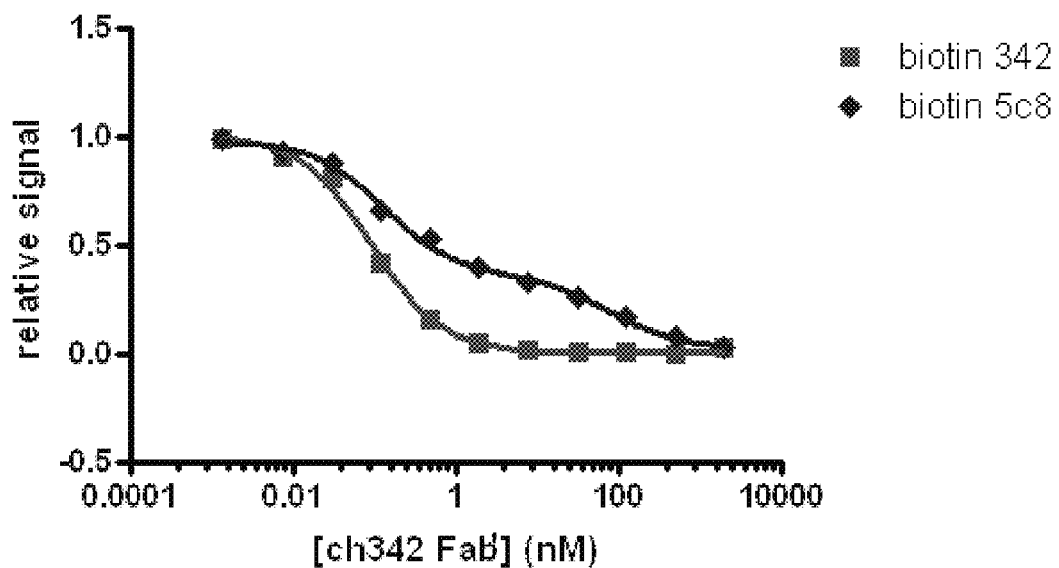
C.
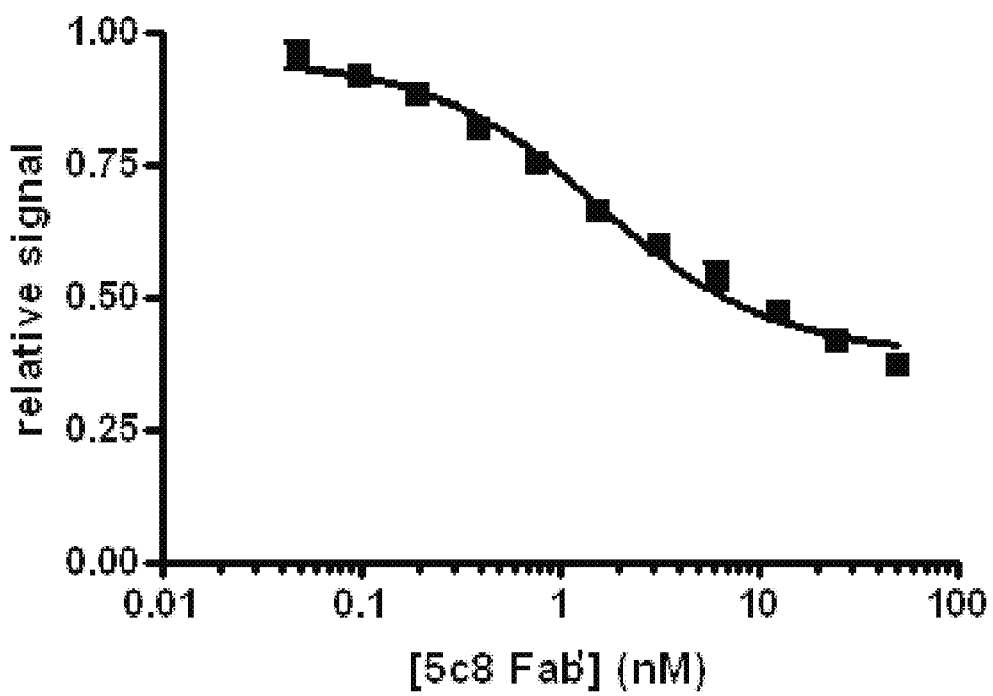
D.

BINDING PROTEINS, INCLUDING ANTIBODIES, ANTIBODY DERIVATIVES AND ANTIBODY FRAGMENTS, THAT SPECIFICALLY BIND CD154 AND USES THEREOF

CROSS-REFERENCE TO RELATED APPLICATIONS

This application is a divisional of U.S. Ser. No. 13/656,922, filed Oct. 22, 2012, now allowed, which is a continuation of U.S. Ser. No. 12/532,517, filed Sep. 22, 2009, now U.S. Pat. No. 8,293,237, which is the U.S. national stage application of International Application PCT/US2008/003735, filed Mar. 21, 2008, which claims priority from U.S. Provisional Patent Application No. 60/920,495, filed Mar. 27, 2007, U.S. Provisional Patent Application No. 60/919,938, filed Mar. 22, 2007 and U.S. Provisional Patent Application No. 60/919,816, filed Mar. 22, 2007. The contents of PCT/US2008/003735, U.S. 60/920,495, U.S. 60/919,938 and U.S. 60/919,816 are hereby incorporated by reference in their entirety.

The Sequence Listing for this application is labeled "SeqList.TXT" which was created on Sep. 16, 2009 and is 81 KB. The entire contents of the sequence listing is incorporated herein by reference in its entirety.

TECHNICAL FIELD OF THE INVENTION

This invention provides binding proteins, including antibodies, antibody derivatives and antibody fragments, that specifically bind a CD154 (CD40L) protein. This invention also provides a chimeric, humanized or fully human antibody, antibody derivative or antibody fragment that specifically binds to an epitope to which a humanized Fab fragment comprising a variable heavy chain sequence according to SEQ ID NO: 1 and comprising a variable light chain sequence according to SEQ ID NO: 2 specifically binds. CD154 binding proteins of this invention may elicit reduced effector function relative to a second anti-CD154 antibody. CD154 binding proteins of this invention are useful in diagnostic and therapeutic methods, such as in the treatment and prevention of diseases including those that involve undesirable immune responses that are mediated by CD154-CD40 interactions.

BACKGROUND OF THE INVENTION

The generation of humoral and cell-mediated immunity is orchestrated by the interaction of activated helper T cells with antigen-presenting cells ("APCs") and effector T cells. Activation of the helper T cells is not only dependent on the interaction of the antigen-specific T-cell receptor ("TCR") with its cognate peptide-MHC ligand, but also requires the coordinate binding and activation by a number of cell adhesion and costimulatory molecules. See, e.g. Salazar-Fontana, L. I., and B. E. Bierer (2001) *Curr. Opin. Hemat.* 8:5.

One critical costimulatory molecule is CD154, a Type II transmembrane protein that is expressed on the surface of $CD4^+$ T cells in an activation-dependent, temporally-restricted manner. CD154 is also expressed, following activation, on a subset of $CD8^+$ T cells, basophils, mast cells, eosinophils, natural killer cells, B cells, macrophages, dendritic cells and platelets. The CD154 counter-receptor, CD40, is a Type I membrane protein that is constitutively and widely expressed on the surface of many cell types, including APCs. See, e.g., Foy, T. M. et al. (1996) Ann *Rev. Immunol.* 14:591.

Signaling through CD40 by CD154 initiates a cascade of events that results in the activation of the CD40 receptor-bearing cells and optimal $CD4^+$ T cell priming. More specifically, the binding of CD154 to CD40 promotes the differentiation of B cells into antibody secreting cells and memory B cells. See, e.g., Burkly, L. C. (2001) *In Adv. Exp. Med. Bio.*, Vol. 489. D. M. Monroe et al. eds. Kluwer Academic/Plenum Publishers, p. 135 (hereafter "Burkly, supra"). Additionally, the CD154-CD40 interaction promotes cell-mediated immunity through the activation of macrophages and dendritic cells and the generation of natural killer cells and cytotoxic T lymphocytes. See, e.g., Burkly, ibid.

The pivotal role of CD154 in regulating the function of both the humoral and cell-mediated immune response has provoked great interest in the use of inhibitors of this pathway for therapeutic immunomodulation. As such, anti-CD154 antibodies have been shown to be beneficial in a wide variety of models of immune response to other therapeutic proteins or gene therapy, allergens, autoimmunity and transplantation. See, e.g., U.S. Pat. No. 5,474,771; Burkly, supra.

The CD40-CD154 interaction has been shown to be important in several experimentally induced autoimmune diseases where it has been shown that disease induction can be blocked with CD154 antagonists at the time of antigen administration (Burkly, supra). The blockade of disease using anti-CD154 antagonists has also been seen in animal models of spontaneous autoimmune disease. See, e.g., Burkly, supra.

There is currently a need for improved anti-CD154 antibodies with higher binding affinities and fewer unwanted side effects. Increased "effector functions" such as direct cytotoxicity, complement-dependent cytotoxicity ("CDC"), antibody-dependent cytotoxicity ("ADCC") and abnormal antibody production, are unwanted side effects that may be associated with therapeutic antibodies.

Several antibody effector functions are mediated at least in part by Fc receptors (FcRs), which bind the Fc region of an antibody in the constant domain of a typical immunoglobulin. There are a number of Fc receptors which are specific for the different classes of immunoglobulins. The classes of immunoglobulins include IgG, IgE, IgA, IgM, and IgD. The classes of immunoglobulins are further divided into subclasses: IgG is divided into four subclasses (IgG1, IgG2, IgG3, and IgG4) and IgA is divided into two subclasses (IgA1 and IgA2). There are three known receptors for IgG: FcγRI (CD64), FcγRII (CD32), and FcγRIII (CD16)). Each FcγR subclass is encoded by two or three genes, and alternative RNA splicing leads to multiple transcripts and a broad diversity in FcγR isoforms.

Typically, immunoglobulins are Y-shaped molecules comprising two identical heavy chains and two identical light chains. Disulfide bonds link together the heavy and light chain pairs as well as the two heavy chains. Each chain consists of one variable domain that varies in sequence and is responsible for antigen binding; these domains are known as the $V_H$ and $V_L$ domains for the heavy and light chains, respectively. In the light chain there is a single constant domain ($C_L$) and in the heavy chain there are three constant domains ($C_{H1}$, $C_{H2}$ and $C_{H3}$). Molecules containing all of the variable and constant domains may be referred to as whole antibodies.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al., supra"). This numbering system is used in the present specification except where otherwise indicated. It should be noted that the Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

There are three regions within the variable domains that are hypervariable in sequence set within four more highly conserved framework regions. These hypervariable CDRs are primarily responsible for antigen recognition. The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. *J. Mol. Biol.*, 1987, 196:901-917), the loop equivalent to CDR-H1 extends from residue 26 to residue 32. Thus 'CDR-H1', as used herein, also includes a CDR located at residues 26 to 35, as described by a combination of the Kabat numbering system and Chothia's topological loop definition. The CDRs of the light chain variable domain are located at residues 24-34 (CDR-L1), residues 50-56 (CDR-L2) and residues 89-97 (CDR-L3) according to the Kabat numbering system.

Though naturally occurring antibodies, as whole antibodies or as fragments retaining specific binding properties, were originally derived from a single species, engineered antibodies may be derived from more than one species of animal, e.g., chimeric antibodies. To date, mouse (murine)/human chimeric and murine/non-human primate antibodies have principally been generated, though other hybrid species combinations are possible. Many different configurations of naturally occurring and engineered antibody polypeptides, and derivatives and fragments thereof, are now known. The feature common to all is that the polypeptide or polypeptides retain antigen-binding specificity through one or more epitope-binding domains. Aside from epitope binding, the functional properties of an antibody polypeptide may differ depending on what other sequences are present, e.g., Fc domains or other sequences that activate effector functions and/or interact with other cellular pathways.

CD154 binding proteins that comprise epitope-binding domains (such as CDRs or variable domains) incorporated into a non-immunoglobulin scaffold or framework (see, for example, Binz et al. 2005 *Nat Biotech* 23: 1257-1268; Hosse et al. 2006 *Protein Science* 15: 14-27) may exhibit reduced effector functions. It would be desirable to have new binding proteins that specifically antagonize CD154 binding to CD40 and reduce or eliminate downstream functions of the CD154-CD40 complex. It would also be desirable to have CD154 binding proteins, such as anti-CD154 antibodies, with reduced effector functions compared to known anti-CD154 antibodies.

SUMMARY OF THE INVENTION

The present invention provides a solution to these and other problems by providing a binding protein, such as an isolated, recombinant or synthetic antibody, or fragment or derivative thereof, that specifically binds a CD154 protein, which may be a human CD154 protein. Anti-CD154 antibodies of the invention, including fragments and derivatives thereof, may be monoclonal, polyclonal, murine, chimeric, primatized, humanized or fully human antibodies. Anti-CD154 antibodies of the invention may be multimeric, heterodimeric, hemi-dimeric, monovalent, bivalent, tetravalent, bispecific and may include single chain antibodies; and derivatives thereof.

In certain embodiments, CD154 binding proteins, e.g., anti-CD154 antibodies, of the present invention have high selectivity for CD154 and, in some embodiments, also have one or more reduced effector functions compared, for example, to anti-CD154 antibody 5c8 (produced by the hybridoma deposited under ATCC Accession No. HB 10916, as described in U.S. Pat. No. 5,474,771; or humanized 5c8). Certain of the CD154 binding proteins, e.g., anti-CD154 antibodies, of the invention are monovalent for CD154 binding.

CD154 binding proteins and anti-CD154 antibodies (including antibody fragments and derivatives) of the invention are useful for inhibiting binding of CD154 to CD40 and do so with high specificity, e.g., with an IC50 in the range of 20 pM to 1.5 μM, inclusive. In certain embodiments, the CD154 binding proteins, e.g., anti-CD154 antibodies, of the invention may have an IC50 in the range of 20 pm to 500 pm, 50 pm to 500 pm or 100 pm to 500 pm. In certain embodiments, CD154 binding proteins and anti-CD154 antibodies (including antibody fragments and derivatives) of the invention do not substantially agonize CD40 activity.

Certain embodiments of the present invention relate to CD154 binding proteins, e.g., anti-CD154 antibodies, that exhibit a high affinity for human CD154. For example, in certain embodiments, a CD154 binding protein, e.g., anti-CD154 antibody, dissociates from human CD154 (human CD40L) with a $K_D$ in the range of 50 nM to 1 pM, inclusive, as determined by surface plasmon resonance (e.g., Biacore®). For example, the $K_D$ for human CD154 may be 50 pM to 1 pM, 20 pM to 1 pM or even 10 pM to 1 pM. In some embodiments, the $K_D$ for human CD154 is less than 20 pM. In other embodiments, the $K_D$ for human CD154 is less than 10 pM.

In certain embodiments, this invention provides a CD154 binding protein, e.g., anti-CD154 antibody, which when present at or above saturating concentrations for CD154 binding based on its binding affinity, is capable of blocking binding of antibody 5c8 to CD154 when added to CD154 first, and is also capable of displacing antibody 5c8 bound to CD154 when added after antibody 5c8 is added to CD154.

In certain embodiments, this invention provides a binding protein, e.g., antibody, that specifically binds a CD154 protein and which comprises or consists of one or more CDR heavy chain (H) sequence(s) selected from CDR-H1 (SEQ ID NO: 3), CDR-H2 (SEQ ID NO: 4) and CDR-H3 (SEQ ID NO: 5). In further embodiments, the CD154 binding protein or antibody comprises or consists of at least two CDRs selected from CDR-H1 (SEQ ID NO: 3), CDR-H2 (SEQ ID NO: 4) and CDR-H3 (SEQ ID NO: 5). In yet further embodiments the binding protein or antibody comprises or consists of all three CDR H sequences, which are the CDR-H1 (SEQ ID NO: 3), the CDR-H2 (SEQ ID NO: 4) and the CDR-H3 (SEQ ID NO: 5).

In certain embodiments, this invention provides a binding protein, e.g., antibody, that specifically binds a CD154 protein and which comprises or consists of one or more CDR light chain (L) sequence(s) selected from CDR-L1 (SEQ ID NO: 6), CDR-L2 (SEQ ID NO: 7) and CDR-L3 (SEQ ID NO: 8). In further embodiments, the CD154 binding protein or antibody comprises or consists of at least two CDRs selected from CDR-L1 (SEQ ID NO: 6), CDR-L2 (SEQ ID NO: 7) and CDR-L3 (SEQ ID NO: 8). In yet further embodiments, the CD154 binding protein or antibody comprises or consists of all three CDR L sequences, which are CDR-L1 (SEQ ID NO: 6), CDR-L2 (SEQ ID NO: 7) and CDR-L3 (SEQ ID NO: 8).

In certain embodiments, this invention provides a binding protein, e.g., antibody, that specifically binds a CD154 protein and that comprises or consists of CDR-L1 (SEQ ID NO:

6), CDR-L2 (SEQ ID NO: 7) and CDR-L3 (SEQ ID NO: 8), and wherein the binding protein or antibody further comprises or consists of CDR-H1 (SEQ ID NO: 3), CDR-H2 (SEQ ID NO: 4) and CDR-H3 (SEQ ID NO: 5).)

In certain embodiments, this invention provides a binding protein, e.g., antibody, that specifically binds a CD154 protein, wherein the CD154 binding protein or antibody comprises or consists of a $V_H$ sequence selected from SEQ ID NO: 1, SEQ ID NO: 9, SEQ ID NO: 10 and SEQ ID NO: 11. In certain other embodiments, this invention provides a binding protein, e.g., antibody, that specifically binds a CD154 protein, wherein the CD154 binding protein or antibody comprises or consists of a heavy chain sequence selected from SEQ ID NO: 12 and SEQ ID NO: 13.

In certain embodiments, this invention provides a binding protein, e.g., antibody, that specifically binds a CD154 protein, wherein the CD154 binding protein or antibody comprises or consists of a $V_L$ sequence selected from SEQ ID NO: 2 and SEQ ID NO: 14. In certain embodiments, this invention provides a binding protein, e.g., antibody, that specifically binds a CD154 protein, wherein the CD154 binding protein or antibody comprises or consists of the light chain sequence of SEQ ID NO: 15.

In certain embodiments, this invention provides a binding protein, e.g. antibody, that specifically binds a CD154 protein, wherein the CD154 binding protein or antibody comprises or consists of a $V_L$ sequence selected from SEQ ID NO: 2, and SEQ ID NO: 14 and a $V_H$ sequence selected from SEQ ID NO: 1, SEQ ID NO: 9, SEQ ID NO: 10 and SEQ ID NO: 11. In certain embodiments, this invention provides a binding protein, e.g., antibody, that specifically binds a CD154 protein, wherein the CD154 binding protein or antibody comprises or consists of a light chain sequence of SEQ ID NO: 15 and a heavy chain sequence selected from SEQ ID NO: 12 and SEQ ID NO: 13. In other embodiments, the CD154 binding protein or antibody comprises or consists of a light chain sequence of SEQ ID NO: 15 and a heavy chain sequence of SEQ ID NO: 13.

In other embodiments, the present invention relates to a binding protein, e.g. an antibody, that specifically binds CD154, and comprises or consists of one or more heavy chain (H) CDR sequence(s) selected from CDR-H1 (SEQ ID NO: 42), CDR-H2 (SEQ ID NO: 43) and CDR-H3 (SEQ ID NO: 44). In further embodiments, the binding protein or antibody comprises or consists of at least two CDRs selected from CDR-H1 (SEQ ID NO: 42), CDR-H2 (SEQ ID NO: 43) and CDR-H3 (SEQ ID NO: 44). In yet further embodiments, the binding protein or antibody comprises or consists of all three CDR H sequences, which are CDR-H1 (SEQ ID NO: 42), CDR-H2 (SEQ ID NO: 43) and the CDR-H3 (SEQ ID NO: 44.)

In certain embodiments, this invention provides a binding protein, e.g. an antibody, that specifically binds a CD154 protein, wherein the binding protein or antibody comprises or consists of one or more CDR light chain (L) sequence selected from CDR-L1 (SEQ ID NO: 45), CDR-L2 (SEQ ID NO: 46) and CDR-L3 (SEQ ID NO: 47). In further embodiments, the binding protein or antibody comprises or consists of at least two CDRs selected from CDR-L1 (SEQ ID NO: 45), CDR-L2 (SEQ ID NO: 46) and CDR-L3 (SEQ ID NO: 47). In yet further embodiments, the binding protein or antibody comprises or consists of all three CDR L sequences, which are CDR-L1 (SEQ ID NO: 45), CDR-L2 (SEQ ID NO: 46) and CDR-L3 (SEQ ID NO: 47.)

In certain embodiments, a CD154 binding protein or anti-CD154 antibody of the present invention comprises a complementary sequence comprising or consisting of one or more light chain CDRs of CDR-L1, CDR-L2 and CDR-L3, above, or a complementary sequence comprising or consisting of one or more heavy chain CDRs of CDR-H1, CDR-H2 and CDR-H3, above, respectively. Thus, in certain embodiments, a binding protein or antibody of this invention comprises or consists of CDR-H1 (SEQ ID NO: 42), CDR-H2 (SEQ ID NO: 43) or CDR-H3 (SEQ ID NO: 44), and CDR-L1 (SEQ ID NO: 45), CDR-L2 (SEQ ID NO: 46) or CDR-L3 (SEQ ID NO: 47).

In certain embodiments, this invention provides a CD154 binding protein, e.g., an anti-CD154 antibody, wherein the binding protein or antibody comprises or consists of the following three CDR L sequences: CDR-L1 (SEQ ID NO: 45), CDR-L2 (SEQ ID NO: 46) and CDR-L3 (SEQ ID NO: 47), and wherein the binding protein or antibody further comprises or consists of the following three CDR H sequences: CDR-H1 (SEQ ID NO: 42), CDR-H2 (SEQ ID NO: 43) and CDR-H3 (SEQ ID NO: 44.)

In further embodiments, this invention provides a binding protein, e.g., antibody, that specifically binds CD154 and which comprises or consists of a variable light chain ($V_L$) sequence of SEQ ID NO: 54. The invention also relates to a CD154 binding protein or anti-CD154 antibody that comprises or consists of a variable heavy chain ($V_H$) sequence of SEQ ID NO: 56. In certain embodiments, a CD154 binding protein or anti-CD154 antibody of the invention may comprise or consist of both a $V_L$ sequence of SEQ ID NO: 54 and a $V_H$ sequence of SEQ ID NO: 56.

In other embodiments, the present invention relates to a CD154 binding protein, e.g., an anti-CD154 antibody, that specifically binds CD154, wherein the CD154 binding protein or anti-CD154 antibody comprises or consists of one or more heavy chain (H) CDR sequence(s) selected from CDR-H1 (SEQ ID NO: 48), CDR-H2 (SEQ ID NO: 49) and CDR-H3 (SEQ ID NO: 50). In further embodiments, the CD154 binding protein or anti-CD154 antibody comprises or consists of at least two CDRs selected from CDR-H1 (SEQ ID NO: 48), CDR-H2 (SEQ ID NO: 49) and CDR-H3 (SEQ ID NO: 50). In yet further embodiments, the CD154 binding protein or anti-CD154 antibody comprises or consists of all three CDR H sequences, which are CDR-H1 (SEQ ID NO: 48), CDR-H2 (SEQ ID NO: 49) and CDR-H3 (SEQ ID NO: 50.)

In certain embodiments, this invention provides a CD154 binding protein, e.g., an anti-CD154 antibody, that specifically binds a CD154 protein, wherein the CD154 binding protein or anti-CD154 antibody comprises or consists of one or more CDR light chain (L) sequence selected from CDR-L1 (SEQ ID NO: 51), CDR-L2 (SEQ ID NO: 52) and CDR-L3 (SEQ ID NO: 53). In further embodiments, the CD154 binding protein or anti-CD154 antibody comprises or consists of at least two CDRs selected from CDR-L1 (SEQ ID NO: 51), CDR-L2 (SEQ ID NO: 52) and CDR-L3 (SEQ ID NO: 53). In yet further embodiments, the CD154 binding protein or anti-CD154 antibody comprises or consists of all three CDR L sequences, which are CDR-L1 (SEQ ID NO: 51), CDR-L2 (SEQ ID NO: 52) and CDR-L3 (SEQ ID NO: 53.)

In certain embodiments, a CD154 binding protein, e.g., an anti-CD154 antibody, of the present invention comprises a complementary sequence comprising or consisting of one or more light chain CDRs of CDR-L1, CDR-L2 and CDR-L3, above, or a complementary sequence comprising or consisting of one or more heavy chain CDRs of CDR-H1, CDR-H2 and CDR-H3, above, respectively. Thus, in certain embodiments, an antibody of this invention comprises or consists of a CDR H selected from CDR-H1 (SEQ ID NO: 48), CDR-H2 (SEQ ID NO: 49) and CDR-H3 (SEQ ID NO: 50), or a CDR L selected from CDR-L1 (SEQ ID NO: 51), CDR-L2 (SEQ ID NO: 52) and CDR-L3 (SEQ ID NO: 53).

In certain embodiments, this invention provides a CD154 binding protein, e.g., an anti-CD154 antibody, wherein the CD154 binding protein or anti-CD154 antibody comprises or consists of all three CDR L sequences, which are CDR-L1 (SEQ ID NO: 51), CDR-L2 (SEQ ID NO: 52) and CDR-L3 (SEQ ID NO: 53), and wherein the binding protein, e.g., antibody, further comprises or consists of all three CDR H sequences, which are: CDR-H1 (SEQ ID NO: 48), CDR-H2 (SEQ ID NO: 49) and CDR-H3 (SEQ ID NO: 50).

In further embodiments, this invention provides a CD154 binding protein, e.g., an anti-CD154 antibody, that specifically binds CD154, wherein the CD154 binding protein or anti-CD154 antibody comprises or consists of a $V_L$ sequence of SEQ ID NO: 58. In additional embodiments, the antibody comprises or consists of a $V_H$ sequence of SEQ ID NO: 60. In further embodiments, the antibody comprises or consists of a $V_H$ sequence of SEQ ID NO: 60 and a $V_L$ sequence of SEQ ID NO: 58.

In certain embodiments, the CD154 binding protein of this invention comprises a light chain sequence according to SEQ ID NO: 62 and a heavy chain sequence according to SEQ ID NO: 65. In other embodiments, the CD154 binding protein of this invention comprises a light chain sequence according to SEQ ID NO: 63 and a heavy chain sequence according to SEQ ID NO: 66.

In certain embodiments, the CD154 binding protein of this invention comprises a light chain sequence according to SEQ ID NO: 68 and a heavy chain sequence according to SEQ ID NO: 71. In other embodiments, the CD154 binding protein of this invention comprises a light chain sequence according to SEQ ID NO: 69 and a heavy chain sequence according to SEQ ID NO: 72. In other embodiments, the CD154 binding protein comprises at least one of the sequences according to SEQ ID NO: 68, SEQ ID NO: 69, SEQ ID NO: 71 and SEQ ID NO: 72.

The CDR sequences of SEQ ID NOS: 3-8 are derived from rat monoclonal antibody 342. In an alternative embodiment of the invention, the anti-CD154 antibody is the rat 342 antibody comprising the $V_H$ domain sequence of SEQ ID NO: 29 and the $V_L$ domain sequence of SEQ ID NO: 30. The invention also provides an isolated, recombinant or synthetic DNA molecule that comprises or consists of at least one sequence selected from SEQ ID NO: 31 and SEQ ID NO: 32. Additionally provided is a vector comprising at least one sequence selected from SEQ ID NO: 33 and SEQ ID NO: 34.

The invention also provides CD154 binding proteins, e.g., anti-CD154 antibodies, that bind selectively to the same epitope as does any one of the anti-CD154 antibodies disclosed herein (e.g., 342, 381 and 338 antibodies and epitope binding sequences thereof). In particular, antibodies 342 and 338 of the present invention exhibit similar CD154 binding properties when used as first or second antibodies in competition assays with the anti-CD154 antibody 5c8, as described herein.

Thus, in certain embodiments, the invention provides CD154 binding proteins and anti-CD154 antibodies that bind to the same epitope as does a humanized antibody comprising a heavy chain sequence according to SEQ ID NO. 12 or SEQ ID NO. 13 and comprising a light chain sequence according to SEQ ID NO. 15 (342 Fab and Fab' fragments), and which exhibit similar CD154 binding properties when used as first or second antibodies in competition assays with the anti-CD154 antibody 5c8, as described herein. In other embodiments, the invention provides CD154 binding proteins and anti-CD154 antibodies that bind to the same epitope as does a humanized antibody comprising a $V_L$ domain sequence according to SEQ ID NO. 58 and a $V_H$ domain sequence according to SEQ ID NO. 60 (338 antibody variable sequences), and which exhibit similar CD154 binding properties in competition assays with anti-CD154 antibody 5c8, as described herein.

In any of the above embodiments relating to a CD154 binding protein of the invention, the binding protein may be PEGylated. In embodiments in which the CD154 binding protein is an anti-CD154 antibody, antibody polypeptide or fragment or derivative thereof, the antibody may be PEGylated on the heavy chain, the light chain, or on both chains.

The present invention also provides an isolated, recombinant and/or synthetic DNA molecule that comprises or consists of at least one sequence selected from SEQ ID NO: 16, SEQ ID NO: 17, SEQ ID NO: 18 and SEQ ID NO: 25.

In certain embodiments, this invention also provides an isolated, recombinant and/or synthetic DNA molecule that comprises or consists of at least one sequence selected from SEQ ID NO: 19, SEQ ID NO: 20, SEQ ID NO: 21, SEQ ID NO: 22, SEQ ID NO: 23, SEQ ID NO: 24, SEQ ID NO: 26, SEQ ID NO: 27, SEQ ID NO: 67, SEQ ID NO: 70 and SEQ ID NO: 73.

In other embodiments, the invention provides an isolated, recombinant and/or synthetic DNA molecule that comprises or consists of at least one sequence selected from SEQ ID NO: 28 and SEQ ID NO: 41.

This invention also provides a vector that comprises any one of the isolated, recombinant and/or synthetic DNA molecules of this invention. In one embodiment, the vector comprises at least one sequence selected from SEQ ID NO: 25, SEQ ID NO: 26, SEQ ID NO: 27, SEQ ID NO: 28 and SEQ ID NO: 41.

In additional embodiments, this invention provides an isolated, recombinant, and/or synthetic DNA molecule that comprises or consists of at least one sequence selected from SEQ ID NO: 55 and SEQ ID NO: 57. In some embodiments, the invention provides an isolated, recombinant, and/or synthetic DNA molecule comprising or consisting of both SEQ ID NO: 55 and SEQ ID NO: 57.

In additional embodiments, this invention provides an isolated, recombinant, and/or synthetic DNA molecule that comprises or consists of at least one sequence selected from SEQ ID NO: 59 and SEQ ID NO: 61. In some embodiments, the invention provides an isolated, recombinant, and/or synthetic DNA molecule comprising or consisting of both SEQ ID NO: 59 and SEQ ID NO: 61.

In any of the embodiments of the invention relating to CD154 binding proteins and anti-CD154 antibodies that comprise sequences which contribute to effector functions, said binding proteins or anti-CD154 antibodies may additionally be selected or engineered to elicit reduced effector function compared to an anti-CD154 antibody having an Fc region, as described elsewhere herein. For example, CD154 binding proteins and anti-CD154 antibodies that are free of an Fc region or constant region sequences, or which lack a functional Fc region or constant region sequences, may be selected for use in the invention.

In certain embodiments, CD154 binding proteins and anti-CD154 antibodies of the invention are monovalent for binding to CD154 and preferably elicit reduced effector functions when administered to a subject relative to a comparable CD154 binding protein such as a bivalent anti-CD154 antibody.

In certain other embodiments, Fc or constant region sequences, if present in a CD154 binding protein, e.g., anti-CD154 antibody polypeptide, may be selected or engineered to comprise one or more modifications (e.g., amino acid substitutions, insertions, adducts or deletions) that reduce or eliminate one or more effector function(s) relative to a control anti-CD154 antibody comprising native, parental or unmodified Fc or constant region sequences.

In some embodiments of the invention, an Fc region, when present, is an Fc region of or derived from an IgG1, IgG2, IgG3 or IgG4 antibody. In some embodiments, hybrid Fc regions may be used, i.e., IgG1/IgG4 hybrid Fc sequences. In particular embodiments, the Fc region comprises IgG4 Fc sequences or is derived from an IgG4 antibody. It is to be understood that any hybrid combination between different Fc regions that reduces one or more effector functions may be used according to the invention.

In certain other embodiments, glycosylation of the Fc portion of an antibody is reduced or eliminated, or the glycosylation profile of the antibody altered, as described further herein. In certain embodiments, a CD154 binding protein or anti-CD154 antibody polypeptide comprises a $C_{H2}$ domain with an Fc region having a modification at or close to the conserved N-linked glycosylation site. The modification at the conserved N-linked glycosylation site may comprise a mutation in or near the heavy chain glycosylation site, wherein the mutation reduces, alters or prevents glycosylation at the site. In further embodiments, the modification comprises mutation N298Q (N297 using EU Kabat numbering). In certain embodiments, the modification comprises removal of $C_{H2}$ domain glycans or portions thereof. In certain alternative embodiments, the modification prevents formation of a mature N-glycan at the glycosylation site.

In some embodiments, the present invention relates to a CD154 binding protein, e.g., an anti-CD154 antibody, comprising a heavy chain CDR3 sequence selected from SEQ ID NOS: 5, 44 and 50, and a variant Fc region, the variant Fc region comprising a first amino acid residue and an N-glycosylation site, the first amino acid residue modified with side chain chemistry or by amino acid substitution to achieve increased steric bulk or increased electrostatic charge compared to the unmodified first amino acid residue, thereby reducing the level of or otherwise altering glycosylation at the N-glycosylation site. In certain of these embodiments, the variant Fc region confers reduced effector function compared to a control, non-variant Fc region.

In certain embodiments, the invention relates to a CD154 binding protein, e.g., an anti-CD154 antibody, comprising a heavy chain CDR3 sequence selected from SEQ ID NOS: 5, 44 and 50, and a variant Fc region, the variant Fc region comprising a first amino acid residue and an N-glycosylation site, the first amino acid residue comprising a cysteine thiol thereby reducing the level of or altering glycosylation at the N-glycosylation site, wherein the variant Fc region confers reduced effector function.

In certain embodiments, the first amino acid residue and the N-glycosylation site of the anti-CD154 antibodies comprising variant Fc regions described above are near or within an N-linked glycosylation motif. In further embodiments, the N-linked glycosylation motif comprises the amino acid sequence NXT or NXS. In certain embodiments, the N-linked glycosylation motif comprises the amino acid sequence NXT. In certain embodiments, the N-glycosylation site is located at amino acid 297 according to the Kabat numbering system. In additional embodiments, the modified first amino acid residue is amino acid 299 according to the Kabat numbering system.

In certain of the above embodiments, the reduced effector function exhibited by any one of the antibodies or antibody fragment containing binding proteins described herein is reduced binding to an Fc receptor (FcR). In certain embodiments, the Fc receptor (FcR) is selected from FcγRI, FcγRII and FcγRIII, and one or more subtypes thereof, such as, for example, FcγRIIa. In some embodiments, the FcR binding is reduced by a factor of at least about 1.5-fold or more, about 2-fold or more, about 3-fold or more, about 4-fold or more, about 5-fold or more, about 6-fold or more, about 7-fold or more, about 8-fold or more, about 9-fold or more, about 10-fold or more, about 15-fold or more, about 50-fold or more, or about 100-fold or more.

In certain embodiments, a CD154 binding protein, e.g., an anti-CD154 antibody, of the invention with one or more reduced effector function(s) as described herein does not bind to a specific effector receptor or effector receptor subtype. In certain of these embodiments, the CD154 binding protein, e.g., an anti-CD154 antibody, does not bind to FcγRIIa.

In certain embodiments, the reduced effector function exhibited by any one of the antibodies described herein is reduced binding to a complement protein. In some embodiments, the complement protein is C1q. In certain embodiments, the reduced binding to a complement protein is by a factor of about 1.5-fold or more, about 2-fold or more, about 3-fold or more, about 4-fold or more, about 5-fold or more, about 6-fold or more, about 7-fold or more, about 8-fold or more, about 9-fold or more, about 10-fold or more, or about 15-fold or more.

In further embodiments of the present invention, a CD154 binding protein, e.g., an anti-CD154 antibody, of the invention comprises one or more modifications or variations in the Fc region, is not glycosylated and elicits one or more reduced effector functions when administered to a subject.

In certain embodiments, a CD154 binding protein, e.g., an anti-CD154 antibody, of the invention causes fewer thromboembolic effects than does administration of anti-CD154 antibody 5c8 when administered to a subject.

In certain embodiments of the present invention, the modified first amino acid residue of the CD154 binding proteins or anti-CD154 antibodies comprising variant Fc regions described above is linked to a functional moiety. In further embodiments, the functional moiety is a blocking moiety, a detectable moiety, a diagnostic moiety or a therapeutic moiety, or a combination thereof. A blocking moiety, in certain embodiments, may be, for example, a cysteine adduct, mixed disulfide, polyethylene glycol or polyethylene glycol maleimide. A detectable moiety, in certain embodiments, may be, for example, a fluorescent moiety, a luminescent moiety or an isotopic moiety. In embodiments where a diagnostic moiety is used, the diagnostic moiety may be capable of revealing the presence of a condition, disease or disorder. In other embodiments, a therapeutic moiety such as, for example, an anti-inflammatory agent, an anti-cancer agent, an anti-neurodegenerative agent, an antibody that is selective for a molecule other than CD154, or an anti-infective agent, may be used.

In certain embodiments of the present invention, a CD154 binding protein, e.g., an anti-CD154 antibody, comprises a modified amino acid residue, the modification allowing site-directed conjugation of the protein or antibody to a functional moiety, such as for site-directed pegylation. In certain embodiments, the modified amino acid residue is a cysteine residue modified by a cysteine or mixed disulfide adduct. Thus, in certain embodiments, the CD154 binding protein is an anti-CD154 antibody polypeptide that is pegylated at a modified amino acid residue, e.g., at a cysteine or lysine residue. In certain embodiments, the anti-CD154 antibody is a Fab or Fab' fragment pegylated with PEG-maleimide.

This invention also provides nucleic acid, e.g., DNA sequences encoding the CD154 binding proteins, e.g., anti- CD154 antibodies, of the invention. The DNA sequences of the present invention may comprise synthetic DNA, for instance produced by chemical processing, cDNA, genomic DNA or any combination thereof. This invention further provides cloning or expression vectors comprising one or more nucleic acid, e.g., DNA sequences of the present invention. The invention also relates, in some embodiments, to a vector comprising any of the synthetic, isolated, and/or recombinant nucleic acids described above.

This invention also provides a host cell comprising a DNA sequence or vector of the invention. In certain aspects, the present invention relates to a method for producing a CD154 binding protein, e.g., an anti-CD154 antibody, comprising culturing a host cell comprising any of the vectors described above under conditions suitable for producing the CD154 binding protein or anti-CD154 antibody by the host cell. In some embodiments, the method comprises recovering the CD154 binding protein or anti-CD154 antibody from the host cell culture.

In certain embodiments, the CD154 binding protein, anti-CD154 antibody or nucleic acid of this invention is labeled with a detectable marker, which may be a radioactive isotope, enzyme, dye or biotin. In certain other embodiments, the antibody of this invention is conjugated to at least one other therapeutic agent, which may be a radioisotope, radionuclide, toxin, toxoid, a non-CD154 specific antibody polypeptide or fragment (i.e., creating a bispecific or multispecific antibody), or chemotherapeutic agent, for example. In yet other embodiments, the antibody of this invention is conjugated to an imaging agent, which could be a labeling moiety. The labeling agent may also be a biotin, a fluorescent or luminescent moiety, a radioactive moiety, a histidine tag, or a peptide tag.

The present invention also relates to sequence variants of the CD154 binding proteins, e.g., anti-CD154 antibodies, described herein, and nucleic acid sequences that encode them. Sequence variants of the invention preferably share at least 90%, 91%, 92%, 93% or 94% identity with a polypeptide of the invention or with a nucleic acid sequence that encodes it. More preferably, a sequence variant shares at least 95%, 96%, 97% or 98% identity at the amino acid or nucleic acid level. Most preferably, a sequence variant shares at least 99%, 99.5%, 99.9% or more identity with a polypeptide of the invention or a nucleic acid sequence that encodes it.

Accordingly, the present invention provides an isolated protein comprising a sequence that is at least 80, 85, 90, 92, 94, 95, 96, 97, 98, 99, 99.5, 99.9 or 100% identical to the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 29, SEQ ID NO: 30, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 56, SEQ ID NO: 58, SEQ ID NO: 60, SEQ ID NO: 68, SEQ ID NO: 69, SEQ ID NO: 71 or SEQ ID NO: 72.

In certain embodiments, a chimeric, humanized or human anti-CD154 antibody polypeptide of the invention is, for example, a dAb, Fab, Fab', scFv, Fv, a disulfide-bonded Fv or comprises a single immunoglobulin variable domain, such as a $V_H$ or a $V_L$ domain, that is specific and monovalent for CD154 binding. Certain CD154 binding proteins, e.g., chimeric, humanized or human anti-CD154 antibody polypeptides, of the invention comprise one, two or more CDRs of the invention and alternative scaffold or universal framework sequences. In certain embodiments, CD154 binding proteins and anti-CD154 antibodies of the invention comprise a single variable domain selected from a variable heavy chain ($V_H$) and a variable light chain ($V_L$).

This invention also provides a CD154 binding protein, e.g., a chimeric, humanized or human anti-CD154 antibody polypeptide, that is monovalent for binding to CD154 which is conjugated to a functional moiety that increases its in vivo half-life relative to the same polypeptide lacking the functional moiety. In certain embodiments, the functional moiety comprises or consists of polyethylene glycol. In certain embodiments, the functional moiety comprises or consists of an albumin molecule, such as human serum albumin. Accordingly, the invention provides a PEG-linked CD154 binding protein, e.g., a PEG-linked chimeric, humanized or human anti-CD154 antibody polypeptide that specifically and monovalently binds CD154, and which has an increased in vivo half-life relative to the same polypeptide lacking linked polyethylene glycol.

This invention also provides a pharmaceutical composition comprising at least one CD154 binding protein, e.g., an anti-CD154 antibody, of the present invention, which may, in some embodiments, further comprise a pharmaceutically acceptable carrier. A pharmaceutical composition of the invention may optionally further comprise an additional bioactive or therapeutic agent, such as, for example, an immunosuppressive or immunomodulatory compound or agent; or a diagnostic agent. In certain embodiments, the composition comprises a therapeutically effective amount of a pegylated, anti-CD154 Fab' antibody having the epitope specificity of anti-CD154 antibody 342 or 338, as described herein.

The present invention further provides a method for treating or preventing a human condition, disorder, disease mediated in whole or in part by CD40 signaling, or a symptom of any of the foregoing, the method comprising the step of administering to a subject in need thereof a therapeutically effective amount of a pharmaceutical composition comprising a CD154 binding protein, e.g., an anti-CD154 antibody, of the present invention, such that therapy or prevention of the condition, disease or disorder is achieved.

This invention also provides a method for inhibiting or preventing one or more of an immune, auto-immune or inflammatory response mediated in whole or in part by CD40 signaling, or a symptom of any of the foregoing, the method comprising the step of administering to a subject in need thereof a therapeutically effective amount of a pharmaceutical composition comprising a CD154 binding protein, e.g., an anti-CD154 antibody, of the present invention, such that a therapeutic or preventative response is achieved. In certain embodiments, the method is used to treat a subject presenting signs of or diagnosed with systemic lupus erythematosis (SLE). In other embodiments, the method is used to treat a subject presenting signs of or diagnosed with a rheumatoid condition, such as, for example, rheumatoid arthritis (RA).

This invention provides a human antibody polypeptide that is monovalent for binding to CD154. In certain embodiments, the human antibody polypeptide that is monovalent for binding to CD154, when present at or above saturating concentrations for CD154 binding based on its binding affinity, both blocks binding of antibody 5c8 to CD154 when added to CD154 first, and displaces antibody 5c8 bound to CD154 when added after antibody 5c8 is added. In certain embodiments, the human antibody polypeptide is PEG-linked. In certain embodiments, the human antibody polypeptide is free of an Fc domain. In certain of the above embodiments, the CD154 binding protein or human antibody polypeptide does not displace CD154 bound to CD40.

In certain embodiments, the invention provides a pegylated anti-CD154 Fab' antibody that is monovalent for CD154 binding and further provides methods for treating or preventing one or more symptoms of arthritis, such as rheumatoid arthritis, or systemic lupus erythematosis (SLE), comprising the step of administering to a subject in need thereof a therapeutically effective amount of a pharmaceutical composition comprising the pegylated, anti-CD154 Fab' antibody, such that a therapeutic or preventative response is achieved.

BRIEF DESCRIPTION OF THE DRAWINGS

FIG. 1 is a table providing the amino acid sequences for the complementarity determining regions (CDRs) of the anti-CD154 antibodies 342, 381, and 338.

FIG. 2 is a table providing the amino acid and corresponding nucleotide sequences for the $V_H$ and $V_L$ domains of the rat anti-CD154 antibody 342. Underlined sequences correspond to the nucleotide sequence encoding a leader (i.e., signal) peptide.

FIG. 3 is a table providing the amino acid and corresponding nucleotide sequences of human acceptor frameworks used to produce humanized anti-CD154 antibodies in the Examples.

FIG. 4 is a table providing the amino acid and corresponding nucleotide sequences of $V_H$ and $V_L$ domains in which the 342 CDRs have been grafted into the frameworks shown in FIG. 3.

FIG. 5 is a table providing the amino acid sequences and corresponding nucleotide sequences of $V_H$ domains of antibody 342 (VH3 gH1 and VH4 gH1) in which the 342 CDRs were grafted into human acceptor frameworks and wherein certain key donor residues were maintained.

FIG. 6 is a table providing the amino acid and corresponding nucleotide sequences of a $V_L$ domain of antibody 342 (VK1 gL4) in which the 342 CDRs were grafted into human acceptor frameworks and wherein certain key donor residues were maintained.

FIG. 7 is a table providing sequences for the complete light chain (variable and constant light chain regions) and heavy chain regions of antibody 342. Sequences corresponding to signal/leader peptides are underlined.

FIG. 8 shows the nucleotide sequence of expression inserts that were used to make Fab (SEQ ID NO: 28) and Fab' (SEQ ID NO: 41) versions of graft 342 gL4gH1. The signal/leader sequences are underlined and restriction sites (used for cloning into the E. coli expression vector as described in Example 2) are capitalized and shown in bold.

FIG. 9 shows an alignment of light and heavy chains of the rat 342 anti-CD154 antibody (donor) amino acid sequence with the human germline (acceptor) frameworks used in the humanization of the 342 antibody. "Light 342" is the rat $V_L$ domain sequence. "Heavy 342" is the rat $V_H$ domain sequence. The CDR residues are bold and underlined. The acceptor framework light (2 1 1 O12; SEQ ID NO: 35) and heavy (1-1 3-66; SEQ ID NO: 37 and 1-1 4-59; SEQ ID NO: 39) chains are shown. CDR-only grafts into human germline acceptor frameworks are also shown (VK1 gL3, VH3 gH7 and VH4 gH6). In certain humanized heavy and light chains, donor residues of the 342 antibody are retained within the framework region, and these key donor framework residues are shown in bold italics and are highlighted. The VK1 gL4 donor content is R38, Y71 and S85. The VH3 gH1 donor content is V24, M48, G49, T73 and V78. The VH4 gH1 donor content is M48, R71 and V78. SEQ ID NOs for the light chains shown, in order from top to bottom are SEQ ID NO: 30 ("342"), SEQ ID NO: 35 ("2 1 1 O12"), SEQ ID NO: 14 ("342 gL3") and SEQ ID NO: 2 ("342 gL4"). SEQ ID NOs for the heavy chains shown (VH3 grafts), in order from top to bottom, are SEQ ID NO: 29 ("342"), SEQ ID NO: 37 ("1-1 3-66"), SEQ ID NO: 10 ("342 gH7"), and SEQ ID NO: 1 ("342 gH1"). SEQ ID NOs for the heavy chains shown (VH4 grafts), in order from top to bottom, are SEQ ID NO: 29 ("342"), SEQ ID NO: 39 ("1-1 4-59"), a variant of SEQ ID NO: 9 ("VH4 gH6"), and a variant of SEQ ID NO: 11 ("VH4 gH1"). The SEQ ID NO: 9 and SEQ ID NO: 11 variants shown in FIG. 9 begin with amino acid "E" (instead of "Q" as in FIGS. 4 and 5, respectively) for expression in E. coli. Accordingly, the nucleotide sequences that correspond to these variant SEQ ID NOs: 9 and 11 differ from the nucleotide sequences set forth in SEQ ID NO: 19 and SEQ ID NO: 21 in that they begin with nucleotide "g" instead of "c".

FIG. 10 provides $V_L$ and $V_H$ amino acid and corresponding nucleotide sequences for anti-CD154 antibody 381. The CDR amino acid sequences are underlined.

FIG. 11 provides $V_L$ and $V_H$ amino acid and corresponding nucleotide sequences for anti-CD154 antibody 338. The CDR amino acid sequences are underlined.

FIG. 12 is a table listing rat anti-human CD154 antibodies isolated by Selected Lymphocyte Antibody Method (SLAM). The table provides $K_d$ and $IC_{50}$ values obtained with these antibodies in Biacore®, CD40 binding assays and ICAM-1 upregulation assays. Data obtained with antibody 342 are highlighted.

FIG. 13 provides the kappa light chain amino acid and corresponding nucleotide sequences of aglycosylated anti-CD154 antibody hu5c8 (hu5c8 aglyP-huIgG4).

FIG. 14 provides the heavy chain amino acid and corresponding nucleotide sequences of aglycosylated anti-CD154 antibody hu5c8 (hu5c8 aglyP-huIgG4). The mutations made to render the variant aglycosylated (S228P/T299A in Kabat EU nomenclature; residues 226 and 297) are shown underlined and in bold in the mature protein sequence.

FIG. 15 provides the kappa light chain amino acid and corresponding nucleotide sequences of aglycosylated anti-CD154 antibody hu342 (hu342 aglyP-huIgG4).

FIG. 16 provides the heavy chain amino acid and corresponding nucleotide sequences of aglycosylated anti-CD154 antibody hu342 (hu342 aglyP-huIgG4). The mutations made to render the variant aglycosylated (S228P/T299A in Kabat EU nomenclature; residues 226 and 297) are shown underlined and in bold in the mature protein sequence.

FIG. 18 is a table providing $K_d$ and $IC_{50}$ values obtained in Biacore®, CD40 binding assays, ICAM-1 upregulation assays and CD40L competition binding assays for different embodiments of the humanized 342 gL4gH1 antibody, including Fab' fragments and antibody-PEG conjugates.

FIG. 19 shows two graphs of the anti-TT (tetanus toxoid) IgG titer values as a function of time in cynomolgus monkeys receiving either a saline control or various doses of anti-CD154 antibodies. The top graph shows IgG titer values for days 0-20 after antibody treatment and TT challenge (the primary immune response), and the bottom graph shows values for days 30-50 after antibody treatment and a second TT challenge on day 30.

FIG. 20 is a graph of the anti-TT (tetanus toxoid) IgG titer values as a function of time in cynomolgus monkeys receiving various formats of anti-CD154 antibodies at a single dose (20 mg/kg for hu5c8, aglycosyl 5c8 and aglycosyl 342 and 40 mg/kg for 342 Fab'-PEG and 342 DFM-PEG). DFM-PEG is an antibody fragment in which two Fab' fragments are cross-linked with a PEGylated dimaleimide bridge.

FIG. 21 is a graph of the anti-TT (tetanus toxoid) IgM titer values as a function of time in cynomolgus monkeys receiving either a saline control or various doses of anti-CD154 antibodies. The graph shows IgM titer values for days 0-20 after challenge with TT (primary response).

FIG. 22 is a graph comparing the pharmacokinetics in cynomolgus monkeys of the 342 Fab'-PEG antibody and hu5c8 antibody.

FIG. 27 is a graph showing the results of a platelet aggregation assay described in Example 11 (Assay 2) performed with positive and negative control antibodies. The results demonstrate that platelet aggregation is specifically enhanced by complexes of the positive control anti-CD154 antibody and recombinant human soluble CD40L (sCD154).

FIG. 28 shows a sequence alignment of human (SEQ ID NO: 76) and mouse (SEQ ID NO: 77) soluble CD40L amino acid sequences. Differences between human and mouse sequences are indicated in red. The Hu5c8 epitope sequences are indicated in blue. Internal residues are marked with "|". Six regions (1-6) of the sequence where human residues were introduced into soluble mouse CD40L were selected.

FIGS. 29A-29D shows the results of a competition ELISA assay to demonstrate cross-blocking of 342 Fab' and hu5c8 Fab' (see Example 14). FIG. 29A shows the results of a titration of biotin 342 Fab' on CD154. A 1 nM concentration is on the linear part of the curve. FIG. 29B shows the results of a titration of biotin hu5c8 Fab' on CD154. A 0.3 nM concentration is on the linear part of the curve. FIG. 29C shows cross-blocking of biotin 342 and biotin 5c8 by unlabeled 342 Fab'. ch342 Fab is the chimeric 342 Fab'. FIG. 29D shows cross-blocking of biotin 342 by unlabeled 5c8 Fab'.

DETAILED DESCRIPTION OF THE INVENTION

Figure 17:
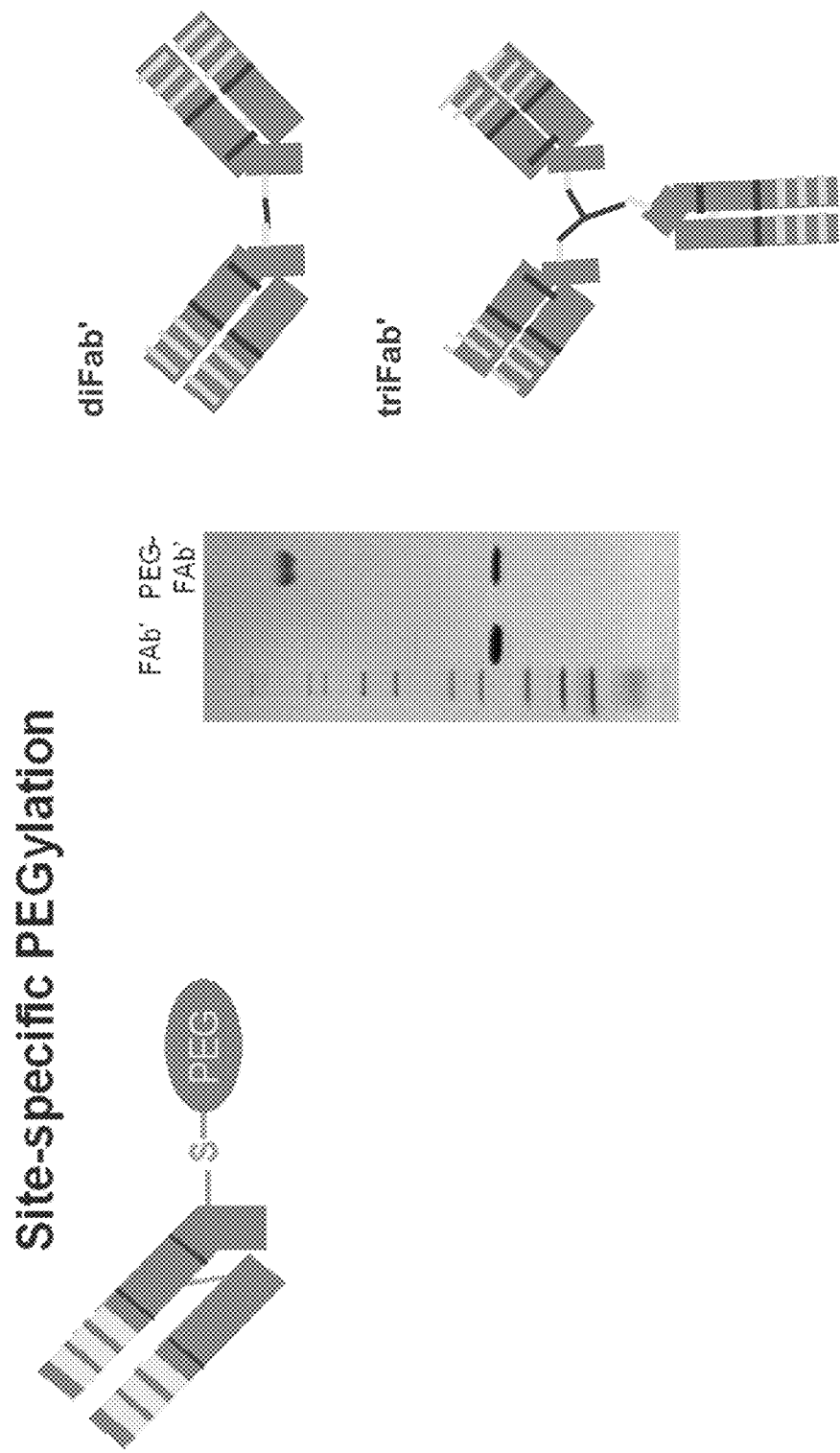
FIG. 17 shows exemplary Fab' fragments and a gel showing the site-specific PEGylation of an Fab' fragment of an anti-CD154 antibody. The Fab' was pegylated by reacting PEG-maleimide with a single cysteine residue at the hinge.

In order that the invention herein described may be more fully understood, the following detailed description is set forth. Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art.

Throughout this application, various patents, publications and references are referred to. Disclosures of these patents, publications and references are hereby incorporated by reference into this application in their entireties.

Standard reference works setting forth the general principles of recombinant DNA technology known to those of skill in the art include Ausubel et al., *Current Protocols In Molecular Biology*, John Wiley & Sons, New York (1998 and Supplements to 2001); Sambrook et al., *Molecular Cloning: A Laboratory Manual*, 2d Ed., Cold Spring Harbor Laboratory Press, Plainview, N.Y. (1989); Kaufman et al., Eds., *Handbook Of Molecular And Cellular Methods In Biology And Medicine*, CRC Press, Boca Raton (1995); McPherson, Ed., *Directed Mutagenesis: A Practical Approach*, IRL Press, Oxford (1991).

Standard reference works setting forth the general principles of immunology known to those of skill in the art include: Harlow and Lane, *Antibodies: A Laboratory Manual*, 2d Ed., Cold Spring Harbor Laboratory Press, Cold Spring Harbor, N.Y. (1999); and Roitt et al., *Immunology*, 3d Ed., Mosby-Year Book Europe Limited, London (1993).

Standard reference works setting forth the general principles of medical physiology and pharmacology known to those of skill in the art include: Fauci et al., Eds., *Harrison's Principles Of Internal Medicine*, 14th Ed., McGraw-Hill Companies, Inc. (1998).

DEFINITIONS

As used herein, the term "CD154 binding protein" includes any molecule, including an antibody, that specifically binds to or antagonizes CD154. Thus, as used herein, an anti-CD154 antibody is one class of CD154 specific binding proteins. A CD154 binding protein of the invention may comprise at least one, preferably two, three or more CDRs as disclosed herein. A CD154 binding protein or other such CD154 antagonist may encompass species that are not classic antibody fragments or derivatives but which nonetheless comprise amino acid sequences and/or chemical structures that confer CD154 epitope binding specificity. Such CD154 antagonists may be made, e.g., from alternative scaffolds (see, for example, Binz et al. 2005 *Nat Biotech* 23: 1257-1268 and Hosse et al. 2006 *Protein Science* 15: 14-27). Such a CD154 binding protein or antagonist may be fused to an antibody Fc region that is functionally deficient or to a heterologous functional moiety as described herein to improve the half-life and/or other in vivo properties of the CD154 binding protein.

The CD154 binding proteins may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable domain, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See e.g., Nygren and Uhlen, 1997, *Current Opinion in Structural Biology*, 7, 463-469).

The term "antibody" as it is used herein with respect to the invention, includes an isolated, recombinant or synthetic antibody, antibody conjugate or antibody derivative. The term "antibody" is often intended to include an antibody fragment, including an antigen-binding fragment, unless otherwise indicated or understood by context. An antigen-binding fragment competes with the intact antibody for specific binding. See generally, *Fundamental Immunology*, Ch. 7 (Paul, W., ed., 2nd ed. Raven Press, N.Y. (1989)). Antigen-binding fragments may be produced by recombinant DNA techniques or by enzymatic or chemical cleavage of intact antibodies. In some embodiments, antigen-binding fragments include Fab, $F(ab)_2$, Fab', $F(ab')_2$, $F(ab')_3$, Fd, Fv, domain antibodies (dAb), other monovalent and divalent fragments, complementarity determining region (CDR) fragments, single-chain antibodies (e.g., scFv, scFab, and scFabΔC), chimeric antibodies, diabodies, triabodies, minibodies, nanobodies, and polypeptides that contain at least a portion of an antibody that is sufficient to confer specific antigen binding to the polypeptide; and fusions and derivatives of the foregoing. See, e.g., Holliger and Hudson, *Nature Biotechnology* 23: 1126-1136 (2005) and Hust et al., *BMC Biotech* 7: 14 (2007).

An "Fd fragment" is an antibody fragment that consists of the $V_H$ and $C_{H1}$ domains; an "Fv fragment" consists of the $V_L$ and $V_H$ domains of a single arm of an antibody; an "scFv fragment" is a single chain antibody comprising a heavy chain variable region ($V_H$) and a light chain variable region ($V_L$) joined by a peptide linker; an "scFab fragment" is a single chain antibody comprising a fragment difficult (Fd) joined to a light chain by a peptide linker; an "scFabΔC" fragment is a scFab variant without cysteine (see, e.g., Hust et al., supra); and a "dAb fragment" (single domain antibody) comprises a single variable domain (e.g., a $V_H$ or a $V_L$ domain) (Ward et al., *Nature* 341:544-546 (1989)). Further, diabodies and triabodies are also included. Diabodies and triabodies of the present invention include, for example, homodimeric and heterodimeric diabodies and triabodies. For example, in certain embodiments, the variable domains making up a triabody may bind to three different epitopes or to identical epitopes.

Unless otherwise stated or where otherwise implied by context, an "antibody" of the present invention includes whole antibodies and any antigen-binding fragments thereof, antibody derivatives or variants that may contain one or more modifications (e.g., an amino acid insertion, deletion, substitution, a post-translational modification or lack thereof, etc.), including antibody conjugates (i.e., antibody or antigen-binding fragment thereof conjugated to or associated with a functional moiety). The antibody derivatives, including antibody conjugates, may be based on or may comprise an antigen-binding fragment of the invention that specifically binds CD154. Additionally, the aforementioned antibody embodiments may be murine, hamster, goat, rabbit, chimeric, humanized, or fully human antibodies, fragments, derivatives, or conjugates. It is understood that in certain aspects of the invention, the term "antibody" may exclude one or more of the antibody embodiments recited above; such conditions will be evident to the skilled artisan.

The term "pegylation," "polyethylene glycol" or "PEG" includes a polyalkylene glycol compound or a derivative thereof, with or without coupling agents or derivatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin and other affinity reagent derivatives.

The term "effector function" refers to the functional ability of the Fc or constant region of an antibody to bind proteins and/or cells of the immune system. Antibodies having reduced effector function and methods for engineering such antibodies are well-known in the art (see, e.g., WO 05/18572, WO 05/03175, and U.S. Pat. No. 6,242,195) and are described in further detail herein. Typical effector functions include the ability to bind complement protein (e.g., the complement protein C1q), and/or an Fc receptor (FcR) (e.g., FcγRI, FcγRII, FcγRIIa, FcγRIII, and/or FcγRIIIb). The functional consequences of being able to bind one or more of the foregoing molecules include, without limitation, opsonization, phagocytosis, antigen-dependent cellular cytotoxicity (ADCC), complement-dependent cytotoxicity (CDC) and/or effector cell modulation. A decrease in effector function refers to a decrease in one or more of the biochemical or cellular activities induced at least in part by binding of Fc to its cognate receptor or to a complement protein or effector cell, while maintaining the antigen-binding activity of the variable region of the antibody (or fragment thereof), albeit with reduced, similar, identical, or increased binding affinity. Particular antibodies of the invention exhibit reduced effector function. Decreases in effector function, e.g., Fc binding to an Fc receptor or complement protein, can be expressed in terms of fold reduction (e.g., reduced by 1.5-fold, 2-fold, and the like) and may be calculated based on, e.g., the percent reductions in binding activity determined using binding assays known in the art (see, for example, WO 05/18572).

Unless otherwise required by context, singular terms shall include pluralities and plural terms shall include the singular.

Throughout this specification and claims, the word "comprise," or variations such as "comprises" or "comprising" will be understood to imply the inclusion of a stated integer or group of integers but not the exclusion of any other integer or group of integers.

CD154

CD154 is known by several other names in the art, such as CD40 ligand (CD40L), CD40 counter receptor (CD40CR), gp39, T-BAM, T-Cell Activating Molecule, TRAF, TNF-Related Activation Protein (TRAP), and Tumor Necrosis Factor Ligand Superfamily Member 5 (TNFSF5) (Gauchat et al., 1993 *FEBS Lett.* 315: 259-266; Graf et al. 1992, *Europ. J. Immun.* 22: 3191-3194; Hollenbaugh et al., 1992 *EMBO J.* 11: 4313-4321). These terms are used interchangeably throughout this application. The CD154 binding proteins, including antibodies, of this invention specifically bind to human CD154 and may cross react and therefore specifically bind to CD154 of other species. In certain embodiments, the CD154 binding proteins, including antibodies, of this invention specifically bind to human CD154, mouse CD154 or non-human primate CD154.

Anti-CD154 Antibodies and CD154 Binding Proteins

The term "anti-CD154 antibody" as used herein refers to an immunoglobulin molecule that is able to bind specifically to an epitope on a CD154 antigen. Anti-CD154 antibodies may be intact immunoglobulins derived from natural sources or from recombinant sources and may be immunoreactive portions of intact immunoglobulins. Antibodies are typically tetramers of immunoglobulin molecules.

Accordingly, as referred to in all of the embodiments and methods of this invention an "anti-CD154 antibody" encompasses (unless where otherwise indicated or where otherwise suggested by context) a monoclonal antibody, a polyclonal antibody, a murine antibody, hamster antibody, goat antibody, rabbit antibody, a chimeric antibody, a primatized antibody, a humanized antibody, a (fully) human antibody, a multimeric antibody, a heterodimeric antibody, a hemidimeric antibody, a bi-, tri-, or tetravalent antibody, a bispecific antibody, a single chain antibody (e.g., scFv, scFab, and scFabΔC), Bis-scFv, a diabody, triabody or tetrabody, single domain antibodies, and modified Fab fragments. In certain embodiments, the anti-CD154 antibody is an antibody comprising only a single variable immunoglobulin domain. Accordingly, monovalent antibodies include antibodies that comprise only one immunoglobulin variable domain (i.e., a single light or heavy variable chain) and that specifically bind to CD154. In addition, anti-CD154 antibodies of the invention may be monovalent, divalent, or multivalent for CD154.

In certain embodiments, a CD154 binding protein, e.g., an anti-CD154 antibody, with reduced effector function comprises any portion of an anti-CD154 antibody that is sufficient to maintain specific binding to the CD154 antigen. For example, the antibody may comprise only a single variable immunoglobulin domain—a $V_H$ or $V_L$ domain.

Accordingly, in certain embodiments, a CD154 binding protein, e.g., an anti-CD154 antibody, is an antibody fragment. Antibody fragments include, for example, an Fab fragment, an $F(ab)_2$ fragment, an Fab' fragment, an $F(ab')_2$ fragment, an $F(ab')_3$ fragment, a single chain F(v) fragment or an F(v) fragment and epitope-binding fragments of any of the above (see for example Holliger and Hudson, 2005, *Nature Biotech.* 23(9):1126-1136). Antibody fragments of the invention are described in more detail below.

In one example, the CD154 binding proteins or anti-CD154 antibodies are antibodies (e.g., antibodies of the IgG4 subtype) or fragments (e.g., Fab' fragments) which possess a native or a modified hinge region. A number of modified hinge regions have been described, for example, in U.S. Pat. No. 5,677,425, WO 99/15549, and WO 98/25971. In another example, the antibodies of the invention are modified in their constant regions as those antibodies described in WO 05/003169, WO 05/003170 and WO 05/003171. Any of the aforementioned anti-CD154 antibodies, antibody derivatives or antibody fragments may be used to form antibody conjugates of the present invention. Any of the above antibodies, fragments, and conjugates may elicit reduced effector function compared to a second anti-CD154 antibody.

The antibody molecules of the invention can be of any class (e.g. IgG, IgE, IgM, IgD or IgA) or subclass of immunoglobulin molecule. The constant region domains of the antibody, if present, may be selected having regard to the proposed function of the antibody molecule. For example, the constant region domains may be human IgA, IgD, IgE, IgG or IgM domains. In particular, human IgG constant region domains may be used, especially IgG1, IgG2, IgG3, and IgG4. IgG2 and IgG4 isotypes may be used in certain embodiments where the antibody molecule is intended for therapeutic uses for which reduced or eliminated antibody effector functions are desired. Alternatively, IgG1 and IgG3 isotypes may be used when the antibody molecule is intended for therapeutic purposes for which antibody effector functions are required.

In some embodiments, one or more of the CDRs of a CD154 binding protein, e.g., antibody, of the invention may be incorporated into one or more immunoglobulin domains, universal frameworks, protein scaffolds or other biocompatible framework structures based on protein scaffolds or skeletons other than immunoglobulin domains (Nygren & Uhlén, 1997, *Curr. Opin. Strural Biol.* 7:463-469; Saragovi et al, 1992, *Bio/Technology* 10:773-779; Skerra, 2000, *J. Mol. Recognition.* 13:167-187). In certain embodiments, the CDRs of an anti-CD154 antibody are incorporated into a universal framework (i.e., a framework which can be used to create the full variability of functions, specificities, or properties which are originally sustained by a large collection of different frameworks, see U.S. Pat. No. 6,300,064). In other embodiments, alternative scaffolds (see, for example, Binz et al. 2005 *Nat Biotech* 23: 1257-1268 and Hosse et al. 2006 *Protein Science* 15: 14-27) may be used to create CD154 binding proteins of the invention.

The term "anti-CD154 antibody" also encompasses a synthetic antibody or a recombinant antibody that is generated using recombinant DNA technology, such as, for example, an antibody expressed by a bacteriophage. The term "anti-CD154 antibody" should also be construed to include an antibody that has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology that is available and well known in the art.

In one embodiment, the invention provides an "anti-CD154 antibody" that is a monoclonal antibody. A monoclonal antibody refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma (murine or human) method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example. It is also understood that certain embodiments of the present invention relate to compositions comprising one or more different monoclonal antibodies that specifically bind CD154, i.e., a polyclonal antibody composition comprising a plurality of monoclonal antibodies with different epitope specificities.

In another embodiment of the invention, an "anti-CD154 antibody" refers to an antibody that is a chimeric antibody, or an antibody derivative or conjugate or antigen-binding fragment thereof. Typically, chimeric antibodies include the heavy and/or light chain variable regions, including both CDR and framework residues, of one species (typically mouse) fused to constant regions of another species (typically human). These chimeric mouse/human antibodies contain approximately 75% human and 25% mouse amino acid sequences. The human sequences represent the constant regions of the antibody, while the mouse sequences represent the variable regions (and thus contain the antigen-binding sites) of the antibody.

In another embodiment, the CD154 binding proteins, anti-CD154 antibodies of this invention include antibodies, antibody derivatives and antigen-binding fragments comprising a variable domain comprising framework regions from one antibody and CDR regions from another antibody.

In a more specific embodiment, the CD154 binding proteins and anti-CD154 antibodies of this invention include chimeric antibodies comprising framework regions and CDR regions from different human antibodies.

Methods of making all of the chimeric antibodies described above are well known to one of skill in the art. See, e.g., U.S. Pat. No. 5,807,715; Morrison et al. (1984) *Proc. Natl. Acad. Sci. USA* 81(21):6851-5; Sharon et al. (1984) *Nature* 309(5966):364-7; Takeda et al. (1985) *Nature* 314 (6010):452-4.

In certain embodiments of the present invention, an anti-CD154 antibody, that binds CD154 is generated by Selected Lymphocyte Antibody Method (SLAM) (Babcook et al., 1996, *Proc. Natl. Acad. Sci,* 93, 7843-7848; WO 92/02551; de Wildt et al., 1997, *J. Immunol. Methods,* 207:61-67 and in Lagerkvist et al., 1995, *BioTechniques* 18:862-869) which enables the isolation from any species of cells producing high affinity antibodies during in vivo immune responses. Other techniques include those described by de Wildt et al., 1997, *J. Immunol. Methods,* 207:61-67 and Lagerkvist et al., 1995, *BioTechniques* 18(5):862-869. The above methods rely on the isolation of individual antibody-producing cells which are then clonally expanded followed by screening for those clones which produce anti-CD154 antibodies followed by the subsequent identification of the sequence of their variable heavy ($V_H$) and light ($V_L$) chain genes. A particular screening method is detailed in WO 04/051268. Thus, B cells that are positive for antibodies to CD154 are isolated. The B cells may be from human, mouse, rat, hamster, rabbit, goat, or other mammalian species. The antibody genes in these B cells may be cloned and expressed in a host cell, e.g., by conventional recombinant DNA technology. In certain embodiments, the host cell is *E. coli*. Other host cells are detailed below. The antibodies (which include antibody fragments such as Fab' fragments) expressed in these cells may be purified by conventional means. If the antibodies are from a non-human source, they may be humanized by conventional methods, such as by mutagenesis of their genes. The humanized antibodies may be subsequently expressed in a host cell and may be purified.

Monoclonal antibodies may be prepared by any method known in the art such as the hybridoma technique (Kohler & Milstein, *Nature,* 1975, 256:495-497), the trioma technique, the human B-cell hybridoma technique (Kozbor et al., *Immunology Today,* 1983, 4, 72) and the EBV-hybridoma technique (Cole et al., "Monoclonal Antibodies and Cancer Therapy", pp. 77-96, Alan R. Liss, Inc., 1985). The methods for creating and manufacturing recombinant antibodies are well known in the art (see for example, U.S. Pat. No. 4,816,397; U.S. Pat. No. 6,331,415; Simmons et al., 2002, *Journal of Immunological Methods,* 263, 133-147; WO 92/02551; Orlandi et al., 1989, *Proc. Natl. Acad. Sci. USA,* 86, 3833; Riechmann et al., 1988, Nature, 322, 323; U.S. Pat. No. 5,585,089; WO91/09967; Mountain and Adair, 1992, *Biotechnol. Genet. Eng. Rev,* 10, 1-142; Verma et al., 1998, *J. Immunol. Methods,* 216:165-181; Holliger and Hudson, 2005, Nature Biotech. 23(9):1126-1136).

Antibodies of the present invention may also be generated using various phage display methods known in the art and include those disclosed by Brinkman et al., 1995, *J. Immunol. Methods,* 182:41-50; Ames et al., 1995, *J. Immunol. Methods,* 184, 177-186; Kettleborough et al. 1994, *Eur. J. Immunol.,* 24, 952-958; Persic et al., 1997, *Gene,* 187, 9-18; and Burton et al., 1994, *Advances in Immunol.,* 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

Also, transgenic (e.g., genetically engineered) mice, or other organisms, including other mammals, may be used to produce binding proteins and antibodies of this invention (see for example U.S. Pat. No. 6,300,129). For example, it is known that mice engineered to replace only the variable regions of mouse immune loci (heavy chain V, D, and J segments, and light chain V and J segments) with corresponding human variable sequences can be used to produce large quantities of high affinity antibodies with human variable sequences (see, e.g., U.S. Pat. No. 6,586,251; U.S. Pat. No. 6,596,541, and U.S. Pat. No. 7,105,348).

In another embodiment of this invention, an "anti-CD154 antibody" refers to an antibody, antibody derivative or conjugate, or antigen-binding fragment that is primatized or humanized. Primatized and humanized antibodies typically include heavy and/or light chain CDRs from a murine antibody grafted into a non-human primate or human antibody V region framework, usually further comprising a human constant region. See, e.g., Riechmann et al. (1988) *Nature* 332: 323-327; U.S. Pat. Nos. 6,054,297; 5,821,337; 5,770,196; 5,766,886; 5,821,123; 5,869,619; 6,180,377; 6,013,256; 5,693,761; and 6,180,370.

The rationale for using such primatized or humanized antibodies is to retain the (human) antigen specificity of the mouse antibody conferred by mouse CDRs but to reduce the immunogenicity of the mouse antibody (a mouse antibody would cause an immune response against it in species other than the mouse) by using as much human framework sequence as possible. Such antibodies may be used in human therapies for minimizing or eliminating unwanted side effects, such as immune responses. Antibodies comprising donor CDRs grafted from antigen-specific non-human antibodies onto homologous non-human primate acceptor frameworks having reduced immunogenicity in humans have been described (US 2005/0208625; US 2002/0062009; U.S. Pat. No. 7,338,658)

Accordingly, humanized forms of non-human (e.g. murine) antibodies are specific chimeric immunoglobulins, immunoglobulin chains or fragments thereof (such as Fv, Fab, Fab', $F(ab')_2$ or other antigen-binding subsequences of antibodies) that contain sequences derived from non-human immunoglobulin and human immunoglobulin sequences. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues.

Furthermore, the humanized antibody may comprise residues which are found neither in the recipient antibody nor in the imported CDR or FR sequences. These modifications are made to further refine and optimize antibody performance. In general, the humanized antibody may comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optionally may also comprise at least a portion of an immunoglobulin constant region (Fc), typically that of a human immunoglobulin.

A humanized antibody (which includes, e.g., antibody fragments, and antibody derivatives or conjugates) may be produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, non-human antibody. Methods for making humanized antibodies are well known to those of skill in the art of antibodies. See, e.g., EP 239400; Jones et al. (1986) *Nature* 321:522-525; Riechmann et al. (1988) *Nature* 332:323-327; Verhoeyen et al. (1988) *Science* 239:1534-1536; Queen et al. (1989) *Proc. Nat. Acad. Sci. USA* 86:10029; Orlandi et al. (1989) *Proc. Natl. Acad. Sci. USA* 86:3833; U.S. Pat. No. 6,180,370, and EP 519596, which describes antibody veneering of surface residues.

Accordingly, in one embodiment of this invention, an anti-CD154 antibody refers to a humanized antibody (which includes without limitation a humanized antigen-binding fragment and a humanized antibody derivative or a conjugate), that is generated by the transplantation of murine or rat (or other non-human) CDRs onto a human antibody. More specifically, this humanization is achieved as follows: (1) the cDNAs encoding heavy and light chain variable domains are isolated from a hybridoma or a B cell that secretes the antibody; (2) the DNA sequences of the variable domains, including the CDRs, are determined by sequencing; (3) the DNAs encoding the CDRs are transferred to the corresponding regions of a human antibody heavy or light chain variable domain coding sequence by site directed mutagenesis; and (4) the human constant region gene segments of a desired isotype (e.g., 1 for CH and k for CL) are added. Finally, the humanized heavy and light chain genes are co-expressed in mammalian host cells (e.g., CHO or NS0 cells) to produce soluble humanized antibody.

At times, direct transfer of CDRs to a human framework leads to a loss of antigen-binding affinity of the resultant binding protein or antibody. Loss of antigen-binding affinity may occur because in some cognate antibodies, certain amino acids within the framework regions interact with the CDRs and thus influence the overall antigen binding affinity of the antibody. In such cases, the skilled worker will appreciate that it would be critical to introduce "back mutations" in the framework regions of the acceptor antibody in order to retain the antigen-binding activity of the cognate antibody. The general approaches of making back mutations are well known to those of skill in the art. See, e.g., Queen et al. (1989) *Proc. Nat. Acad. Sci. USA* 86:10029; Co et al. 1991. *Proc. Nat. Acad. Sci. USA* 88:2869-2873; WO 90/07861; Tempest 1991. *Biotechnology* 9: 266-271. Exemplary back mutations for antibodies of the present invention include those residues depicted in FIG. 9 under donor content.

In certain embodiments the binding protein or antibody of the present invention may comprise a $V_H$ domain that is not a camelid or murine immunoglobulin variable domain. In certain embodiments, the antibody polypeptide may comprise a $V_H$ domain that does not contain one or more amino acids that are specific to camelid immunoglobulin variable domains as compared to human $V_H$ domains.

In one embodiment of this invention, an "anti-CD154 antibody" refers to an antibody (which includes an antigen-binding fragment and an antibody derivative or conjugate) that is fully human. A fully "human" antibody comprises an antibody polypeptide or an immunoglobulin variable domain that has a sequence derived from a human immunoglobulin (e.g., obtained from a human immunoglobulin coding sequence). The term "human antibody" includes, for example, antibodies having variable and constant regions (if present) derived from human germline immunoglobulin sequences. The term "human" as applied herein to an antibody or to a fragment such as a variable domain does not encompass an antibody from another species, e.g., mouse, that has been "humanized" through grafting of human constant region sequences onto an antibody polypeptide (i.e., replacing non-human constant regions with human constant regions) or through grafting of human V region framework sequences onto an immunoglobulin variable domain from a non-human mammal (i.e., replacing non-human framework regions of a V domain with human framework regions). Methods of humanizing immunoglobulin variable regions through rational modification of complementarity determining residues have been described (US 2006/0258852).

Human antibodies may, in certain embodiments, include amino acid residues not encoded by human germline immunoglobulin sequences (e.g., mutations introduced by random or site-specific mutagenesis in vitro or by somatic mutation in vivo). In certain embodiments therefore, the present invention relates to an anti-CD154 antibody comprising a variable domain having one or more framework regions (e.g., FW1, FW2, FW3, and/or FW4) comprising an amino acid sequence that is the same as the amino acid sequence of a corresponding framework region encoded by a human germline antibody gene segment, or the amino acid sequences of one or more of said framework regions collectively comprising up to 5 amino acid differences relative to the amino acid sequence of said corresponding framework region encoded by a human germline antibody gene segment. In further embodiments, the amino acid sequences of the framework regions (FW1, FW2, FW3, and FW4) of a variable domain are the same as the amino acid sequences of corresponding framework regions encoded by a human germline antibody gene segment, or the sequences of FW1, FW2, FW3, and FW4 collectively contain up to 10 amino acid differences relative to the sequences of the corresponding framework regions encoded by the human germline antibody gene segment. Exemplary germline antibody gene segments include, for example, DP47, DP45, DP48, and DPK9 (US 2006/0062784), and segments encoding the acceptor framework sequences described in the Examples and Figures.

In some embodiments, a human antibody (which includes an antibody fragment or variable domain sequence) has at least 85% amino acid sequence identity (including, for example, 87%, 90%, 93%, 95%, 97%, 99% or higher sequence identity) to a naturally-occurring human antibody.

Fully human or human antibodies may be derived from transgenic (e.g., genetically engineered such as knock-in) mice carrying human antibody genes (carrying the variable (V), diversity (D), joining (J), and constant (C) exons) or human V, D and J regions from human cells. For example, it is now possible to produce genetically engineered animals (e.g., mice) that are capable, upon immunization, of producing a full repertoire of human antibodies in the absence of endogenous immunoglobulin production (see, e.g., Jakobovits et al., *PNAS*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). A transgenic (e.g., genetically engineered including knock-out, knock-in, gene replacement and the like) mouse strain may be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The genetically engineered mice may be immunized with the target protein (e.g., CD154, fragments thereof, or cells expressing CD154) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they may be assembled and displayed on the outer surface of a display package containing the vector. For example, antibody chains may be expressed as fusion proteins with a phage coat protein from the outer surface of the phage. Thereafter, display packages may be screened for display of antibodies binding to a target.

In addition, human antibodies may be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996), U.S. Pat. No. 6,300,064). Synthetic phage libraries may be created which use randomized combinations of synthetic human antibody V-regions. Selection of antigen fully human antibodies may be made in which the V-regions are very human-like in nature. See U.S. Pat. Nos. 6,794,132, 6,680,209, 4,634,666, and Ostberg et al. (1983), *Hybridoma* 2:361-367.

For the generation of human antibodies, also see Mendez et al. *Nature Genetics* 15:146-156 (1997), Green and Jakobovits *J. Exp. Med.* 188:483-495 (1998). Human antibodies are further discussed and delineated in U.S. Pat. Nos. 5,939,598 and 6,673,986. Also see U.S. Pat. Nos. 6,114,598, 6,075,181, and 6,162,963. Also see U.S. Pat. No. 6,150,584, U.S. Pat. No. 6,713,610, U.S. Pat. No. 6,657,103, US 2003/0229905 A1, US 2004/0010810 US 2004/0093622 A1, US 2006/0040363 A1, US 2005/0054055 A1, US 2005/0076395 A1 and US 2005/0287630 A1. See also EP 0463151 B1, WO 94/02602, WO 96/34096, and WO 98/24893.

In an alternative approach, others have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in, e.g., U.S. Pat. Nos. 5,545,807, 5,545,806, 5,625,825, 5,625,126, 5,633,425, 5,661,016, 5,770,429, 5,789,650, 5,814,318, 5,591,669, 5,612,205, 5,721,367, 5,789,215, and 5,643,763. Also see U.S. Pat. Nos. 5,569,825, 5,877,397, 6,300,129, 5,874,299, 6,255,458, and 7,041,871, the disclosures of which are hereby incorporated by reference in their entirety. See also EP 0546073, WO 92/03918, WO 92/22645, WO 92/22647, WO 92/22670, WO 93/12227, WO 94/00569, WO 94/25585, WO 96/14436, WO 97/13852, and WO 98/24884. See further Taylor et al. (1992 *Nuc. Acids. Res.*, 20: 6287), Chen et al. (1993 *Int. Immunol.* 5: 647), Tuaillon et al. (1993 *PNAS USA*. 90: 3720-4), Choi et al., (1993 *Nature Genetics* 4: 117), Lonberg et al. (1994 *Nature* 368: 856-859), Taylor et al. (1994 *International Immunology* 6: 579-591), and Tuaillon et al. (1995 *J Immunol.* 154: 6453-65), Fishwild et al. (1996 *Nature Biotechnology* 14: 845), and Tuaillon et al. (2000 *Eur J Immunol.* 10: 2998-3005).

In a more particular embodiment of this invention, the fully human antibodies are prepared using in vitro-primed human splenocytes (Boerner et al. 1991. *J. Immunol.* 147:86-95).

In a more particular embodiment of this invention, the fully human antibodies are prepared by repertoire cloning (Persson et al. 1991. *Proc. Nat. Acad. Sci. USA* 88: 2432-2436; Huang and Stollar 1991. *J. Immunol. Methods* 141: 227-236). In addition, U.S. Pat. No. 5,798,230 describes preparation of human monoclonal antibodies from human B cells, wherein human antibody-producing B cells are immortalized by infection with an Epstein-Barr virus, or a derivative thereof, that expresses Epstein-Barr virus nuclear antigen 2 ("EBNA2"), a protein required for immortalization. The EBNA2 function is subsequently shut off, resulting in an increase in antibody production.

Other methods for producing fully human antibodies involve the use of non-human animals that have inactivated endogenous Ig loci and are transgenic for un-rearranged human antibody heavy chain and light chain genes. Such transgenic animals can be immunized with activated T cells or the D1.1 protein (U.S. Pat. Nos. 5,474,771; 6,331,433; and 6,455,044) and hybridomas can be generated from B cells derived therefrom. The details of these methods are described in the art. See, e.g. various publications/patents concerning transgenic mice containing human Ig miniloci, including U.S. Pat. No. 5,789,650; the various publications/patents with respect to XENOMOUSE® mice, including U.S. Pat. Nos. 6,075,181; 6,150,584; and 6,162,963; Green, 1997, *Nature Genetics* 7: 13-21; Mendez, 1997, *Nature Genetics* 15: 146-56; and the various publications/patents concerning "transomic" mice, including EP 843961 and Tomizuka, 1997, *Nature Genetics* 16: 1433-43.

CD154 binding proteins and anti-CD154 antibodies of the present invention also relate to cross-blocking binding proteins or antibodies, or to binding proteins or antibodies that bind to the same epitope or that bind to a closely related or overlapping epitope as any of the antibodies described herein. A cross-blocking binding protein or antibody can competitively inhibit or block binding of any of the antibodies described herein. In certain embodiments, the invention provides CD154 binding proteins and anti-CD154 antibodies that bind to the same epitope as does a humanized antibody comprising a heavy chain sequence according to SEQ ID NO. 12 or SEQ ID NO. 13 and comprising a light chain sequence according to SEQ ID NO. 15 (342 Fab and Fab' fragments), and which exhibit similar CD154 binding properties in competition assays with anti-CD154 antibody 5c8, as described herein. In other embodiments, the invention provides CD154 binding proteins and anti-CD154 antibodies that bind to the same epitope as does a humanized antibody comprising a $V_L$ domain sequence according to SEQ ID NO. 58 and a $V_H$ domain sequence according to SEQ ID NO. 60 (338 antibody variable sequences), and which exhibit similar CD154 binding properties in competition assays with anti-CD154 antibody 5c8, as described herein.

In certain embodiments of the present invention, a CD154 binding protein, e.g. an anti-CD154 antibody, exhibits high affinity for human CD154. For example in certain embodiments, a CD154 binding protein dissociates from human CD154 (human CD40L) with a $K_D$ in the range of 50 nM to 1 pM, inclusive, as determined by surface plasmon resonance (e.g., Biacore®). For example, the $K_D$ for human CD154 may be 25 nM to 1 pM, 10 nM to 1 pM, 5 nm to 1 pM, 1 nM to 1 pM, 0.5 nM to 1 pM, 0.1 nM to 1 pM, 75 pM to 1 pM, 50 pM to 1 pM, 20 pm to 1 pm, or even 10 pm to 1 pm. In other embodiments, a CD154 binding protein of the present invention dissociates from human CD154 with a $K_D$ in the range of 500 pM to 1 pM, inclusive, as determined by surface plasmon resonance (e.g., Biacore®). In some embodiments, the $K_D$ for human CD154 is less than 50 pM. For example, in some of the embodiments of the present invention, a CD154 binding protein dissociates from human CD154 with a $K_D$ that is less than 20 pM. In some of the embodiments of the present invention, a CD154 binding protein dissociates from human CD154 with a $K_D$ that is less than 10 pM. In certain embodiments, a CD154 binding protein of the invention binds to CD154 with high affinity but does not displace bound CD154 from CD40. Antibody affinity may be enhanced by methods known in the art (see, e.g., Clark et al. 2006 *Protein Sci.* 15(5): 949-60, which describes affinity enhancement of an antibody using structure-based computational design, and Chao et al. 2006 *Nat Protoc* 1: 755-768, which describes methods of isolating and engineering scFvs with desired properties using yeast surface display).

Where it is desired to improve the affinity of antibodies of the invention containing one or more of the above-mentioned CDRs, such antibodies with improved affinity may be obtained by a number of affinity maturation protocols, including but not limited to maintaining the CDRs (Yang et al., *J. Mol. Biol.*, 254, 392-403, 1995), chain shuffling (Marks et al., *Bio/Technology*, 10, 779-783, 1992), use of mutation strains of *E. coli*. (Low et al., *J. Mol. Biol.*, 250, 350-368, 1996), DNA shuffling (Patten et al., *Curr. Opin. Biotechnol.*, 8, 724-733, 1997), phage display (Thompson et al., *J. Mol. Biol.*, 256, 7-88, 1996) and sexual PCR (Crameri, et al., *Nature*, 391, 288-291, 1998). All of these methods of affinity maturation are discussed by Vaughan et al. (*Nature Biotechnology*, 16, 535-539, 1998). Thus, the invention also provides sequence variants of the antibodies of the invention which bind specifically to CD154. Such sequence variants comprise one or more semi-conservative or conservative substitutions within their sequence and such substitutions preferably do not significantly affect the desired activity of the polypeptide. Substitutions may be naturally occurring or may be introduced for example using mutagenesis (e.g. Hutchinson et al., 1978, *J. Biol. Chem.* 253:6551). The amino acids glycine, alanine, valine, leucine and isoleucine, for example, can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic). Other amino acids which may often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

The binding affinity of CD154 binding proteins, e.g., anti-CD154 antibodies, of the present invention may also be described in relative terms or as compared to the binding affinity of a second antibody that also specifically binds to CD154 (e.g., a second anti-CD154 antibody that is CD154-specific, which may be referred to herein as a "second CD154-specific antibody". In some embodiments, the second CD154-specific antibody may be antibody 5c8 (produced by the hybridoma deposited with ATCC under Accession No. HB 10916, as described in U.S. Pat. No. 5,474,771) or humanized 5c8). In other embodiments, the second CD154-specific antibody may be any of the antibodies of the invention, such as 342, 381, 338, 294, 295, 300, 335, 303 or 402 (FIG. 12). Accordingly, certain embodiments of the present invention relate to an anti-CD154 antibody that binds to human CD154 with greater affinity than antibody 5c8, or with a $K_D$ that is lower than the $K_D$ of antibody 5c8. In certain embodiments, an anti-CD154 antibody of the present invention also inhibits CD154 activity or blocks the CD154:CD40 interaction to a greater degree than does a second CD154-specific antibody, such as 5c8, at equimolar concentrations. The relative ability of an anti-CD154 antibody to block the CD154:CD40 interaction may be measured by any available assay, such as, e.g., the ICAM-1 upregulation assay described herein and competition binding assays.

Accordingly, in certain embodiments, CD154 binding proteins and anti-CD154 antibodies (including antibody fragments and derivatives) of the invention are useful for inhibiting binding of CD154 to CD40 and do so with high specificity, e.g., with an IC50 in the range of 10 pM to 1.5 μM, inclusive. In certain embodiments, the CD154 binding proteins, e.g., antibodies, of the invention may have an IC50 in the range of 10 pm to 500 pm, 50 pm to 500 pm, 100 pm to 500 pm, 250 pm to 750 pm, 500 pm to 1 μM or 750 pm to 1.5 μM. In further embodiments, the anti-CD154 antibody does not substantially agonize CD40 activity or activate CD40 signaling. In some embodiments, an anti-CD154 antibody of the present invention antagonizes an activity of CD154 or CD40 or both.

Certain embodiments of the present invention, therefore, relate to CD154 binding proteins and anti-CD154 antibodies that bind to human CD154 with greater or equal affinity relative to a second CD154-specific antibody (e.g., antibody 5c8 or humanized 5c8), or with a $K_D$ that is lower than or equal to the $K_D$ of a second CD154-specific antibody, wherein the anti-CD154 antibody does not substantially inhibit the CD154:CD40 interaction relative to the second CD154-specific antibody. Such antibodies may be useful as binding assay and diagnostic reagents, for example. Exemplary antibodies that exhibit a high affinity for human CD154 but a lower degree of CD154:CD40 inhibition compared to a second CD154-specific antibody are antibodies 381 and 338 described herein. For example, the present invention provides anti-CD154 antibodies that specifically bind to human CD154 with higher or equal affinity (relative to a second CD154-specific antibody, such as humanized 5c8, for example) but that block the CD154:CD40 interaction to a lesser degree than does the second CD154-specific antibody. In further embodiments, these anti-CD154 antibodies that inhibit binding of CD154 (CD40L) to CD40 to a lesser degree than does a second CD154-specific antibody also do not substantially agonize CD40 activity or activate CD40 signaling. For example, such antibodies, if administered in an in vitro potency assay as described in Example 7, may not exhibit any statistically significant agonization over a control treatment or may exhibit 1%, 2%, 3%, 5%, or 10% agonization compared to a positive control (e.g., CD154 ligand). Vidalain et al. (*The EMBO Journal* (2000) 19: 3304-3313) and Pearson et al. (*International Immunology* (2001) 13:273-283) describe the CD40 signaling pathway and also provide assays that may be used to determine whether or not the CD154:CD40 interaction is blocked or inhibited, and to what extent.

In some embodiments, the present invention relates to an anti-CD154 antibody comprising at least one CDR selected from CDR-H1 (SEQ ID NO: 3), CDR-H2 (SEQ ID NO: 4) and CDR-H3 (SEQ ID NO: 5). Preferably, the antibody comprises at least two CDRs selected from CDR-H1 (SEQ ID NO: 3), CDR-H2 (SEQ ID NO: 4) and CDR-H3 (SEQ ID NO: 5) and more preferably all three of these CDR-H1, CDR-H2 and CDR-H3.

In another embodiment, the anti-CD154 antibody of the invention comprises at least one CDR selected from CDR-L1 (SEQ ID NO: 6), CDR-L2 (SEQ ID NO: 7) and CDR-L3 (SEQ ID NO: 8). Preferably, the antibody comprises at least two CDRs selected from CDR-L1 (SEQ ID NO: 6), CDR-L2 (SEQ ID NO: 7) and CDR-L3 (SEQ ID NO: 8) and more preferably all three of these CDR-L1, CDR-L2 and CDR-L3.

In further embodiments, the antibody comprises all three of CDR-H1, CDR-H2 and CDR-H3 (SEQ ID NOS: 3-5) and all three of CDR-L1, CDR-L2 and CDR-L3 (SEQ ID NOS: 6-8).

In further embodiments, the anti-CD154 antibody comprises a variable heavy chain sequence according to any one of SEQ ID NOS: 1, 9, 10 or 11 and comprises a variable light chain sequence according to SEQ ID NO: 2 or 14.

In some embodiments, the present invention relates to an anti-CD154 antibody comprising at least one CDR selected from CDR-H1 (SEQ ID NO: 42), CDR-H2 (SEQ ID NO: 43) and CDR-H3 (SEQ ID NO: 44). Preferably, the antibody comprises at least two CDRs selected from CDR-H1 (SEQ ID NO: 42), CDR-H2 (SEQ ID NO: 43) and CDR-H3 (SEQ ID NO: 44) and more preferably all three of these CDR-H1, CDR-H2 and CDR-H3.

In another embodiment, the anti-CD154 antibody of the invention comprises at least one CDR selected from CDR-L1 (SEQ ID NO: 45), CDR-L2 (SEQ ID NO: 46) and CDR-L3 (SEQ ID NO: 47). Preferably, the antibody comprises at least two CDRs selected from CDR-L1 (SEQ ID NO: 45), CDR-L2 (SEQ ID NO: 46) and CDR-L3 (SEQ ID NO: 47) and more preferably all three of these CDR-L1, CDR-L2 and CDR-L3.

In further embodiments, the antibody comprises all three of CDR-H1, CDR-H2 and CDR-H3 (SEQ ID NOS: 42-44) and all three of CDR-L1, CDR-L2 and CDR-L3 (SEQ ID NOS: 45-47).

In further embodiments, the anti-CD154 antibody comprises a variable heavy chain sequence according to SEQ ID NO: 56 and/or comprises a variable light chain sequence according to SEQ ID NO: 54.

In some embodiments, the present invention relates to an anti-CD154 antibody comprising at least one CDR selected from CDR-H1 (SEQ ID NO: 48), CDR-H2 (SEQ ID NO: 49) and CDR-H3 (SEQ ID NO: 50). Preferably, the antibody comprises at least two CDRs selected from CDR-H1 (SEQ ID NO: 48), CDR-H2 (SEQ ID NO: 49) and CDR-H3 (SEQ ID NO: 50) and more preferably all three of these CDR-H1, CDR-H2 and CDR-H3.

In another embodiment, the anti-CD154 antibody of the invention comprises at least one CDR selected from CDR-L1 (SEQ ID NO: 51), CDR-L2 (SEQ ID NO: 52) and CDR-L3 (SEQ ID NO: 53). Preferably, the antibody comprises at least two CDRs selected from CDR-L1 (SEQ ID NO: 51), CDR-L2 (SEQ ID NO: 52) and CDR-L3 (SEQ ID NO: 53) and more preferably all three of these CDR-L1, CDR-L2 and CDR-L3.

In certain embodiments, the antibodies have a complementary sequence comprising one or more light chain CDRs of CDR-L1, CDR-L2 and CDR-L3, above, or a complementary sequence comprising one or more heavy chain CDRs or CDR-H1, CDR-H2 and CDR-H3, above, respectively. Thus, in certain embodiments, an antibody of this invention comprises CDR-H1 (SEQ ID NO: 48), CDR-H2 (SEQ ID NO: 49) or CDR-H3 (SEQ ID NO: 50), and CDR-L1 (SEQ ID NO: 51), CDR-L2 (SEQ ID NO: 52) or CDR-L3 (SEQ ID NO: 53).

In further embodiments, the antibody comprises all three of CDR-H1, CDR-H2 and CDR-H3 (SEQ ID NOS: 48-50) and all three of CDR-L1, CDR-L2 and CDR-L3 (SEQ ID NOS: 51-53).

In further embodiments, the anti-CD154 antibody comprises a variable heavy chain sequence according to SEQ ID NO: 60 and/or comprises a variable light chain sequence according to SEQ ID NO: 58.

In certain embodiments, the CD154 binding protein of this invention comprises a light chain sequence according to SEQ ID NO: 62 and a heavy chain sequence according to SEQ ID NO: 65. In other embodiments, the CD154 binding protein of this invention comprises a light chain sequence according to SEQ ID NO: 63 and a heavy chain sequence according to SEQ ID NO: 66.

In certain embodiments, the CD154 binding protein of this invention comprises a light chain sequence according to SEQ ID NO: 68 and a heavy chain sequence according to SEQ ID NO: 71. In other embodiments, the CD154 binding protein of this invention comprises a light chain sequence according to SEQ ID NO: 69 and a heavy chain sequence according to SEQ ID NO: 72. In other embodiments, the CD154 binding protein comprises one of the sequences according to SEQ ID NO: 68, SEQ ID NO: 69, SEQ ID NO: 71 or SEQ ID NO: 72.

This invention also provides CD154 binding proteins that preferably share at least 90%, 91%, 92%, 93% or 94% identity with a CD154 binding protein of the invention. More preferably, a CD154 binding protein shares at least 95%, 96%, 97% or 98% identity. Most preferably, a CD154 binding protein shares at least 99%, 99.5%, 99.9% or more identity with a CD154 binding protein of the invention. The CD154 binding proteins of the invention may comprise a variable domain sequence is at least 85% identical to a variable domain of SEQ ID NO: 1, SEQ ID NO: 2, SEQ ID NO: 9, SEQ ID NO: 10, SEQ ID NO: 11, SEQ ID NO: 14, SEQ ID NO: 29, SEQ ID NO: 30, SEQ ID NO: 54, SEQ ID NO: 56, SEQ ID NO: 58 or SEQ ID NO: 60, or one or more CDRs thereof.

Other embodiments of the invention relate to bispecific antibodies. Bispecific antibodies are monoclonal, preferably human or humanized, antibodies that have binding specificities for at least two different antigens. They may be used alone or mixed into compositions comprising polyclonal populations. In the present invention, one of the binding specificities is for the CD154 antigen while the other binding specificity is for any other antigen, and preferably for a cell-surface protein or receptor or receptor subunit. For example, the other binding specificity may be a ligand selected from among human serum albumin (HSA), TNFα, IL-1, IL-2, IL-4, IL-6, IL-8, IL-12, IL-18, IFN-γ, CD2, CD4, CD8, CTLA4, LFA1, LFA3 and VLA4.

In other embodiments of the present invention, an anti-CD154 antibody comprises a generic ligand binding site. A generic ligand (e.g., a polypeptide) is capable of binding functional members of a repertoire regardless of target ligand specificity. A generic ligand may therefore be used to identify or select (for example, as in purification and screening processes) functional members of a repertoire (such as a collection or group of antibodies, regardless of the antibodies' antigen binding specificities). Generic ligands include, for example, Protein A, Protein G and Protein L. Pre-selection of members of a phage library with generic ligands is taught in WO 99/20749.

Antibody Fragments

The present invention also relates to antigen-binding or epitope-binding anti-CD154 antibody fragments. All of the methods and reagents described above with respect to anti-CD154 antibodies may similarly be used to produce and use anti-CD154 antibody fragments of this invention.

In some embodiments of this invention, the anti-CD154 antibody fragments include heteromeric antibody complexes and antibody fusions, such as bispecific antibodies, hemi-dimeric antibodies, multivalent antibodies (i.e., tetravalent antibodies) and single-chain antibodies. A hemidimeric antibody is made up of an Fc portion and one Fab portion. A single chain antibody is made up of variable regions linked by protein spacers in a single protein chain.

In some embodiments of this invention, the anti-CD154 antibody fragments of this invention may also include proteins containing one or more immunoglobulin light chains and/or heavy chains, such as monomers and homo- or hetero-multimers (e.g., dimers or trimers) of these chains, where these chains are optionally disulfide-bonded or otherwise cross-linked. These antibodies may be capable of binding to one or more antigens.

In certain embodiments, the present invention includes antigen-binding fragments of whole antibodies, such as Fab, F(ab)$_2$, Fab', F(ab')$_2$, F(ab')$_3$, F(v), Fd, dAb, diabody, minibody, and nanobody antibody fragments. The present invention also relates to fragments comprising only a single variable domain, such as a $V_H$ or $V_L$ domain, or to a fragment comprising only the heavy chain or light chain domains. The fragments may be humanized or fully human. The present invention also includes antigen-binding fragments that are made from alternative scaffolds (see, e.g., Binz supra and Hosse supra) or that comprise a universal framework. The present invention also relates to conjugates comprising any antigen-binding fragment or CD154 binding protein that specifically binds CD154 conjugated covalently or noncovalently, or directly or indirectly, to a functional moiety such as a carrier protein or PEG, for example.

Anti-CD154 antibodies of the present invention include divalent antibodies. Thus, in certain embodiments, the invention relates to a divalent anti-CD154 antibody fragment comprising two antibody heavy chains and at least one polymer molecule in covalent linkage, each heavy chain being covalently linked to the other by at least one non-disulfide interchain bridge linking the sulfur atom of a cysteine residue in one chain to the sulfur atom of a cysteine residue in the other chain, the cysteine residues being located outside of the variable region domain of each chain, characterized in that at least one non-disulfide interchain bridge contains a covalently linked polymer molecule. The term "non-disulfide" as used herein is intended to mean that S—S bridges, e.g. of the type normally found in antibodies, are excluded. An interchain bridge of the type present in a fragment according to the invention may however still be linked to a heavy chain via a-S—S-bond as described hereinafter. In general, each polymer molecule in the divalent antibody fragment according to the invention forms part of an interchain bridge. Each bridge serves to link two heavy chains and in each chain will be covalently linked to a sulphur atom of a cysteine residue. The covalent linkage will generally be a disulfide bond or, in particular embodiments a sulfur-carbon bond. For exemplary divalent antibody structures, see WO 99/64460 and WO 05/061005.

The invention also provides an anti-CD154 antibody that is a monovalent antibody or monovalent antigen-binding fragment. As used herein, the term "monovalent" means that a given antibody or antigen-binding fragment (e.g., Fv, a single chain scFv, dAb, Fab, Fab', Fd, scFab, scFabΔC, etc.) can bind only a single molecule of its target. Naturally-occurring antibodies are generally divalent, in that they have two functional antigen-binding arms, each comprising a $V_H$ and a $V_L$ domain. A divalent antibody can bind two separate molecules of the same antigen where steric hindrance is not an issue. In contrast, a "monovalent" antibody has one antigen-binding site for a target. The antigen-binding domain of a monovalent antibody may comprise a $V_H$ and a $V_L$ domain or may comprise only a single immunoglobulin variable domain, i.e., a $V_H$ or a $V_L$ domain, that has the capacity to bind CD154 without the need for a corresponding $V_L$ or $V_H$ domain, respectively. Such an exemplary monovalent antibody is an Fd fragment that comprises a single immunoglobulin variable domain and that can only bind to one CD154 antigen molecule. A monovalent antibody lacks the capacity to cross link molecules of a single antigen.

This invention provides an anti-CD154 antibody, wherein the antibody specifically binds to an epitope to which a humanized Fab or Fab' fragment with a heavy chain sequence according to SEQ ID NO: 12 or 13, respectively and with a light chain sequence according to SEQ ID NO: 15 specifically binds. In certain embodiments, an antibody of this invention is an antibody fragment with a variable heavy chain sequence according to SEQ ID NO: 1, 9, 10 or 11 and with a variable light chain sequence according to SEQ ID NO: 2 or 14. In other embodiments, the antibody of this invention is an antibody fragment with a heavy chain sequence according to SEQ ID NO. 12 or 13 and a light chain sequence according to SEQ ID NO. 15.

In certain embodiments, the CD154 binding protein or antibody comprises or consists of a light chain sequence of SEQ ID NO: 15 and a heavy chain sequence of SEQ ID NO: 13. In certain embodiments, the CD154 binding protein or antibody comprises or consists of a light chain sequence of SEQ ID NO: 15 and a heavy chain sequence of SEQ ID NO: 12.

In alternative embodiments, the invention provides an antibody fragment comprising a variable heavy chain sequence according to SEQ ID NO: 56 and comprising a variable light chain sequence according to SEQ ID NO: 54. In other embodiments, the antibody of this invention is an antibody fragment comprising a variable heavy chain sequence according to SEQ ID NO. 60 and comprising a variable light chain sequence according to SEQ ID NO. 58.

In one embodiment, this invention provides a Fab' or a F(ab')$_2$ or a F(ab')$_3$ fragment that specifically binds CD154. This Fab' or F(ab')$_2$ or F(ab')$_3$ fragment may be humanized and may have a heavy chain sequence that comprises or consists of the sequence of SEQ ID NO: 13 and may have a light chain sequence that comprises or consists of the sequence of SEQ ID NO: 15.

In some embodiments, the present invention relates to an anti-CD154 antibody that is free of an Fc domain. Such an Fc-deficient antibody or fragment may be monovalent, divalent, or further multivalent.

This invention also provides antibodies or antibody fragments that bind specifically to the epitope to which the Fab' or F(ab')$_2$ or F(ab')$_3$ fragments described above specifically bind. These antibodies or antibody fragments may be identified by a cross-blocking assay as described herein (Example 9). These antibodies or antibody fragments may be isolated, recombinant or synthetic and may be attached to a second molecule to form an antibody-conjugate.

Antibodies with Reduced Effector Function

The interaction of antibodies and antibody-antigen complexes with cells of the immune system triggers a variety of responses, referred to herein as effector functions. IgG antibodies activate effector pathways of the immune system by binding to members of the family of cell surface Fcγ receptors and to C1q of the complement system. Ligation of effector proteins by clustered antibodies triggers a variety of responses, including release of inflammatory cytokines, regulation of antigen production, endocytosis, and cell killing. In some clinical applications these responses are crucial for the efficacy of a monoclonal antibody. In others they provoke unwanted side effects such as inflammation and the elimination of antigen-bearing cells. Accordingly, the present invention further relates to CD154 binding proteins, including antibodies, with altered, e.g., reduced, effector functions. Importantly, reduced effector function does not necessarily reduce the ability of an anti-CD154 antibody to inhibit one or several diseases via blocking the CD154-CD40 interaction (see WO 05/03175, which is incorporated herein by reference in its entirety).

Anti-CD154 antibodies with diminished effector function (e.g., Fc-mediated effector functions; see below) are particularly desirable for use in subjects where the potential for undesirable thromboembolic activity exists. Additionally, the diminished effector function of anti-CD154 antibodies may decrease or eliminate other potential undesired side effects of anti-CD154 antibody therapies, such as deletion of activated T cells and other populations of cells induced to express CD154 or Fc-dependent activation of monocytes/macrophages.

Effector function of an anti-CD154 antibody of the present invention may be determined using one of many known assays. The anti-CD154 antibody's effector function may be reduced relative to a second anti-CD154 antibody. In some embodiments, the second anti-CD154 antibody may be any antibody that binds CD154 specifically. In some embodiments, the second anti-CD154 antibody may be antibody 5c8 (produced by the hybridoma deposited with ATCC under Accession No. HB 10916, as described in U.S. Pat. No. 5,474,771) or humanized 5c8). In other embodiments, the second CD154-specific antibody may be any of the antibodies of the invention, such as 342, 381, 338, 294, 295, 300, 335, 303 or 402 (FIG. 12). In other embodiments, where the anti-CD154 antibody of interest has been modified to reduce effector function, the second anti-CD154 antibody may be the unmodified or parental version of the antibody.

Effector function of an anti-CD154 antibody of the present invention may also be determined, e.g., by measuring the level of platelet aggregation or activation caused by treatment with the anti-CD154 antibody relative to a control antibody. In some embodiments, therefore, the anti-CD154 antibodies of the present invention do not mediate or do not enhance platelet aggregation or activation in a standard platelet aggregation or activation assay. In other embodiments, the anti-CD154 antibodies mediate a lower level of platelet aggregation or activation relative to a second anti-CD154 antibody (e.g., 5c8 or humanized 5c8).

Exemplary effector functions include Fc receptor binding, phagocytosis, apoptosis, pro-inflammatory responses, down-regulation of cell surface receptors (e.g. B cell receptor; BCR), etc. Other effector functions include antibody-dependent cell-mediated cytotoxicity (ADCC), whereby antibodies bind Fc receptors on cytotoxic T cells, natural killer (NK) cells, or macrophages leading to cell death, and complement-dependent cytotoxicity (CDC), which is cell death induced via activation of the complement cascade (reviewed in Daeron, *Annu. Rev. Immunol.* 15:203-234 (1997); Ward and Ghetie, *Therapeutic Immunol.* 2:77-94 (1995); and Ravetch and Kinet, *Annu. Rev. Immunol.* 9:457-492 (1991)). Such effector functions generally require the Fc region to be combined with a binding domain (e.g. an antibody variable domain) and can be assessed using standard assays that are known in the art (see, e.g., WO 05/018572, WO 05/003175, and U.S. Pat. No. 6,242,195).

Effector functions can be avoided by using antibody fragments lacking the Fc domain such as Fab, Fab'2, or single chain Fv. An alternative has been to use the IgG4 subtype antibody, which binds to FcγRI but which binds poorly to C1q and FcγRII and RIII. The IgG2 subtype also has reduced binding to Fc receptors, but retains significant binding to the H131 allotype of FcγRIIa and to C1q. Thus, additional changes in the Fc sequence are required to eliminate binding to all the Fc receptors and to C1q.

Several antibody effector functions, including ADCC, are mediated by Fc receptors (FcRs), which bind the Fc region of an antibody. The affinity of an antibody for a particular FcR, and hence the effector activity mediated by the antibody, may be modulated by altering the amino acid sequence and/or post-translational modifications of the Fc and/or constant region of the antibody.

FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Both FcγRII and FcγRIII have two types: FcγRIIA (CD32) and FcγRIIB (CD32); and FcγRIIIA (CD16a) and FcγRIIIB (CD16b). Because each FcγR subclass is encoded by two or three genes, and alternative RNA splicing leads to multiple transcripts, a broad diversity in FcγR isoforms exists. For example, FcγRII (CD32) includes the isoforms 11a, 11b1, 11b2 11b3, and 11c.

The binding site on human and murine antibodies for FcγR has been previously mapped to the so-called "lower hinge region" consisting of residues 233-239 (EU index numbering as in Kabat et al., Sequences of Proteins of Immunological Interest, 5th Ed. Public Health Service, National Institutes of Health, Bethesda, Md. (1991), Woof et al. *Molec. Immunol.* 23:319-330 (1986); Duncan et al. *Nature* 332:563 (1988); Canfield and Morrison, *J. Exp. Med.* 173:1483-1491 (1991); Chappel et al., *Proc. Natl. Acad. Sci USA* 88:9036-9040 (1991)). Of residues 233-239, P238 and S239 are among those cited as possibly being involved in binding. Other previously cited areas possibly involved in binding to FcγR are: G316-K338 (human IgG) for human FcγRI (by sequence comparison only; no substitution mutants were evaluated) (Woof et al. *Molec Immunol.* 23:319-330 (1986)); K274-R301 (human IgG1) for human FcγRIII (based on peptides) (Sarmay et al. *Molec. Immunol.* 21:43-51 (1984)); and Y407-R416 (human IgG) for human FcγRIII (based on peptides) (Gergely et al. *Biochem. Soc. Trans.* 12:739-743 (1984) and Shields et al. *J Biol Chem* 276: 6591-6604 (2001), Lazar G A et al. *Proc Natl Acad Sci* 103: 4005-4010 (2006). These and other stretches or regions of amino acid residues involved in FcR binding may be evident to the skilled artisan from an examination of the crystal structures of Ig-FcR complexes (see, e.g., Sondermann et al. 2000 *Nature* 406(6793):267-73 and Sondermann et al. 2002 *Biochem Soc Trans.* 30(4):481-6). Accordingly, the anti-CD154 antibodies of the present invention include modifications of one or more of the aforementioned residues.

Other known approaches for reducing mAb effector function include mutating amino acids on the surface of the mAb that are involved in effector binding interactions (Lund, J., et al. (1991) *J. Immunol.* 147(8): 2657-62; Shields, R. L. et al. (2001) *J. Biol. Chem.* 276(9): 6591-604; and using combinations of different subtype sequence segments (e.g., IgG2 and IgG4 combinations) to give a greater reduction in binding to Fcγ receptors than either subtype alone (Armour et al., *Eur. J. Immunol.* (1999) 29: 2613-1624; *Mol. Immunol.* 40 (2003) 585-593).

A large number of Fc variants having altered and/or reduced affinities for some or all Fc receptor subtypes (and thus for effector functions) are known in the art. See, e.g., US 2007/0224188; US 2007/0148171; US 2007/0048300; US 2007/0041966; US 2007/0009523; US 2007/0036799; US 2006/0275283; US 2006/0235208; US 2006/0193856; US 2006/0160996; US 2006/0134105; US 2006/0024298; US 2005/0244403; US 2005/0233382; US 2005/0215768; US 2005/0118174; US 2005/0054832; US 2004/0228856; US 2004/132101; US 2003/158389; see also U.S. Pat. Nos. 7,183,387; 6,737,056; 6,538,124; 6,528,624; 6,194,551; 5,624,821; 5,648,260.

In CDC, the antibody-antigen complex binds complement, resulting in the activation of the complement cascade and generation of the membrane attack complex. Activation of the classical complement pathway is initiated by the binding of the first component of the complement system (C1q) to antibodies (of the appropriate subclass) which are bound to their cognate antigen; thus the activation of the complement cascade is regulated in part by the binding affinity of the immunoglobulin to C1q protein. To activate the complement cascade, it is necessary for C1q to bind to at least two molecules of IgG1, IgG2, or IgG3, but only one molecule of IgM, attached to the antigenic target (Ward and Ghetie, *Therapeutic Immunology* 2:77-94 (1995) p. 80). To assess complement activation, a CDC assay, e.g. as described in Gazzano-Santoro et al., *J. Immunol. Methods* 202:163 (1996) may be performed.

It has been proposed that various residues of the IgG molecule are involved in binding to C1q including the Glu318, Lys320 and Lys322 residues on the CH2 domain, amino acid residue 331 located on a turn in close proximity to the same beta strand, the Lys235 and Gly237 residues located in the lower hinge region, and residues 231 to 238 located in the N-terminal region of the CH2 domain (see e.g., Xu et al., *J. Immunol.* 150:152 A (Abstract) (1993), WO94/29351; Tao et al., *J. Exp. Med.*, 178:661-667 (1993); Brekke et al., *Eur. J. Immunol.*, 24:2542-47 (1994); Burton et al.; *Nature*, 288:338-344 (1980); Duncan and Winter, *Nature* 332:738-40 (1988); Idusogie et al., *J Immunol* 164: 4178-4184 (2000; U.S. Pat. No. 5,648,260, and U.S. Pat. No. 5,624,821). As an example in IgG1, two mutations in the COOH terminal region of the CH2 domain of human IgG1—K322A and P329A—do not activate the CDC pathway and were shown to result in more than a 100 fold decrease in C1q binding (U.S. Pat. No. 6,242,195).

Thus, in certain embodiments of the invention, one or more of these residues may be modified, substituted, or removed or one or more amino acid residues may be inserted so as to decrease CDC activity of the CD154 antibodies provided herein. For example in some embodiments, it may be desirable to reduce or eliminate effector function(s) of the subject antibodies in order to reduce or eliminate the potential of further activating immune responses. Antibodies with decreased effector function may also reduce the risk of thromboembolic events in subjects receiving the antibodies.

In certain other embodiments, the present invention provides an anti-CD154 antibody that exhibits reduced binding to one or more FcR receptors but that maintains its ability to bind complement (e.g., to a similar or, in some embodiments, to a lesser extent than a native, non-variant, or parent anti-CD154 antibody). Accordingly, an anti-CD154 antibody of the present invention may bind and activate complement while exhibiting reduced binding to an FcR, such as, for example, FcγRIIa (e.g., FcγRIIa expressed on platelets). Such an antibody with reduced or no binding to FcγRIIa (such as FcγRIIa expressed on platelets, for example) but that can bind C1q and activate the complement cascade to at least some degree will reduce the risk of thromboembolic events while maintaining perhaps desirable effector functions. In alternative embodiments, an anti-CD154 antibody of the present invention exhibits reduced binding to one or more FcRs but maintains its ability to bind one or more other FcRs. See, for example, US 2007-0009523, 2006-0194290, 2005-0233382, 2004-0228856, and 2004-0191244, which describe various amino acid modifications that generate antibodies with reduced binding to FcRI, FcRII, and/or FcRIII, as well as amino acid substitutions that result in increased binding to one FcR but decreased binding to another FcR.

Accordingly, effector functions involving the constant region of an anti-CD154 antibody may be modulated by altering properties of the constant region, and the Fc region in particular. In certain embodiments, the anti-CD154 antibody having reduced effector function is compared with a second antibody with effector function and which may be a non-variant, native, or parent antibody (e.g., antibody 342 or antibody 5c8, which is described in U.S. Pat. No. 5,474,771) comprising a native constant or Fc region that mediates effector function. In particular embodiments, effector function modulation includes situations in which an activity is abolished or completely absent.

A native sequence Fc or constant region comprises an amino acid sequence identical to the amino acid sequence of a Fc or constant chain region found in nature. Preferably, a control molecule used to assess relative effector function comprises the same type/subtype Fc region as does the test or variant antibody. A variant or altered Fc or constant region comprises an amino acid sequence which differs from that of a native sequence heavy chain region by virtue of at least one amino acid modification (such as, for example, post-translational modification, amino acid substitution, insertion, or deletion). Accordingly, the variant constant region may contain one or more amino acid substitutions, deletions, or insertions that results in altered post-translational modifications, including, for example, an altered glycosylation pattern. A parent antibody or Fc region is, for example, a variant having normal effector function used to construct a constant region (i.e., Fc) having altered, e.g., reduced, effector function.

Antibodies with altered (e.g., reduced or eliminated) effector function(s) may be generated by engineering or producing antibodies with variant constant, Fc, or heavy chain regions. Recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g. glycosylation patterns (see below), may be achieved by manipulating the host cell and cell culture and expression conditions by which the antibody is produced.

Amino acid alterations, such as amino acid substitutions, can alter the effector function of the anti-CD154 antibodies of the present invention without affecting antigen binding affinity. The amino acid substitutions described above (e.g., Glu318, Kys320, Lys332, Lys235, Gly237, K332, and P329), for example, may be used to generate antibodies with reduced effector function.

In other embodiments, amino acid substitutions may be made for one or more of the following amino acid residues: 234, 235, 236, 237, 297, 318, 320, and 322 of the heavy chain constant region (see U.S. Pat. No. 5,624,821 and U.S. Pat. No. 5,648,260). Such substitutions may alter effector function while retaining antigen binding activity. An alteration at one or more of amino acids 234, 235, 236, and 237 can decrease the binding affinity of the Fc region for FcγRI receptor as compared to an unmodified or non-variant antibody. Amino acid residues 234, 236, and/or 237 may be substituted with alanine, for example, and amino acid residue 235 may be substituted with glutamine, for example. In another embodiment, an anti-CD154 IgG1 antibody may comprise a substitution of Leu at position 234 with Ala, a substitution of Leu at position 235 with Glu, and a substitution of Gly at position 237 with Ala.

Additionally or alternatively, the Fc amino acid residues at 318, 320, and 322 may be altered. These amino acid residues, which are highly conserved in mouse and human IgGs, mediate complement binding. It has been shown that alteration of these amino acid residues reduces C1q binding but does not alter antigen binding, protein A binding, or the ability of the Fc to bind to mouse macrophages.

In another embodiment, an anti-CD154 antibody of the present invention is an IgG4 immunoglobulin comprising substitutions that reduce or eliminate effector function. The IgG4 Fc portion of an anti-CD154 antibody of the invention may comprise one or more of the following substitutions: substitution of proline for glutamate at residue 233, alanine or valine for phenylalanine at residue 234 and alanine or glutamate for leucine at residue 235 (EU numbering, Kabat, E. A. et al. (1991), supra). Further, removing the N-linked glycosylation site in the IgG4 Fc region by substituting Ala for Asn at residue 297 (EU numbering) may further reduce effector function and eliminate any residual effector activity that may exist. Another exemplary IgG4 mutant with reduced effector function is the IgG4 subtype variant containing the mutations S228P and L235E (PE mutation) in the heavy chain constant region. This mutation results in reduced effector function. See U.S. Pat. No. 5,624,821 and U.S. Pat. No. 5,648,260. Another exemplary mutation in the IgG4 context that reduces effector function is S228P/T229A, as described herein.

Other exemplary amino acid sequence changes in the constant region include but are not limited to the Ala-Ala mutation described by Bluestone et al. (see WO 94/28027 and WO 98/47531; also see Xu et al. 2000 *Cell Immunol* 200; 16-26). Thus in certain embodiments, anti-CD154 antibodies with mutations within the constant region including the Ala-Ala mutation may be used to reduce or abolish effector function. According to these embodiments, the constant region of an anti-CD154 antibody comprises a mutation to an alanine at position 234 or a mutation to an alanine at position 235. Additionally, the constant region may contain a double mutation: a mutation to an alanine at position 234 and a second mutation to an alanine at position 235.

In one embodiment, an anti-CD154 antibody comprises an IgG4 framework, wherein the Ala-Ala mutation would describe a mutation(s) from phenylalanine to alanine at position 234 and/or a mutation from leucine to alanine at position 235. In another embodiment, the anti-CD154 antibody comprises an IgG1 framework, wherein the Ala-Ala mutation would describe a mutation(s) from leucine to alanine at position 234 and/or a mutation from leucine to alanine at position 235. An anti-CD154 antibody may alternatively or additionally carry other mutations, including the point mutation K322A in the CH2 domain (Hezareh et al. 2001 *J Virol.* 75: 12161-8).

Other exemplary amino acid substitutions are provided in WO 94/29351 (which is incorporated herein by reference in its entirety), which recites antibodies having mutations in the N-terminal region of the CH2 domain that alter the ability of the antibodies to bind to FcRI, thereby decreasing the ability of antibodies to bind to C1q which in turn decreases the ability of the antibodies to fix complement. Also see Cole et al. (*J. Immunol.* (1997) 159: 3613-3621), which describes mutations in the upper CH2 regions in IgG2 that result in lower FcR binding.

Methods of generating any of the aforementioned antibody variants comprising amino acid substitutions are well known in the art. These methods include, but are not limited to, preparation by site-directed (or oligonucleotide-mediated) mutagenesis, PCR mutagenesis, and cassette mutagenesis of a prepared DNA molecule encoding the antibody or at least the constant region of the antibody.

Site-directed mutagenesis is well known in the art (see, e.g., Carter et al. *Nucleic Acids Res.* 13:4431-4443 (1985) and Kunkel et al., *Proc. Natl. Acad. Sci. USA* 82:488 (1987)).

PCR mutagenesis is also suitable for making amino acid sequence variants of the starting polypeptide. See Higuchi, in PCR Protocols, pp. 177-183 (Academic Press, 1990); and Vallette et al., *Nuc. Acids Res.* 17:723-733 (1989).

Another method for preparing sequence variants, cassette mutagenesis, is based on the technique described by Wells et al., *Gene* 34:315-323 (1985).

Another embodiment of the present invention relates to an anti-CD154 antibody with reduced effector function in which the antibody's Fc region, or portions thereof, is swapped with an Fc region (or with portions thereof) having naturally reduced effector inducing activity. For example, human IgG4 constant region exhibits reduced or no complement activation. Further, the different IgG molecules differ in their binding affinity for FcR, which may be due at least in part to the varying length and flexibility of the IgGs' hinge regions (which decreases in the order IgG3>IgG1>IgG4>IgG2). For example, IgG4 exhibits reduced or no binding to FcγRIIa. For examples of chimeric molecules and chimeric constant regions, see, e.g., Gillies et al. (*Cancer Res.* 1999, 59: 2159-2166) and Mueller et al. (*Mol. Immunol.* 1997, 34: 441-452).

The invention also relates to anti-CD154 antibodies with reduced effector function in which the Fc region is completely absent. Such antibodies may also be referred to as antibody derivatives and antigen-binding fragments of the present invention. Such derivatives and fragments may be fused to non-antibody protein sequences or non-protein structures, especially structures designed to facilitate delivery and/or bioavailability when administered to an animal, e.g., a human subject (see below).

As discussed above, changes within the hinge region also affect effector functions. For example, deletion of the hinge region may reduce affinity for Fc receptors and may reduce complement activation (Klein et al. 1981 *PNAS USA* 78: 524-528). The present disclosure therefore also relates to antibodies with alterations in the hinge region.

In particular embodiments, antibodies of the present invention may be modified to inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551 and U.S. Pat. No. 6,242,195). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., *J. Exp Med.* 176:1191-1195 (1992) and Shopes, B. *J. Immunol.* 148:2918-2922 (1992), WO 99/51642, Duncan & Winter *Nature* 322: 738-40 (1988); U.S. Pat. No. 5,648,260; U.S. Pat. No. 5,624,821; and WO 94/29351.

It is further understood that effector function may vary according to the binding affinity of the antibody. For example, antibodies with high affinity may be more efficient in activating the complement system compared to antibodies with relatively lower affinity (Marzocchi-Machado et al. 1999 *Immunol Invest* 28: 89-101). Accordingly, an antibody may be altered such that the binding affinity for its antigen is reduced (e.g., by changing the variable regions of the antibody by methods such as substitution, addition, or deletion of one or more amino acid residues). An antibody with reduced binding affinity may exhibit reduced effector functions, including, for example, reduced ADCC and/or CDC.

Anti-CD154 antibodies of the present invention with reduced effector function include antibodies with reduced binding affinity for one or more Fc receptors (FcRs) relative to a parent or non-variant anti-CD154 antibody. Accordingly, anti-CD154 antibodies with reduced FcR binding affinity includes anti-CD154 antibodies that exhibit a 1.5-fold, 2-fold, 2.5-fold, 3-fold, 4-fold, or 5-fold or higher decrease in binding affinity to one or more Fc receptors compared to a parent or non-variant anti-CD154 antibody (e.g., antibody 342 or 5c8). In some embodiments, an anti-CD154 antibody with reduced effector function binds to an FcR with about 10-fold less affinity relative to a parent or non-variant antibody. In other embodiments, an anti-CD154 antibody with reduced effector function binds to an FcR with about 15-fold less affinity or with about 20-fold less affinity relative to a parent or non-variant antibody. The FcR receptor may be one or more of FcγRI (CD64), FcγRII (CD32), and FcγRIII, and isoforms thereof, and FcεR, FcμR, FcδR, and/or an FcαR. In particular embodiments, an anti-CD154 antibody with reduced effector function exhibits a 1.5-fold, 2-fold, 2.5-fold, 3-fold, 4-fold, or 5-fold or higher decrease in binding affinity to FcγRIIa.

Accordingly, in certain embodiments, an anti-CD154 antibody of the present invention exhibits reduced binding to a complement protein relative to a second anti-CD154 antibody. In certain embodiments, an anti-CD154 antibody of the invention exhibits reduced binding by a factor of about 1.5-fold or more, about 2-fold or more, about 3-fold or more, about 4-fold or more, about 5-fold or more, about 6-fold or more, about 7-fold or more, about 8-fold or more, about 9-fold or more, about 10-fold or more, or about 15-fold or more, relative to a second anti-CD154 antibody.

Accordingly, in certain embodiments, the present invention relates to antibodies that elicit reduced effector function when administered to a subject. In certain embodiments, an anti-CD154 antibody of this invention does not cause thrombosis in a subject to whom the antibody is administered. Thrombosis includes, for example, thromboembolic events. Such events include, e.g., vasculopathy (e.g., vascular changes such as intimal thickening and vessel wall changes). In some embodiments, an anti-CD154 antibody of this invention causes fewer thromboembolic events relative to a second CD154-specific antibody (e.g., antibody 342, antibody 5c8 or humanized 5c8). An anti-CD154 antibody with reduced effector function may show a 5%, 10%, 15%, 20%, 25%, 30%, 40%, or 50% reduction in the number of thromboembolic events when administered to a subject and compared to a non-variant or parent anti-CD154 antibody.

In certain embodiments, an anti-CD154 antibody of this invention does not cause platelet aggregation or activation in vitro and/or enhances platelet aggregation or activation to a lesser extent when compared to a second CD154-specific antibody (e.g., antibody 5c8 or humanized 5c8; see Example 1). Accordingly, in certain embodiments, the presence of a CD154 binding protein, e.g., an anti-CD154 antibody, of the present invention in a standard platelet aggregation or activation assay does not result in aggregation or activation of more than 20%, 25%, 30% or 50% over the aggregation or activation observed in a negative control assay. An exemplary standard platelet aggregation assay is the assay described herein (Example 11, Assay 1) and shown in FIG. 26. Both a standard assay and an alternative platelet aggregation assay (Assay 2, FIG. 27) that may be used in the invention are described in Example 11. The CD154 binding protein may be soluble.

In certain embodiments, this invention also provides CD154 binding protein, e.g., an anti-CD154 antibody, said protein comprising a single immunoglobulin variable domain which specifically and monovalently binds CD40L, wherein binding of said soluble protein to CD154 does not substantially induce JNK phosphorylation in Jurkat T-cells. This invention also provides CD154 binding protein, e.g., an anti-CD154 antibody, said protein comprising a single immunoglobulin variable domain which specifically and monovalently binds CD154, wherein binding of said soluble protein to CD154 does not substantially induce IFN-gamma secretion by Jurkat T-cells co-stimulated with anti-CD3 antibody.

Certain embodiments of the present invention relate to an anti-CD154 antibody comprising one or more heavy chain CDR sequences selected from DR-H1 (SEQ ID NO: 3), CDR-H2 (SEQ ID NO: 4) and CDR-H3 (SEQ ID NO: 5), wherein the antibody further comprises a variant Fc region that confers reduced effector function compared to a native or parental Fc region. In further embodiments, the anti-CD154 antibody comprises at least two of the CDRs, and in other embodiments the antibody comprises all three heavy chain CDR sequences, which are CDR-H1 (SEQ ID NO: 3), CDR-H2 (SEQ ID NO: 4) and CDR-H3 (SEQ ID NO: 5).

Other embodiments of the present invention relate to an anti-CD154 antibody comprising one or more light chain CDR sequences selected from CDR-L1 (SEQ ID NO: 6), CDR-L2 (SEQ ID NO: 7) and CDR-L3 (SEQ ID NO: 8), the antibody further comprising a variant Fc region that confers reduced effector function compared to a native or parental Fc region. In further embodiments, the anti-CD154 antibody comprises at least two of the light chain CDRs, and in other embodiments the antibody comprises all three light chain CDR sequences, which are CDR-L1 (SEQ ID NO: 6), CDR-L2 (SEQ ID NO: 7) and CDR-L3 (SEQ ID NO: 8).

In further embodiments of the present invention, the anti-CD154 antibody with reduced effector function comprises all three light chain CDR sequences, which are CDR-L1 (SEQ ID NO: 6), CDR-L2 (SEQ ID NO: 7) and CDR-L3 (SEQ ID NO: 8), and comprises all three heavy chain CDR sequences, which are CDR-H1 (SEQ ID NO: 3), CDR-H2 (SEQ ID NO: 4) and CDR-H3 (SEQ ID NO: 5).

In certain embodiments, this invention provides an anti-CD154 antibody that specifically binds a CD154 protein, wherein the antibody comprises a $V_H$ sequence selected from SEQ ID NO: 1, SEQ ID NO: 9, SEQ ID NO: 10 and SEQ ID NO: 11. In certain other embodiments, this invention provides an antibody that specifically binds a CD154 protein, wherein the antibody comprises a heavy chain sequence selected from SEQ ID NO: 12 and SEQ ID NO: 13. In further embodiments, the anti-CD154 antibody comprising any one or more of the CDRs or heavy or light chain sequences described above is a Fab or a Fab' fragment or a derivative thereof. In yet further embodiments, the antibody is a F(ab)$_2$ fragment or a derivative thereof. Other antibody fragments or derivatives thereof comprising the CDRs or the heavy or light chain sequences that specifically bind a CD154 protein are also included. These antibodies may be modified so as to elicit reduced or no effector functions. Accordingly, in certain embodiments, the present invention relates to an anti-CD154 antibody comprising a V$_H$ sequence selected from SEQ ID NO: 1, SEQ ID NO: 9, SEQ ID NO: 10 and SEQ ID NO: 11, the antibody further comprising a variant Fc region that confers reduced effector function compared to a native or parental Fc region.

In other embodiments, the invention relates to an anti-CD154 antibody comprising a V$_L$ sequence selected from SEQ ID NO: 2 and SEQ ID NO: 14, the antibody further comprising a variant Fc region that confers reduced effector function compared to a native or parental Fc region.

In some embodiments, an antibody comprises a variable light chain sequence of SEQ ID NO: 2. In further embodiments, an antibody comprising SEQ ID NO: 2 is a Fab or a Fab' fragment or a derivative thereof. In yet other embodiments, the antibody is a F(ab)$_2$ fragment or a derivative thereof. Other antibody fragments or derivatives thereof comprising the CDRs or the heavy or light chain sequences that specifically bind a CD154 protein are also included.

In additional embodiments, the invention relates to an anti-CD154 antibody comprising a V$_L$ sequence selected from the group consisting of SEQ ID NO: 2 and SEQ ID NO: 14 and further comprising a V$_H$ sequence selected from SEQ ID NO: 1, SEQ ID NO: 9, SEQ ID NO: 10 and SEQ ID NO: 11, the antibody further comprising a variant Fc region that confers reduced effector function compared to a native or parental Fc region.

In other embodiments, the invention relates to an anti-CD154 antibody comprising a V$_H$ sequence of SEQ ID NO: 29 and a V$_L$ sequence of SEQ ID NO: 30, the antibody further comprising a variant Fc region that confers reduced effector function compared to a native or parental Fc region.

In certain embodiments, the present invention provides an anti-CD154 antibody that specifically binds a CD154 protein, wherein the antibody comprises the light chain sequence of SEQ ID NO: 15. In further embodiments, the antibody comprising the light chain sequence of SEQ ID NO: 15 further comprises a variant Fc region that confers reduced effector function compared to a native or parental Fc region (e.g., an Fc region with altered glycosylation and/or other modification).

In certain embodiments, the present invention relates to an anti-CD154 antibody comprising a light chain sequence of SEQ ID NO: 15 and a heavy chain sequence selected from the group consisting of SEQ ID NO: 12 and SEQ ID NO: 13, the antibody further comprising a variant Fc region that confers reduced effector function compared to a native or parental Fc region (e.g., an Fc region with altered glycosylation and/or other modification).

In certain embodiments, the invention provides an anti-CD154 antibody comprising a light chain sequence as set forth in SEQ ID NO: 2 or 14 and a heavy chain sequence as set forth in SEQ ID NO: 1, 9, 10 or 11. In some embodiments, the anti-CD154 antibody may be an antibody fragment. In further embodiments, the antibody is a Fab or a Fab' fragment or a derivative thereof. In yet further embodiments, the antibody is a F(ab')$_2$ fragment or a derivative thereof. Other antibody fragments or derivatives thereof comprising the CDRs or the heavy or light chain sequences that specifically bind a CD154 protein are also included. Additionally, the antibodies may exhibit reduced effector function. For example, antibodies comprising an Fc region may comprise an Fc region with one or more modifications (e.g., altered glycosylation, conjugation, etc.) such that the antibody elicits reduced or no effector function(s).

In other embodiments, the present invention relates to an anti-CD154 antibody comprising a light chain sequence of SEQ ID NO: 15 and a heavy chain sequence of SEQ ID NO: 13, wherein the antibody further comprises a variant Fc region that confers reduced effector function compared to a native or parental Fc region. In other embodiments, the present invention relates to an anti-CD154 antibody comprising a light chain sequence of SEQ ID NO: 15 and a heavy chain sequence of SEQ ID NO: 12, wherein the antibody further comprises a variant Fc region that confers reduced effector function compared to a native or parental Fc region.

In some embodiments, the present invention relates to an anti-CD154 antibody comprising one or more heavy chain CDR sequences selected CDR-H1 (SEQ ID NO: 42), CDR-H2 (SEQ ID NO: 43) and CDR-H3 (SEQ ID NO: 44), the antibody further comprising a variant Fc region that confers reduced effector function compared to a native or parental Fc region. In certain embodiments, the anti-CD154 antibody comprises at least two of the heavy chain CDRs, and in other embodiments the antibody comprises all three heavy chain CDR sequences, which are CDR-H1 (SEQ ID NO: 42), CDR-H2 (SEQ ID NO: 43) and CDR-H3 (SEQ ID NO: 44).

In certain embodiments, the invention relates to an anti-CD154 antibody comprising one or more light chain CDR sequences selected from CDR-L1 (SEQ ID NO: 45), CDR-L2 (SEQ ID NO: 46) and CDR-L3 (SEQ ID NO: 47), the antibody further comprising a variant Fc region that confers reduced effector function compared to a native or parental Fc region. In certain embodiments, the anti-CD154 antibody comprises at least two of the light chain CDRs, and in other embodiments the antibody comprises all three light chain CDR sequences, which are CDR-L1 (SEQ ID NO: 45), CDR-L2 (SEQ ID NO: 46) and CDR-L3 (SEQ ID NO: 47).

Further embodiments of the present invention relate to anti-CD154 antibody comprising a variant Fc region that confers reduced effector function compared to a native or parental Fc region, wherein the antibody comprises all three light chain CDR sequences, which are CDR-L1 (SEQ ID NO: 45), CDR-L2 (SEQ ID NO: 46) and CDR-L3 (SEQ ID NO: 47), and wherein the antibody comprises all three heavy chain CDR sequences, which are the CDR-H1 (SEQ ID NO: 42), CDR-H2 (SEQ ID NO: 43) and CDR-H3 (SEQ ID NO: 44).

In other embodiments, the present invention relates to an anti-CD154 antibody comprising one or more heavy chain CDR sequences selected from CDR-H1 (SEQ ID NO: 48), CDR-H2 (SEQ ID NO: 49) and CDR-H3 (SEQ ID NO: 50), the antibody further comprising a variant Fc region that confers reduced effector function compared to a native or parental Fc region. In further embodiments, the anti-CD154 antibody comprises at least two of the heavy chain CDRs, and in other embodiments the antibody comprises all three heavy chain CDR sequences, which are CDR-H1 (SEQ ID NO: 48), CDR-H2 (SEQ ID NO: 49) and CDR-H3 (SEQ ID NO: 50).

In certain embodiments, the present invention relates to an anti-CD154 antibody comprising one or more light chain CDR sequences selected from CDR-L1 (SEQ ID NO: 51), CDR-L2 (SEQ ID NO: 52) and CDR-L3 (SEQ ID NO: 53), the antibody further comprising a variant Fc region that confers reduced effector function compared to a native or parental Fc region. In further embodiments, the antibody comprises at least two of the light chain CDRs, and in other embodiments the antibody comprises all three light chain CDR sequences, which are the CDR-L1 (SEQ ID NO: 51), CDR-L2 (SEQ ID NO: 52) and CDR-L3 (SEQ ID NO: 53).

In certain embodiments, an anti-CD154 antibody with reduced effector function comprises all three light chain CDR sequences, which are CDR-L1 (SEQ ID NO: 51), CDR-L2 (SEQ ID NO: 52) and CDR-L3 (SEQ ID NO: 53), and further comprises all three heavy chain CDR sequences, which are the CDR-H1 (SEQ ID NO: 48), CDR-H2 (SEQ ID NO: 49) and CDR-H3 (SEQ ID NO: 50).

In further embodiments, this invention provides an anti-CD154 antibody that specifically binds CD154, wherein the antibody comprises a $V_L$ sequence of SEQ ID NO: 54. The invention also relates to an anti-CD154 antibody that comprises a $V_H$ sequence of SEQ ID NO: 56. An anti-CD154 antibody of the invention may comprise both a $V_L$ sequence of SEQ ID NO: 54 and a $V_H$ sequence of SEQ ID NO: 56. In further embodiments, the antibody is a Fab or a Fab' fragment or a derivative thereof. In yet further embodiments, the antibody or antibody fragment is a F(ab')$_2$ fragment or a derivative thereof. The antibody or fragment may also be a humanized or fully human antibody or fragment thereof. Certain embodiments of the present invention relate to an anti-CD154 antibody comprising a $V_H$ sequence of SEQ ID NO: 56 and $V_L$ sequence of SEQ ID NO: 54, the antibody further comprising a variant Fc region that confers reduced effector function compared to a native or parental Fc region.

In further embodiments, this invention provides an anti-CD154 antibody that specifically binds CD154, wherein the antibody comprises a $V_L$ sequence of SEQ ID NO: 58. In additional embodiments, the antibody comprises a $V_H$ sequence of SEQ ID NO: 60. In further embodiments, the antibody or fragment comprises a $V_H$ sequence of SEQ ID NO: 60 and a $V_L$ sequence of SEQ ID NO: 58. The antibody may be a Fab or a Fab' fragment or a derivative thereof. In yet further embodiments, the antibody is a F(ab')$_2$ fragment or a derivative thereof. The antibody may also be a humanized or fully human antibody or fragment thereof. In other embodiments, the present invention relates to an anti-CD154 antibody comprising a $V_H$ sequence of SEQ ID NO: 58 and $V_L$ sequence of SEQ ID NO: 60, the antibody further comprising a variant Fc region that confers reduced effector function compared to a native or parental Fc region.

Anti-CD154 Antibodies with Altered Glycosylation

Glycan removal produces a structural change that should greatly reduce binding to all members of the Fc receptor family across species. In glycosylated antibodies, including anti-CD154 antibodies, the glycans (oligosaccharides) attached to the conserved N-linked site in the CH2 domains of the Fc dimer are enclosed between the CH2 domains, with the sugar residues making contact with specific amino acid residues on the opposing CH2 domain. Different glycosylation patterns are associated with different biological properties of antibodies (Jefferis and Lund, 1997, *Chem. Immunol.*, 65: 111-128; Wright and Morrison, 1997, *Trends Biotechnol.*, 15: 26-32). Certain specific glycoforms confer potentially advantageous biological properties. Loss of the glycans changes spacing between the domains and increases their mobility relative to each other and is expected to have an inhibitory effect on the binding of all members of the Fc receptor family. For example, in vitro studies with various glycosylated antibodies have demonstrated that removal of the CH2 glycans alters the Fc structure such that antibody binding to Fc receptors and the complement protein C1Q are greatly reduced. Another known approach to reducing effector functions is to inhibit production of or remove the N-linked glycans at position 297 (EU numbering) in the CH2 domain of the Fc (Nose et al., 1983 *PNAS* 80: 6632; Leatherbarrow et al., 1985 *Mol. Immunol.* 22: 407; Tao et al., 1989 *J. Immunol.* 143: 2595; Lund et al., 1990 *Mol. Immunol.* 27: 1145; Dorai et al., 1991 *Hybridoma* 10:211; Hand et al., 1992 *Cancer Immunol. Immunother.* 35:165; Leader et al., 1991 *Immunology* 72: 481; Pound et al., 1993 *Mol. Immunol.* 30:233; Boyd et al., 1995 *Mol. Immunol.* 32: 1311). It is also known that different glycoforms can profoundly affect the properties of a therapeutic, including pharmacokinetics, pharmacodynamics, receptor-interaction and tissue-specific targeting (Graddis et al., 2002, *Curr Pharm Biotechnol.* 3: 285-297). In particular, for antibodies, the oligosaccharide structure can affect properties relevant to protease resistance, the serum half-life of the antibody mediated by the FcRn receptor, phagocytosis and antibody feedback, in addition to effector functions of the antibody (e.g., binding to the complement complex C1, which induces CDC, and binding to FcγR receptors, which are responsible for modulating the ADCC pathway) (Nose and Wigzell, 1983; Leatherbarrow and Dwek, 1983; Leatherbarrow et al., 1985; Walker et al., 1989; Carter et al., 1992, *PNAS,* 89: 4285-4289).

Accordingly, another means of modulating effector function of antibodies includes altering glycosylation of the antibody constant region. Altered glycosylation includes, for example, a decrease or increase in the number of glycosylated residues, a change in the pattern or location of glycosylated residues, as well as a change in sugar structure(s). The oligosaccharides found on human IgGs affects their degree of effector function (Raju, T. S. *BioProcess International* April 2003. 44-53); the microheterogeneity of human IgG oligosaccharides can affect biological functions such as CDC and ADCC, binding to various Fc receptors, and binding to C1q protein (Wright A. & Morrison S L. TIBTECH 1997, 15 26-32; Shields et al. *J Biol Chem.* 2001 276(9):6591-604; Shields et al. *J Biol Chem.* 2002; 277(30):26733-40; Shinkawa et al. *J Biol Chem.* 2003 278(5):3466-73; Umana et al. *Nat Biotechnol.* 1999 February; 17(2): 176-80). For example, the ability of IgG to bind C1q and activate the complement cascade may depend on the presence, absence or modification of the carbohydrate moiety positioned between the two CH2 domains (which is normally anchored at Asn297) (Ward and Ghetie, *Therapeutic Immunology* 2:77-94 (1995).

Glycosylation sites in an Fc-containing polypeptide, for example an antibody such as an IgG antibody, may be identified by standard techniques. The identification of the glycosylation site can be experimental or based on sequence analysis or modeling data. Consensus motifs, that is, the amino acid sequence recognized by various glycosyl transferases, have been described. For example, the consensus motif for an N-linked glycosylation motif is frequently NXT or NXS, where X can be any amino acid except proline. Several algorithms for locating a potential glycosylation motif have also been described. Accordingly, to identify potential glycosylation sites within an antibody or Fc-containing fragment, the sequence of the antibody is examined, for example, by using publicly available databases such as the website provided by the Center for Biological Sequence Analysis (see NetNGlyc services for predicting N-linked glycosylation sites and NetOGlyc services for predicting O-linked glycosylation sites).

In vivo studies have confirmed the reduction in the effector function of aglycosyl antibodies. For example, an aglycosyl anti-CD8 antibody is incapable of depleting CD8-bearing cells in mice (Isaacs, 1992 *J. Immunol.* 148: 3062) and an aglycosyl anti-CD3 antibody does not induce cytokine release syndrome in mice or humans (Boyd, 1995 supra; Friend, 1999 *Transplantation* 68:1632).

Importantly, while removal of the glycans in the CH2 domain appears to have a significant effect on effector function, other functional and physical properties of the antibody remain unaltered. Specifically, it has been shown that removal of the glycans had little to no effect on serum half-life and binding to antigen (Nose, 1983 supra; Tao, 1989 supra; Dorai, 1991 supra; Hand, 1992 supra; Hobbs, 1992 *Mol. Immunol.* 29:949).

Although there is in vivo validation of the aglycosyl approach, there are reports of residual effector function with aglycosyl mAbs (see, e.g., Pound, J. D. et al. (1993) *Mol. Immunol.* 30(3): 233-41; Dorai, H. et al. (1991) *Hybridoma* 10(2): 211-7). Armour et al. show residual binding to FcγRIIa and FcγRIIb proteins (*Eur. J. Immunol.* (1999) 29: 2613-1624; *Mol. Immunol.* 40 (2003) 585-593). Thus a further decrease in effector function, particularly complement activation, may be important to guarantee complete ablation of activity in some instances. For that reason, aglycosyl forms of IgG2 and IgG4 and a G1/G4 hybrid are envisioned as being useful in methods and antibody compositions of the invention having reduced effector functions.

Generation of Deglycosylated or Aglycosyl Anti-CD154 Antibodies

The anti-CD154 antibodies of the present invention may be modified or altered to elicit reduced effector function(s) (compared to a second CD154-specific antibody) while optionally retaining the other valuable attributes of the Fc portion.

Accordingly, in certain embodiments, the present invention relates to aglycosyl anti-CD154 antibodies with decreased effector function, which are characterized by a modification at the conserved N-linked site in the CH2 domains of the Fc portion of the antibody. A modification of the conserved N-linked site in the CH2 domains of the Fc dimer can lead to aglycosyl anti-CD154 antibodies. Examples of such modifications include mutation of the conserved N-linked site in the CH2 domains of the Fc dimer, removal of glycans attached to the N-linked site in the CH2 domains, and prevention of glycosylation. For example, an aglycosyl anti-CD154 antibody may be created by changing the canonical N-linked Asn site in the heavy chain CH2 domain to a Gln residue (see, for example, WO 05/03175 and US 2006-0193856).

In one embodiment of present invention, the modification comprises a mutation at the heavy chain glycosylation site to prevent glycosylation at the site. Thus, in one embodiment of this invention, the aglycosyl anti-CD154 antibodies are prepared by mutation of the heavy chain glycosylation site, i.e., mutation of N298Q (N297 using Kabat EU numbering) and expressed in an appropriate host cell. For example, this mutation may be accomplished by following the manufacturer's recommended protocol for unique site mutagenesis kit from Amersham-Pharmacia Biotech® (Piscataway, N.J., USA).

The mutated antibody can be stably expressed in a host cell (e.g. NSO or CHO cell) and then purified. As one example, purification can be carried out using Protein A and gel filtration chromatography. It will be apparent to those of skill in the art that additional methods of expression and purification may also be used.

In another embodiment of the present invention, the aglycosyl anti-CD154 antibodies have decreased effector function, wherein the modification at the conserved N-linked site in the CH2 domains of the Fc portion of said antibody or antibody derivative comprises the removal of the CH2 domain glycans, i.e., deglycosylation. These aglycosyl anti-CD154 antibodies may be generated by conventional methods and then deglycosylated enzymatically. Methods for enzymatic deglycosylation of antibodies are well known to those of skill in the art (Williams, 1973; Winkelhake & Nicolson, 1976 *J. Biol Chem.* 251:1074-80).

In another embodiment of this invention, deglycosylation may be achieved by growing host cells which produce the antibodies in culture medium comprising a glycosylation inhibitor such as tunicamycin (Nose & Wigzell, 1983). That is, the modification is the reduction or prevention of glycosylation at the conserved N-linked site in the CH2 domains of the Fc portion of said antibody.

In other embodiments of this invention, recombinant CD154 polypeptides (or cells or cell membranes containing such polypeptides) may be used as an antigen to generate an anti-CD154 antibody or antibody derivatives, which may then be deglycosylated.

In alternative embodiments, agyclosyl anti-CD154 antibodies or anti-CD154 antibodies with reduced glycosylation of the present invention, may be produced by the method described in Taylor et al. (WO 05/18572 and US 2007-0048300). For example, in one embodiment, an anti-CD154 aglycosyl antibody may be produced by altering a first amino acid residue (e.g., by substitution, insertion, deletion, or by chemical modification), wherein the altered first amino acid residue inhibits the glycosylation of a second residue by either steric hindrance or charge or both. In certain embodiments, the first amino acid residue is modified by amino acid substitution. In further embodiments, the amino acid substitution is selected from the group consisting of Gly, Ala, Val, Leu, Ile, Phe, Asn, Gln, Trp, Pro, Ser, Thr, Tyr, Cys, Met, Asp, Glu, Lys, Arg, and His. In other embodiments, the amino acid substitution is a non-traditional amino acid residue. The second amino acid residue may be near or within a glycosylation motif, for example, an N-linked glycosylation motif that contains the amino acid sequence NXT or NXS. In one exemplary embodiment, the first amino acid residue is amino acid 299 and the second amino acid residue is amino acid 297, according to the Kabat numbering. For example, the first amino acid substitution may be T299A, T299N, T299G, T299Y, T299C, T299H, T299E, T299D, T299K, T299R, T299G, T299I, T299L, T299M, T299F, T299P, T299W, and T299V, according to the Kabat numbering. In particular embodiments, the amino acid substitution is T299C.

Effector function may also be reduced by modifying an antibody of the present invention such that the antibody contains a blocking moiety. Exemplary blocking moieties include moieties of sufficient steric bulk and/or charge such that reduced glycosylation occurs, for example, by blocking the ability of a glycosidase to glycosylate the polypeptide. The blocking moiety may additionally or alternatively reduce effector function, for example, by inhibiting the ability of the Fc region to bind a receptor or complement protein. In some embodiments, the present invention relates to a CD154 binding protein, e.g., an anti-CD154 antibody, comprising a heavy chain CDR3 sequence selected from SEQ ID NOS: 5, 44 and 50, and a variant Fc region, the variant Fc region comprising a first amino acid residue and an N-glycosylation site, the first amino acid residue modified with side chain chemistry to achieve increased steric bulk or increased electrostatic charge compared to the unmodified first amino acid residue, thereby reducing the level of or otherwise altering glycosylation at the N-glycosylation site. In certain of these embodiments, the variant Fc region confers reduced effector function compared to a control, non-variant Fc region. In further embodiments, the side chain with increased steric bulk is a side chain of an amino acid residue selected from the group consisting of Phe, Trp, His, Glu, Gln, Arg, Lys, Met and Tyr. In yet further embodiments, the side chain chemistry with increased electrostatic charge is a side chain of an amino acid residue selected from the group consisting of Asp, Glu, Lys, Arg, and His.

Accordingly, in one embodiment, glycosylation and Fc binding can be modulated by substituting T299 with a charged side chain chemistry such as D, E, K, or R. The resulting antibody will have reduced glycosylation as well as reduced Fc binding affinity to an Fc receptor due to unfavorable electrostatic interactions.

In another embodiment, a T299C variant antibody, which is both aglycosylated and capable of forming a cysteine adduct, may exhibit less effector function (e.g., FcγRI binding) compared to its aglycosylated antibody counterpart (see, e.g., WO 05/18572). Accordingly, alteration of a first amino acid proximal to a glycosylation motif can inhibit the glycosylation of the antibody at a second amino acid residue; when the first amino acid is a cysteine residue, the antibody may exhibit even further reduced effector function. In addition, inhibition of glycosylation of an antibody of the IgG4 subtype may have a more profound affect on FcγRI binding compared to the effects of agycosylation in the other subtypes.

In additional embodiments, the present invention relates to anti-CD154 antibodies with altered glycosylation that exhibit reduced binding to one or more FcR receptors and that optionally also exhibit increased or normal binding to one or more Fc receptors and/or complement—e.g., antibodies with altered glycosylation that at least maintain the same or similar binding affinity to one or more Fc receptors and/or complement as a native, control anti-CD154 antibody). For example, anti-CD154 antibodies with predominantly $Man_5GlcNAc_2N$-glycan as the glycan structure present (e.g., wherein $Man_5GlcNAc_2N$-glycan structure is present at a level that is at least about 5 more percent more than the next predominant glycan structure of the Ig composition) may exhibit altered effector function compared to an anti-CD154 antibody population wherein $Man_5GlcNAc_2N$-glycan structure is not predominant. Antibodies with predominantly this glycan structure exhibit decreased binding to FcγRIIa and FcγRIIb, increased binding to FcγRIIIa and FcγRIIIb, and increased binding to C1q subunit of the C1 complex (see US 2006-0257399). This glycan structure, when it is the predominant glycan structure, confers increased ADCC, increased CDC, increased serum half-life, increased antibody production of B cells, and decreased phagocytosis by macrophages.

In general, the glycosylation structures on a glycoprotein will vary depending upon the expression host and culturing conditions (Raju, T S. BioProcess *International* April 2003. 44-53). Such differences can lead to changes in both effector function and pharmacokinetics (Israel et al. Immunology. 1996; 89(4):573-578; Newkirk et al. P. Clin. Exp. 1996; 106 (2):259-64). For example, galactosylation can vary with cell culture conditions, which may render some immunoglobulin compositions immunogenic depending on their specific galactose pattern (Patel et al., 1992. *Biochem J*. 285: 839-845). The oligosaccharide structures of glycoproteins produced by non-human mammalian cells tend to be more closely related to those of human glycoproteins. Further, protein expression host systems may be engineered or selected to express a predominant Ig glycoform or alternatively may naturally produce glycoproteins having predominant glycan structures. Examples of engineered protein expression host systems producing a glycoprotein having a predominant glycoform include gene knockouts/mutations (Shields et al., 2002, *JBC*, 277: 26733-26740); genetic engineering in (Umana et al., 1999, *Nature Biotech.*, 17: 176-180) or a combination of both. Alternatively, certain cells naturally express a predominant glycoform—for example, chickens, humans and cows (Raju et al., 2000, *Glycobiology*, 10: 477-486). Thus, the expression of an anti-CD154 antibody or antibody composition having altered glycosylation (e.g., predominantly one specific glycan structure) can be obtained by one skilled in the art by selecting at least one of many expression host systems. Protein expression host systems that may be used to produce anti-CD154 antibodies of the present invention include animal, plant, insect, bacterial cells and the like. For example, US 2007-0065909, 2007-0020725, and 2005-0170464 describe producing aglycosylated immunoglobulin molecules in bacterial cells. As a further example, Wright and Morrison produced antibodies in a CHO cell line deficient in glycosylation (1994 *J Exp Med* 180: 1087-1096) and showed that antibodies produced in this cell line were incapable of complement-mediated cytolysis. Other examples of expression host systems found in the art for production of glycoproteins include: CHO cells: Raju WO 99/22764 and Presta WO 03/35835; hybridoma cells: Trebak et al., 1999, *J. Immunol. Methods*, 230: 59-70; insect cells: Hsu et al., 1997, *JBC*, 272:9062-970, and plant cells: Gerngross et al., WO 04/74499. To the extent that a given cell or extract has resulted in the glycosylation of a given motif, art recognized techniques for determining if the motif has been glycosylated are available, for example, using gel electrophoresis and/or mass spectroscopy.

Additional methods for altering glycosylation sites of antibodies are described, e.g., in U.S. Pat. No. 6,350,861 and U.S. Pat. No. 5,714,350, WO 05/18572 and WO 05/03175; these methods can be used to produce anti-CD154 antibodies of the present invention with altered, reduced, or no glycosylation.

The aglycosyl anti-CD154 antibodies with reduced effector function may be antibodies that comprise modifications or that may be conjugated to comprise a functional moiety. Such moieties include a blocking moiety (e.g., a PEG moiety, cysteine adducts, etc.), a detectable moiety (e.g., fluorescent moieties, radioisotopic moieties, radiopaque moieties, etc., including diagnostic moieties), and/or a therapeutic moiety (e.g., cytotoxic agents, anti-inflammatory agents, immunomodulatory agents, anti-infective agents, anti-cancer agents, anti-neurodegenerative agents, radionuclides, etc.).

Antibody Conjugates

When administered, antibodies are often cleared rapidly from the circulation and may therefore elicit relatively short-lived pharmacological activity. Consequently, frequent injections of relatively large doses of antibodies may be required to sustain the therapeutic efficacy of the antibody treatment.

In one embodiment of this invention, the anti-CD154 antibodies of this invention may be antibodies modified (e.g., attached to other moieties such a heterologous functional moiety) to increase the integrity and longevity of the antibody in vivo. For example, the anti-CD154 antibodies of this invention may be antibodies that are modified to include a moiety (functional moiety) that can increase stabilization, thereby prolonging the serum half-life of the antibody. The serum half life of a CD154 binding protein, e.g., antibody, of the invention may be at least 3 days, at least 7 days, at least 14 days, at least 21 days, at least 28 days, at least 1 month or more. Such functional moieties that increase the half-life of the antibodies may be particularly useful in embodiments where the antibody is an antibody fragment, for example.

Antibody modifications may also increase the protein's solubility in aqueous solution, eliminate aggregation, enhance the physical and chemical stability of the protein, and greatly reduce the immunogenicity and antigenicity of the protein. As a result, the desired in vivo biological activity may be achieved by the administration of such polymer-protein adducts less frequently or in lower doses than with the unmodified protein.

Accordingly, in certain embodiments, the antibodies of the invention are antibodies attached to heterologous functional moieties to form antibody conjugates. A "functional moiety" refers to any functional moiety (e.g., polypeptide, protein domain, carrier, polymer, etc.) that is associated with an antibody of the invention. Association with an anti-CD154 antibody may be by covalent or non-covalent attachment and may also be reversible or regulatable. Exemplary molecules that may be used to form CD154 antibody conjugates of the present invention include but are not limited to functional moieties such as, e.g., antineoplastic agents, drugs, toxins, biologically active proteins, for example enzymes, other antibody, antibody derivative or antibody fragments, synthetic (for example, PEG) or naturally occurring polymers, nucleic acids and fragments thereof, e.g. DNA, RNA and fragments thereof, aptamers, radionuclides, particularly radioiodide, radioisotopes, chelated metals, nanoparticles and reporter groups such as fluorescent or luminescent compounds or compounds which may be detected by imaging techniques such as NMR or ESR spectroscopy.

In a further example, a functional moiety to which the antibodies of the invention are conjugated may increase the half-life of the antibody in vivo, and/or reduce immunogenicity of the antibody and/or enhance the delivery of an antibody across an epithelial barrier to the immune system. Examples of suitable functional moieties of this type include polymers, dextran, hydroxypropylmethacrylamide (HPMA), transferrin, albumin, albumin binding proteins or albumin binding compounds such as those described in PCT/GB2005/002084.

Where the functional moiety is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide. See for example Veronese and Pasut, 2005, *Drug Discovery Today*, 10(21):1451-1458; Pasut et al., 2004, *Expert Opinion in Therapeutic Patents*, 14(6):859-894.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof. "Derivatives" in this context is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 Da to 40000 Da and more preferably from 20000 Da to 40000 Da. The polymer size may in particular be selected on the basis of the intended use of the product for example ability to localize to certain tissues such as tumors or extend circulating half-life (for a review see Chapman, 2002, *Advanced Drug Delivery Reviews*, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

Preferably, the antibody, antibody derivative or antibody fragment of this invention, including an antibody or fragment with reduced effector function, is attached to a polyalkylene polymer, particularly a poly(ethyleneglycol) (abbreviated herein to PEG) or a derivative thereof. In certain embodiments, the antibody, antibody derivative or antibody fragment of this invention is an antibody fragment that is a Fab' or F(ab')$_2$ fragment or a derivative thereof which is attached to PEG either on the heavy chain or the light chain or both. This Fab' or F(ab')$_2$ fragment thereof may be human or humanized.

Accordingly, in certain embodiments of this invention, the anti-CD154 antibodies of this invention are antibodies that are modified by covalent attachment of functional moieties such as water-soluble polymers, such as poly(ethyleneglycol), copolymers of poly(ethyleneglycol) and poly(propyleneglycol), carboxymethyl cellulose, dextran, poly(vinylalcohol), poly(vinylpyrrolidone) or poly(proline)—all of which are known to exhibit substantially longer half-lives in blood following intravenous injection than do the corresponding unmodified proteins. See, e.g., Abuchowski et al. 1981. In: "*Enzymes as Drugs*", Holcenberg et al. (ed.) 1981. Wiley-Interscience, New York, N.Y., 367-383 (1981); Anderson, W. F. 1992. Human Gene Therapy. *Science* 256:808-813; Newmark et al. 1982. *J. Appl. Biochem.* 4:185-189; Katre et al. 1987. *Proc. Natl. Acad. Sci. USA* 84:1487-1491.

In some embodiments, antibodies of the present invention are antibodies attached to functional moieties such as to poly(ethyleneglycol) (PEG) moieties. In one particular embodiment, the antibody is an antibody fragment and the PEG molecules may be attached through any available amino acid side-chain or terminal amino acid functional group located in the antibody fragment, for example, any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO 98/25971). In another embodiment, a Fab fragment of this invention is modified by the addition to the C-terminal end of its heavy chain one or more amino acids to allow the attachment of a functional moiety. Preferably, the additional amino acids form a modified hinge region containing one or more cysteine residues to which the functional moiety may be attached. Multiple sites can be used to attach two or more PEG molecules.

In certain aspects of this invention, PEG molecules are covalently linked through a thiol group of at least one cysteine residue located in an antibody fragment of this invention.

Each PEG molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated functional moieties, for example thiol selective derivatives such as maleimides and cysteine derivatives may be used. An activated PEG may be used as the starting material in the preparation of PEG-modified antibody fragments as described above. The activated PEG may be any PEG containing a thiol reactive group such as an α-halocarboxylic acid or ester, e.g. iodoacetamide, an imide, e.g. maleimide, a vinyl sulphone or a disulphide. In certain embodiments, an anti-CD154 antibody conjugate may comprise two PEG molecules with two maleimide molecules. Starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one preferred embodiment, an antibody of the invention is a modified Fab fragment which is PEGylated, i.e. has PEG (poly(ethyleneglycol)) covalently attached thereto, e.g. according to the method disclosed in EP 0948544 (see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, *Advanced Drug Delivery Reviews* 2002, 54:531-545). In one example PEG is attached to a cysteine in the hinge region. In another example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In another embodiment, the functional moiety is PEG and is attached using the methods described in WO 98/25971 and WO 04/72116, whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another embodiment, the functional moiety is PEG and is attached to a F(ab)$_2$ fragment using the methods described in WO 98/25971 and WO 04/072116, whereby a lysyl-dimaleimide group is attached to the cysteine residue at the C-terminal end of each Fab heavy chain, and each amino group of the lysyl residue has covalently linked to it a methoxypoly(ethyleneglycol) residue having a molecular weight of about 20,000 Da. The total molecular weight of the PEG attached to the F(ab)$_2$ antibody is therefore approximately 40,000 Da.

In certain embodiments of this invention, the antibody of this invention is a Fab' antibody fragment, which may be fully human or humanized, and is PEGylated either in the heavy chain, the light chain or both. In other embodiments, the antibody fragment, which may be fully human or humanized, is PEGylated on one or both heavy chains, or on one or both light chains, or on both heavy and light chains.

Accordingly, in certain embodiments, an anti-CD154 antibody is a PEG-linked antibody (e.g., a PEG-linked human antibody) wherein the PEG is linked to the antibody at a cysteine or at a lysine residue. In certain embodiments, the PEGylated anti-CD154 antibody has a hydrodynamic size of at least 24 kD. In other embodiments, the PEG may vary in size from anywhere between 20 to 60 kD (inclusive). In further embodiments, the PEG-linked anti-CD154 antibody has a hydrodynamic size of at least 200 kD. In embodiments of the present invention where the anti-CD154 antibody is linked to a PEG moiety, the PEGylated anti-CD154 antibody may have an increased in vivo half-life relative to an anti-CD154 antibody that lacks the PEG moiety.

In certain embodiments, this invention provides a CD154 binding protein comprising a light chain sequence of SEQ ID NO: 15 and a heavy chain sequence of SEQ ID NO: 13, wherein the protein is PEGylated.

Other functional moieties that may be useful in improving the integrity and longevity of the antibodies of the present invention in vivo include polypeptides. For example, the anti-CD154 antibodies or antibody fragments of this invention may be modified to include a human serum albumin (HSA) polypeptide. Such an antibody conjugate may exhibit increased stabilization and increased serum half-life compared to a non-conjugated antibody or antigen-binding fragment. For example, in certain embodiments, an anti-CD154 antibody conjugated to HSA may exhibit increased in vivo half-life relative to a non-conjugated anti-CD154 antibody. The half-life (tα- or tβ-half life) of the HSA-conjugated antibody may be increased by 10%, 20%, 30%, 40%, 50% or more. The α-half life may be within the range of 0.25 minutes to 12 hours, for example, while the tβ-half life may be within 12-48 hours, for example. The tα- or tβ-half life may preferably be at least 3 days, at least 7 days, at least 14 days, at least 21 days, at least 28 days, least 1 month or more.

In some embodiments of this invention, the anti-CD154 antibodies of this invention are antibodies modified with a functional moiety by labeling with a detectable marker, for example, a radioactive isotope, enzyme, dye or biotin, or other affinity reagent.

In some embodiments of this invention, the anti-CD154 antibodies of this invention are antibodies modified with a functional moiety by being conjugated to a therapeutic agent, for example, a radioisotope or radionuclide (e.g., 111In or 90Y), toxin moiety (e.g., tetanus toxoid or ricin), toxoid or chemotherapeutic agent (U.S. Pat. No. 6,307,026).

In some embodiments of this invention, the anti-CD154 antibodies of this invention are antibodies modified by being conjugated to an imaging agent. Imaging agents may include for example a labeling moiety (e.g., biotin, fluorescent moieties, radioactive moieties, a histidine or myc tag or other peptide tags) for easy isolation or detection.

Further examples of functional moieties for modification of or conjugation to anti-CD514 antibodies of the invention, may include serotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Functional moieties useful in conjugation include, but are not limited to, anti-folates (e.g. aminopterin and methotrexate), antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins, CC-1065, enedieyenes, neocarzinostatin), and anti-mitotic agents (e.g. vincristine and vinblastine). See Garnett, 2001, *Advanced Drug Delivery Reviews*, 53:171-216 for further details.

Other functional moieties may include chelated radionuclides such as $^{131}$I, $^{111}$In and $^{90}$Y, Lu$^{177}$, Bismuth$^{213}$, Californium$^{252}$, Iridium$^{192}$ and Tungsten$^{188}$/Rhenium$^{188}$, $^{211}$astatine; or drugs such as but not limited to, alkylphosphocholines, topoisomerase I inhibitors, taxoids and suramin.

Further functional moieties include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a maytansinoid (for example, but not limited to, DM1), a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, angiogenin, gelonin, dolstatins, minor groove binders, bisido-phenol mustard, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Other functional moieties may include detectable substances useful, for example, in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions that can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

Nucleic Acids

In certain aspects, the present invention relates to nucleic acids encoding CD154 binding proteins, e.g., anti-CD154 antibodies, of the present invention.

Accordingly, in certain embodiments the present invention relates to an isolated, recombinant and/or synthetic DNA molecule that comprises one or more sequence(s) selected from the group consisting of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 31, SEQ ID NO: 32, SEQ ID NO: 33, SEQ ID NO: 34, SEQ ID NO: 41, SEQ ID NO: 55, SEQ ID NO: 57, SEQ ID NO: 59, SEQ ID NO: 61, SEQ ID NO: 67, SEQ ID NO: 70 and SEQ ID NO: 73.

In another aspect, the disclosure features an isolated nucleic acid that comprises one or more sequence(s) that encode a polypeptide that includes a sequence at least 80, 85, 90, 92, 94, 95, 96, 97, 98, 99, or 100% identical to the sequence of a variable domain sequence of SEQ ID NO: 1, SEQ ID NO: 2; SEQ ID NO: 9, SEQ ID NO: 10, SEQ ID NO: 11, SEQ ID NO: 14; SEQ ID NO: 29, SEQ ID NO: 30, SEQ ID NO: 54, SEQ ID NO: 56, SEQ ID NO: 58 or SEQ ID NO: 60 or a sequence that hybridizes (e.g., under stringent conditions) to a nucleic acid encoding the sequence of a variable domain of SEQ ID NO: 1, SEQ ID NO: 9, SEQ ID NO: 10, SEQ ID NO: 11, SEQ ID NO: 29, SEQ ID NO: SEQ ID NO: 56 or SEQ ID NO: 60.

The nucleic acids of the invention may further include regulatory sequences (e.g., a promoter sequence, an untranslated 5' region, and an untranslated 3' region) and/or vector sequences. For example, the nucleic acid constitutes a vector. In still further embodiments, the invention relates to a host cell comprising the vector. The host cell may produce the antibody so that the antibody exhibits reduced or no glycosylation (e.g., if an Fc region is present).

The present invention also relates to sequence variants of the nucleic acids described above. For example, the present invention includes nucleic acid sequences that are about 75%, about 80%, about 85%, about 90%, about 91%, about 92%, about 93%, about 94%, about 95%, about 96%, about 97%, about 98%, about 99%, 99.5%, 99.9% or 100% identical to any of the sequences provided herein, including fragments thereof and complements thereto. The present invention also includes nucleic acids that vary from the sequences specifically provided herein due to the degeneracy of the genetic code.

Further, the present invention includes sequences that specifically hybridize to any of the nucleic acids provided herein. The term "specifically hybridizes" refers to the ability of a nucleic acid sequence to hybridize to at least 12, 15, 20, 25, 30, 35, 40, 45, 50 or 100 consecutive nucleotides of a sequence provided herein, or a sequence complementary thereto, such that it has less than 15%, preferably less than 10%, and more preferably less than 5% background hybridization to a control nucleic acid (e.g., a non-specific DNA or DNA other than the specific antibody sequence provided herein). A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C.

The nucleic acids encoding the CD154 binding proteins of the present invention may comprise leader or signal sequences. Leader and signal sequence can vary and may be substituted with an alternative leader sequence, and it is understood that, in certain embodiments, CD154 binding proteins of the present invention comprise sequences without a leader sequence. Any suitable alternative leader or signal sequences may be used.

Host Cells

The present invention relates to host cells engineered to express any of the DNA molecules provided in FIGS. 2-8, 10, 11 and 13-16, including sequence variants thereof.

Host cells expressing the CD154 binding proteins, e.g., anti-CD154 antibodies, of this invention are also provided. Whether a binding protein or an antibody, it may comprise only one chain, in which case, only the DNA sequence encoding that polypeptide chain need be used to transfect the cells. For the production of antibodies comprising two chains, the cell line may be transfected with two vectors. Alternatively, when appropriate, a single vector may encode both chain sequences, e.g. the light and heavy chain of an anti-CD154 antibody, and variations depending on the particular antibody structure to be expressed. The host cell may be, for example, prokaryotic cells such as *E. coli*, or other microbial cells, or eukaryotic cells including but not limited to mammalian cells such as human, mouse, monkey, rabbit, goat, hamster, or rat cells, insect cells, avian cells, plant cells and lower eukaryotic cells such as fungal cells (see below). It is understood that the host cell machinery is responsible for glycosylating recombinantly expressed proteins and thus particular glycosylation patterns can be selected to further alter effector function of antibodies of the invention.

In some embodiments of this invention, the host cells useful for practicing the invention may be, for example, (1) bacterial cells, such as *E. coli, Caulobacter crescentus*, Streptococci, Staphylococci, *Streptomyces* species and *Bacillus subtilis* cells, and *Salmonella typhimurium*; (2) fungal cells and *Aspergillus* cells, yeast cells, such as *Saccharomyces cerevisiae, Schizosaccharomyces pombe, Pichia pastoris, Pichia methanolica*, other *Pichia* species, *K. lactis* (3) insect cell lines, such as those from *Spodoptera frugiperda*—e.g., Sf9 and Sf21 cell lines, and expresSF™ cells (Protein Sciences Corp., Meriden, Conn., USA)—*Drosophila* S2 cells, and *Trichoplusia ni* High Five® Cells (Invitrogen, Carlsbad, Calif., USA); (4) mammalian cells, or (5) plant cells.

Accordingly, the CD154 binding proteins, e.g., anti-CD154 antibodies, of this invention may be produced in any available prokaryotic or eukaryotic host cells capable of being engineered to express exogenous nucleic acid sequences. Lower eukaryotic host cells that may be used to produce anti-CD154 antibodies of the present invention include those cells described in the art (see, e.g., WO 02/00879, WO 03/056914, WO 04/074498, WO 04/074499, Choi et al., 2003, *PNAS,* 100: 5022-5027; Hamilton et al., 2003, *Nature,* 301: 1244-1246 and Bobrowicz et al., 2004, *Glycobiology,* 14: 757-766).

Typical mammalian cells include COS1 and COS7 cells, Chinese hamster ovary (CHO) cells, NS0 myeloma cells, NIH 3T3 cells, 293 cells, HEPG2 cells, HeLa cells, C127, 3T3, BHK, Bowes melanoma cells, L cells, MDCK, HEK293, WI38, murine ES cell lines (e.g., from strains 129/SV, C57/BL6, DBA-1, 129/SVJ), K562, Jurkat cells, and BW5147. The invention thus provides cells that express the antibodies of the present invention, including but not limited to hybridoma cells, B cells, plasma cells, as well as mammalian and human host cells recombinantly modified to express the antibodies of the present invention (e.g., adult embryonic stem cells). Other useful mammalian cell lines are well known and readily available from the American Type Culture Collection ("ATCC") (Manassas, Va., USA) and the National Institute of General Medical Sciences (NIGMS) Human Genetic Cell Repository at the Coriell Cell Repositories (Camden, N.J., USA). These cell types are only representative, and this list is not meant to be an exhaustive list.

Among other considerations, some of which are described above, a host cell may be chosen for its ability to process the expressed anti-CD154 antibody in the desired fashion. In addition to modified glycosylation and aglycosylation, such post-translational modifications of the polypeptide include, but are not limited to, acetylation, carboxylation, carboxymethylation, phosphorylation, lipidation, and acylation.

In another embodiment of this invention, the anti-CD154 antibodies of this invention are prepared by cell free translation or synthesized in vitro. The genes that encode for these proteins may be synthesized in vitro.

In another embodiment, the anti-CD154 antibodies of this invention are produced in bioreactors containing the antibody-expressing cells, in order to facilitate large scale production.

In another embodiment, the CD154 binding proteins or anti-CD154 antibodies of this invention are produced in genetically engineered or transgenic mammals (e.g., goats, cows, sheep) that express the antibody in milk, in order to facilitate large scale production of the anti-CD154 antibodies (U.S. Pat. No. 5,827,690; Pollock et al. 1999. *J. Immunol. Meth.* 231(1-2):147-57).

Therapeutic Methods

In one embodiment of this invention, a CD154 binding protein, e.g., an anti-CD154 antibody, or a pharmaceutical composition comprising the antibody, is capable of inhibiting an immune response in a subject. The antibody of this invention, or pharmaceutical composition of the invention, is administered to the subject in an effective inhibiting amount.

In certain embodiments, an "effective inhibiting amount" of an anti-CD154 antibody, or pharmaceutical composition comprising the antibody, is any amount which is effective to inhibit the CD154-CD40 interaction in the subject to whom it is administered. Methods of determining an "inhibiting amount" are well known to those skilled in the art and depend upon factors including, but not limited to: the type of subject involved, the size and age of the subject and the pharmacokinetic properties of the particular therapeutic agent delivered.

In another specific embodiment of this invention, a CD154 binding protein, e.g., an anti-CD154 antibody, of this invention, or a pharmaceutical composition comprising the antibody, is capable of inhibiting the immune response by inhibiting the CD154-CD40 interaction.

In one embodiment of this invention, a CD154 binding protein, e.g., an anti-CD154 antibody, of this invention, or a pharmaceutical composition comprising the antibody, is capable of inhibiting inflammation. For the purposes of this invention, inflammatory responses are characterized by redness, swelling, heat and pain, as consequences of capillary dilation with edema and migration of phagocytic leukocytes. Some examples of inflammatory responses include: arthritis, contact dermatitis, hyper-IgE syndrome, inflammatory bowel disease, allergic asthma, and idiopathic inflammatory disease. Idiopathic inflammatory disease includes, for example, psoriasis and lupus (e.g., systemic lupus erythematosus (SLE), drug-induced lupus erythematosus, and lupus nephritis). See, e.g., Gallin 1989. *Fundamental Immunology*, Chapter 26, Raven Press, 2d Ed., pp. 721-733, New York. This invention provides a method of treating or preventing a symptom of systemic lupus erythematosus (SLE) in an individual, the method comprising administering a monovalent CD154 binding protein, e.g., a monovalent anti-CD154 antibody to an individual in an amount effective to treat or prevent a symptom of SLE.

Some examples of arthritis include: rheumatoid arthritis, non-rheumatoid inflammatory arthritis, arthritis associated with Lyme disease and inflammatory osteoarthritis. Some examples of idiopathic inflammatory disease include: psoriasis and systemic lupus.

In one embodiment of this invention, an anti-CD154 antibody, or a pharmaceutical composition comprising the antibody, is capable of inhibiting rejection by the subject of a transplanted organ.

In a more specific embodiment of this invention, a CD154 binding protein, e.g., an anti-CD154 antibody of this invention, or a pharmaceutical composition comprising the antibody, is capable of inhibiting rejection by the subject of a transplanted heart, kidney, liver, skin, pancreatic islet cells or bone marrow.

In one embodiment of this invention, a CD154 binding protein, e.g., an anti-CD154 antibody, or a pharmaceutical composition comprising the antibody, is capable of inhibiting graft-vs-host disease in a subject.

In one embodiment of this invention, a CD154 binding protein, e.g., an anti-CD154 antibody, or a pharmaceutical composition comprising the antibody, is capable of inhibiting allergic responses, in a subject—for example, hay fever or an allergy to penicillin or other drugs.

In one embodiment of this invention, a CD154 binding protein, e.g., an anti-CD154 antibody, of this invention, or a pharmaceutical composition comprising the antibody, is capable of inhibiting the autoimmune response in subject suffering from autoimmune disease. In some embodiments, the autoimmune response is associated with or is derived from a condition selected from the group consisting of: rheumatoid arthritis, Myasthenia gravis, systemic lupus erythematosus, Graves' disease, idiopathic thrombocytopenia purpura, hemolytic anemia, diabetes mellitus, inflammatory bowel disease, Crohn's disease, multiple sclerosis, psoriasis, drug-induced autoimmune diseases, or drug-induced lupus. In certain embodiments, the autoimmune response is associated with or derived from systemic lupus erythematosus.

In one embodiment of this invention, a CD154 binding protein, e.g., an anti-CD154 antibody, of this invention, or a pharmaceutical composition comprising the antibody, is capable of inhibiting an autoimmune response in a subject suffering from an autoimmune response which is derived from an infectious disease.

In one embodiment of this invention, a CD154 binding protein, e.g., an anti-CD154 antibody, of this invention, or a pharmaceutical composition comprising the antibody, is capable of inhibiting an autoimmune response in a subject suffering from an autoimmune response which is derived from Reiter's syndrome, spondyloarthritis, Lyme disease, HIV infection, syphilis, or tuberculosis.

In one embodiment of this invention, a CD154 binding protein, e.g., an anti-CD154 antibody, of this invention, or a pharmaceutical composition comprising the antibody, is capable of inhibiting fibrosis in a subject.

Some examples of fibrosis include: pulmonary fibrosis or fibrotic disease. Some examples of pulmonary fibrosis include: pulmonary fibrosis secondary to adult respiratory distress syndrome, drug-induced pulmonary fibrosis, idiopathic pulmonary fibrosis, or hypersensitivity pneumonitis. Some examples of fibrotic diseases include: Hepatitis-C; Hepatitis-B; cirrhosis; cirrhosis of the liver secondary to a toxic insult; cirrhosis of the liver secondary to drugs; cirrhosis of the liver secondary to a viral infection; and cirrhosis of the liver secondary to an autoimmune disease.

In one embodiment of this invention, a CD154 binding protein, e.g., an anti-CD154 antibody, of this invention, or a pharmaceutical composition comprising the antibody, is capable of inhibiting gastrointestinal disease. Some examples of gastrointestinal disease include: esophageal dysmotility, inflammatory bowel disease (including Crohn's disease and ulcerative colitis), gastritis, collagenous colitis (including lymphocytic colitis and microscopic colitis), coeliac disease (also called gluten enteropathy, coeliac sprue, or gluten intolerance), and scleroderma.

In one embodiment of this invention, a CD154 binding protein, e.g., an anti-CD154 antibody, of this invention, or a pharmaceutical composition comprising the antibody, is capable of inhibiting vascular disease. Some examples of vascular disease include: atherosclerosis, renal artery disease, lymphedema, ischemic disorders, and reperfusion injury. Also included are collagen vascular/immune complex diseases such as systemic lupus erythematosis or cryoglobulinemia.

In one embodiment of this invention, a CD154 binding protein, e.g., an anti-CD154 antibody, of this invention, or a pharmaceutical composition comprising the antibody, is capable of inhibiting the proliferation of T cell tumor cells in a subject suffering from a T cell cancer,—e.g., a T cell leukemia or lymphoma. Such an anti-CD154 antibody, or a pharmaceutical composition comprising the antibody, may be administered to the subject in an amount effective to inhibit the proliferation of T cell tumor cells in that subject.

In one embodiment of this invention, a CD154 binding protein, e.g., an anti-CD154 antibody, of this invention, or a pharmaceutical composition comprising the antibody, is capable of inhibiting viral infection of the T cells of a subject by the human T-cell lymphotropic virus type 1 (HTLV I). Such an anti-CD154 antibody or a pharmaceutical composition comprising the antibody may be administered to the subject in an amount effective to inhibit viral infection.

In one embodiment of this invention, a CD154 binding protein, e.g., an anti-CD154 antibody, of this invention, or a pharmaceutical composition comprising the antibody, is capable imaging tumor cells or neoplastic cells in a subject that express a CD154 protein to which the antibody of this invention specifically binds. A method for imaging tumor cells or neoplastic cells in a subject comprises the steps of: administering to the subject an effective amount of an anti-CD154 antibody of this invention, or a composition comprising it, under conditions permitting the formation of a complex between the antibody and a protein on the surface of tumor cells or neoplastic cells; and imaging any antibody/protein complex formed, thereby imaging any tumor cells or neoplastic cells in the subject.

In one embodiment of this invention, a CD154 binding protein, e.g., an anti-CD154 antibody of this invention, or a pharmaceutical composition comprising the antibody, is capable of detecting the presence of tumor cells or neoplastic cells in a subject that express a CD154 protein to which the antibody of this invention specifically binds. One such method for detecting the presence of tumor cells or neoplastic cells in a subject comprises the steps of: administering to the subject an effective amount of an anti-CD154 antibody of this invention, or a pharmaceutical composition comprising it, under conditions permitting the formation of a complex between the antibody and a protein; clearing any unbound imaging agent from the subject; and detecting the presence of any antibody/protein complex formed, the presence of such complex indicating the presence of tumor cells or neoplastic cells in the subject.

Pharmaceutical Compositions

This invention provides pharmaceutical compositions comprising a CD154 binding protein, e.g., an anti-CD154 antibody, as described in this invention.

In one embodiment of this invention, the pharmaceutical composition comprises at least one CD154 binding protein, e.g., anti-CD154 antibody, of this invention.

In one embodiment of this invention, an aglycosyl anti-CD154 antibody (or other anti-CD154 antibody with reduced effector function) of the invention, or pharmaceutical composition comprising the antibody, is capable of binding to a CD154 antigen (e.g., the CD154 antigen that is specifically bound by aglycosyl hu5c8 produced by the cell line having ATCC Accession No. PTA-4931), and wherein the aglycosyl anti-CD154 antibody is characterized by having a mutation of N298Q (N297 using EU Kabat numbering) and which further exhibits reduced effector function as described elsewhere herein.

In certain embodiments of this invention, an aglycosyl anti-CD154 antibody (or other anti-CD154 antibody with reduced effector function), or pharmaceutical composition comprising the antibody, does not bind to an effector receptor. In a more specific embodiment, an aglycosyl anti-CD154 antibody, or pharmaceutical composition comprising the antibody, is capable of binding to the CD154 protein that is specifically bound by aglycosyl hu5c8 produced by the cell line having ATCC Accession No. PTA-4931, and wherein the aglycosyl anti-CD154 antibody or pharmaceutical composition does not bind to an effector receptor.

In a specific embodiment of this invention, an aglycosyl anti-CD154 antibody (or other anti-CD154 antibody or CD154 binding protein with reduced effector function), or pharmaceutical composition comprising the antibody, does not cause thrombosis, including thromboembolic events. In a more specific embodiment of this invention, an aglycosyl anti-CD 154 antibody or pharmaceutical composition comprising the antibody is capable of binding to the CD154 protein that is specifically bound by aglycosyl hu5c8 produced by the cell line having ATCC Accession No. PTA-4931, and wherein the aglycosyl anti-CD154 antibody or pharmaceutical composition does not cause thrombosis.

In another embodiment of this invention, the pharmaceutical compositions may further comprise any one or more of a pharmaceutically acceptable carrier, an adjuvant, a delivery vehicle, a buffer and/or a stabilizer. Exemplary techniques for formulation and administration of the antibodies of the present invention may be found, for example, in "Remington's Pharmaceutical Sciences," Mack Publishing Co., Easton, Pa., latest edition.

In a more particular embodiment of this invention, the pharmaceutically acceptable carrier is phosphate buffered saline, physiological saline, water, citrate/sucrose/Tween formulations and emulsions—e.g., oil/water emulsions.

In one embodiment of this invention, the pharmaceutical composition may be delivered in a microencapsulation device so as to reduce or prevent a host immune response against the composition. The binding agents, such as antibodies or antibody fragments of this invention, may also be delivered microencapsulated in a membrane, such as, for example, a liposome or other encapsulated or immunoprotected delivery vehicle.

In one embodiment of this invention, the pharmaceutical composition may be in the form of a sterile injectable preparation, for example, a sterile injectable aqueous or oleaginous suspension. This suspension may be formulated according to techniques known in the art using suitable dispersing, wetting, and suspending agents.

In one embodiment of this invention, the pharmaceutical composition may be delivered orally, topically or intravenously. When administered systemically, the therapeutic composition should be sterile, substantially pyrogen-free and in a parenterally acceptable solution having due regard for pH, isotonicity, and stability. For example, a pharmaceutical preparation is substantially free of pyrogenic materials so as to be suitable for administration as a human therapeutic. These conditions are known to those skilled in the art.

In a more specific embodiment of this invention, for oral administration, the pharmaceutical composition is formulated in a suitable capsule, tablet, aqueous suspension or solution. Solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate, and alginic acid. Tablet binders that can be used include acacia, methylcellulose, sodium carboxymethylcellulose, polyvinylpyrrolidone (Povidone™), hydroxypropyl methylcellulose, sucrose, starch, and ethylcellulose. Lubricants that can be used include magnesium stearates, stearic acid, silicone fluid, talc, waxes, oils, and colloidal silica.

In a more specific embodiment of this invention, for topical applications, the pharmaceutical compositions may be formulated in a suitable ointment. Some examples of formulations of a composition for topical use include: drops, tinctures, lotions, creams, solutions, and ointments containing the active ingredient and various supports and vehicles.

In one embodiment of this invention, a topical semi-solid ointment formulation typically comprises a concentration of the active ingredient from about 1 to 20%, —e.g., 5 to 10%, in a carrier, such as a pharmaceutical cream base.

In one embodiment of this invention, pharmaceutical compositions for inhalation and transdermal compositions can also readily be prepared. The therapeutic composition can be administered through the nose or lung, for example, as a liquid or powder aerosol (lyophilized).

In one embodiment of this invention, liquid formulations of a pharmaceutical composition for oral administration prepared in water or other aqueous vehicles can contain various suspending agents such as methylcellulose, alginates, tragacanth, pectin, kelgin, carrageenan, acacia, polyvinylpyrrolidone, and polyvinyl alcohol. Liquid formulations of pharmaceutical compositions of this invention can also include solutions, emulsions, syrups and elixirs containing, together with the active compound(s), wetting agents, sweeteners, and coloring and flavoring agents. Various liquid and powder formulations of the pharmaceutical compositions can be prepared by conventional methods for inhalation into the lungs of the mammal to be treated.

In one embodiment of this invention, liquid formulations of a pharmaceutical composition for injection can comprise various carriers such as vegetable oils, dimethylacetamide, dimethylformamide, ethyl lactate, ethyl carbonate, isopropyl myristate, ethanol, polyols—i.e., glycerol, propylene glycol, liquid polyethylene glycol, and the like. In some embodiments, the composition includes a citrate/sucrose/Tween carrier. For intravenous injections, water soluble versions of the compositions can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. A suitable insoluble form of the composition can be prepared and administered as a suspension in an aqueous base or a pharmaceutically acceptable oil base, such as an ester of a long chain fatty acid—e.g., ethyl oleate.

In one embodiment of this invention, the pharmaceutical composition comprises from about 0.1 to 90% by weight (such as 1 to 20% or 1 to 10%) of an anti-CD154 antibody of this invention, in a pharmaceutically acceptable carrier.

In one embodiment of this invention, the optimal percentage of the anti-CD154 antibody of this invention in each pharmaceutical composition varies according to the formulation itself and the therapeutic effect desired in the specific pathologies and correlated therapeutic regimens. Pharmaceutical formulation is well-established in the art. Conventional methods, known to those of ordinary skill in the art of medicine, can be used to administer the pharmaceutical composition to the subject.

Accordingly, pharmaceutical compositions of the present invention relate to extended release formulations. Extended release, or controlled release or slow release, refers to drug formulations that release active drug, such as a polypeptide or antibody drug, over a period of time following administration to a subject. Extended release of polypeptide drugs, which can occur over a range of desired times (e.g., minutes, hours, days, weeks or longer, depending upon the drug formulation) differs from standard formulations in which substantially the entire dosage unit is available for immediate absorption or immediate distribution via the bloodstream. Extended release formulations may, in certain embodiments, result in a level of circulating drug from a single administration that is sustained, for example, for 8 hours or more, 12 hours or more, 24 hours or more, 36 hours or more, 48 hours or more, 60 hours or more, 72 hours or more 84 hours or more, 96 hours or more, or even, for example, for 1 week or 2 weeks or more, for example, 1 month or more. Extended release compositions may comprise a monovalent anti-CD154 antibody of the present invention. In further embodiments, the monovalent antibody is a humanized or a fully human antibody. In further embodiments, the anti-CD154 antibody, the anti-CD154 antibody is an antibody with reduced effector function as described herein.

In some embodiments of this invention, the pharmaceutical composition further comprises an immunosuppressive or immunomodulatory compound. For example, such an immunosuppressive or immunomodulatory compound may be one of the following: an agent that interrupts T cell costimulatory signaling via CD28; an agent that interrupts calcineurin signaling, a corticosteroid, an anti-proliferative agent, and an antibody that specifically binds to a protein expressed on the surface of immune cells, including but not limited to CD45, CD2, IL2R, CD4, CD8 and RANK FcR, B7, CTLA4, TNF, LTβ, and VLA-4.

In a some embodiments of this invention, the immunosuppressive or immunomodulatory compound is tacrolimus, sirolimus, mycophenolate mofetil or its active form mycophenolic acid, mizorubine, deoxyspergualin, brequinar sodium, leflunomide, rapamycin or azaspirane.

In other embodiments of this invention, antibodies of this invention or pharmaceutical compositions comprising them may be included in a container, package or dispenser alone or as part of a kit with labels and instructions for administration.

Administration and Delivery Routes

The anti-CD154 antibodies of this invention and pharmaceutical compositions of this invention may be administered to a subject in any manner which is medically acceptable. For the purposes of this invention, "administration" means any of the standard methods of administering an antibody, antibody fragment or pharmaceutical composition known to those skilled in the art, and should not be limited to the examples provide herein.

In some embodiments of this invention, the anti-CD154 antibodies of this invention and pharmaceutical compositions of this invention may be administered to a subject by injection intravenously, subcutaneously, intraperitoneally, intramuscularly, intramedullarily, intraventricularly, intraepidurally, intraarterially, intravascularly, intra-articularly, intra-synovially, intrasternally, intrathecally, intrahepatically, intraspinally, intratumorally, intracranially; by enteral, intrapulmonary, transmucosal, intrauterine, or sublingual routes of administration, or locally, e.g., at sites of inflammation or tumor growth.

In some embodiments of this invention, the anti-CD154 antibodies of this invention and pharmaceutical compositions of this invention may be administered to a subject orally or nasally, or by inhalation, ophthalmic, rectal, or topical routes.

In a more specific embodiment, the anti-CD154 antibodies of this invention, and pharmaceutical compositions of this invention may be administered to a subject orally in the form of capsules, tablets, aqueous suspensions or solutions.

In a more specific embodiment, the anti-CD154 antibodies of this invention and pharmaceutical compositions of this invention may be administered to a subject topically by application of a cream, ointment or the like.

In other embodiments of this invention, the anti-CD154 antibodies of this invention, and pharmaceutical compositions of this invention may also be administered by inhalation through the use of a nebulizer, a dry powder inhaler or a metered dose inhaler.

In further embodiments of this invention, the anti-CD154 antibodies of this invention, and pharmaceutical compositions of this invention may be administered to a subject by sustained release administration, by such means as depot injections of erodible implants directly applied during surgery or by implantation of an infusion pump or a biocompatible sustained release implant into the subject.

In a more specific embodiment, the anti-CD154 antibodies of this invention, and pharmaceutical compositions of this invention may be administered to a subject by injectable depot routes of administration, such as by using 1-, 3-, or 6-month depot injectable or biodegradable materials and methods.

In a more specific embodiment, the anti-CD154 antibodies of this invention, and pharmaceutical compositions of this invention may be administered to a subject by applying to the skin of the subject a transdermal patch containing the antibody, antibody derivative or pharmaceutical composition, and leaving the patch in contact with the subject's skin, generally for 1 to 5 hours per patch.

In other embodiments of this invention, the anti-CD154 antibodies of this invention, and pharmaceutical compositions of this invention may be administered to a subject at any dose per body weight and any dosage frequency that is medically acceptable. Acceptable dosage includes a range of between about 0.01 and 200 mg/kg subject body weight.

In any of the methods of using the antibodies or pharmaceutical compositions of this invention, the antibodies or pharmaceutical compositions may be administered to a subject in single or multiple doses daily, every 2, 3, 4, 5 or 6 days, weekly, monthly or any fraction or multiple thereof, and further may be administered to a subject repeatedly at intervals ranging from each day to every other month, as determined by the skilled practitioner.

In any of the methods of using the antibodies or pharmaceutical compositions of this invention, the binding proteins, antibodies or pharmaceutical compositions comprising them, may be administered to a subject in need thereof at intervals for as long a time as medically indicated, ranging from days or weeks to the life of the subject. In further embodiments, the anti-CD154 antibodies of this invention, and pharmaceutical compositions of this invention may be administered to a subject repeatedly at intervals ranging from each day to every other month.

In one embodiment of this invention, the anti-CD154 antibodies of this invention, and pharmaceutical compositions of this invention can be administered in multiple doses per day, if desired, to achieve the total desired daily dose. The effectiveness of the method of treatment can be assessed by monitoring the subject for known signs or symptoms of a disorder.

For all embodiments of this invention, the dosage and dose rate of the anti-CD154 antibodies of this invention and pharmaceutical compositions of this invention effective to produce the desired effects will depend on a variety of factors, such as the nature of the disease to be treated, the size and age of the subject, the goal of the treatment, the specific pharmaceutical composition used, the pharmacokinetics of the active agent, and the judgment of the treating physician.

Accordingly, anti-CD154 antibodies of this invention, and pharmaceutical compositions of this invention, will be administered in an amount effective to achieve their intended purpose. A therapeutically effective amount may refer to an amount of antibody effective to prevent, alleviate or ameliorate symptoms of disease or prolong the survival of the subject being treated. A therapeutically effective amount may be achieved by altering the dose and dosing schedule of administration of the subject antibodies.

The anti-CD154 antibodies of this invention, and pharmaceutical compositions of this invention may be administered as a single dosage for certain indications, such as preventing immune response to an antigen to which a subject is exposed for a brief time, such as an exogenous antigen administered on a single day of treatment. Examples of such a therapy would include coadministration of the antibody fragment of the invention along with a therapeutic agent, for example an antigenic pharmaceutical, an allergen or a blood product, or a gene therapy vector. In indications where antigen is chronically present, such as in controlling immune reaction to transplanted tissue or to chronically administered antigenic pharmaceuticals, the antibody fragments or pharmaceutical compositions of the invention are administered at intervals for as long a time as medically indicated, ranging from days or weeks to the life of the subject.

In any of the methods described herein, the antibodies or pharmaceutical compositions may be administered to a subject with a second agent. In certain embodiments, the agent is a therapeutic agent, such as, for example, an immunomodulatory or immunosuppressive agent. The immunomodulatory or immunosuppressive agent may be any of the following:
(a) an agent that interrupts T cell costimulatory signaling via CD28;
(b) an agent that interrupts calcineurin signaling,
(c) a corticosteroid,
(d) an anti-proliferative agent; and
(e) an antibody that specifically binds to a protein expressed on the surface of immune cells, including but not limited to CD45, CD2, IL2R, CD4, CD8 and RANK FcR, B7, CTLA4, TNF, LTβ, and VLA-4. The immunosuppressive or immunomodulatory compound may be, for example, tacrolimus, sirolimus, mycophenolate mofetil, mizorubine, deoxyspergualin, brequinar sodium, leflunomide, rapamycin or azaspirane. The antibody and second agent may be administered simultaneously or sequentially.

In some instances, it may be advantageous to administer one or more nucleic acids of the invention to a subject in need thereof. Therapeutic and diagnostic methods of the invention comprising the step of administering at least one nucleic acid of the invention according to well known methods are included in the scope of the present invention.

In one embodiment of this invention, the subject(s) that can be treated by the above-described methods is an animal. Preferably, the animal is a mammal. Examples of mammals that may be treated include, but are not limited to, humans, non-human primates, rodents (including rats, mice, hamsters and guinea pigs) cows, horses, sheep, goats, pigs, dogs and cats. Preferably, the mammal is a human.

This invention may be better understood based on the Examples that follow. However, one skilled in the art will readily appreciate that the specific methods and results discussed are merely illustrative of the invention as described herein.

EXAMPLES

The following examples illustrate the methods and products of the present invention. Suitable modifications and adaptations of the described conditions and parameters normally encountered in the art of molecular biology that are apparent to those skilled in the art are within the spirit and scope of the present invention.

Example 1

Generating Anti-Human-CD154 Antibodies by Slam

Selected Lymphocyte Antibody Method (SLAM) (Babcook et al., 1996, *Proc. Natl. Acad. Sci*, 93, 7843-7848; WO 92/02551; de Wildt et al., 1997, *J. Immunol. Methods*, 207: 61-67 and Lagerkvist, et al., 1995, *BioTechniques* 18:862-869) was used to identify and isolate anti-human CD154 antibodies. SLAM enables cells producing high affinity antibodies generated during in vivo immune responses to be isolated from any species. The isolated individual antibody producing cells are then clonally expanded followed by screening for those clones which produce anti-CD154 antibodies followed by the subsequent identification of the sequence of their variable heavy ($V_H$) and light ($V_L$) chain genes. A particular screening method is detailed in WO 04/051268. Thus, B cells that are positive for antibodies to human CD154 were isolated.

Several rat anti-human CD154 antibodies were identified and isolated using SLAM technology (FIG. 12). One of these antibodies, CA081 00342 (the "342 antibody"), was humanized, as described in the following example. Its DNA and deduced amino acid sequences are shown in FIG. 2. The gene encoding this antibody was cloned.

Example 2

Humanization of CA081 00342—Creation of 342.G2

SLAM antibody 342 was humanized by grafting the CDRs onto human germline frameworks. Alignments of the rat antibody (donor) sequence with the human germline (acceptor) frameworks are shown in FIG. 9, together with the designed humanized sequence. The light chain germline acceptor sequence chosen was the human VK1 2-1-(1) O12 V-region plus JK1 J-region (V BASE, MRC Centre for Protein Engineering, UK; SEQ ID NO: 35 and 36) (FIG. 3). The heavy chain germline acceptor sequence chosen was the human VH3 1-1 3-66 V-region plus JH4 J-region (V BASE, MRC Centre for Protein Engineering, UK; SEQ ID NO: 37 and 38)

(FIG. 3). In addition, a different VH acceptor framework was chosen, the human VH4 1-1 4-59 sequence (SEQ ID NOS: 39 and 40) (FIG. 3). The CDRs grafted from the donor to the acceptor sequence are as defined by Kabat (Kabat et al. Sequence of proteins of immunological interest (1987). Bethesda Md., National Institutes of Health, US), with the exception of CDR-H1 where the combined Chothia/Kabat definition is used (see WO91/09967). For grafts where only the CDRs were transferred from the donor antibody onto the acceptor frameworks, versions were constructed in which key donor framework residues were also included. These residues were identified using a method based on that described in WO 91/09967. For example, the light chain graft VK1gL4 contains donor residues at positions 38, 71 and 85; the heavy chain graft VH3 gH1 contains donor framework residues at positions 24, 48, 49, 73 and 78; the heavy chain graft VH4 gH1 contains donor frameworks at positions 48, 71 and 78. The sequences of all these grafts are shown in FIG. 9.

Genes encoding these V-region sequences were designed and constructed using standard molecular biology techniques by contract gene synthesis companies (Entelechon GmBH; DNA 2.0; Blue Heron). Modifications to create grafted variants were made using standard oligonucleotide-directed mutagenesis using PCR. The signal peptide sequences from the original rat antibodies were included in the original gene designs, to permit expression using mammalian cell expression vectors.

The grafted light chain genes were sub-cloned into a light chain expression vector, which contains DNA encoding the human C-Kappa constant region (Km3 allotype). The grafted heavy chain genes were sub-cloned into a human gamma-4 expression vector, which contains DNA encoding the human gamma-4 constant region containing the hinge stabilizing mutation S241P (Angal et al., *Mol Immunol.* 1993, 30(1): 105-8). Any suitable expression vector may be used. The original rat antibody genes were also sub-cloned into these vectors, creating plasmids expressing the chimeric rat V-region/human C-region antibody as a benchmark in assays.

Co-transfection of light chain gene and heavy chain gene plasmids into CHO cells enabled expression of IgG and analysis of human CD154 binding by Biacore®.

In order to analyze expression in *E. coli* and activity as a monovalent Fab', the genes for key constructs were sub-cloned into expression vector pTTOD (Fab) (WO 03/48208, WO 03/031475). Sub-cloning was achieved in a 2-stage process: first the VK gene fragment was cloned in as an EcoRV-BsiWI fragment; then the VH gene fragment was cloned in as a PvuII-XhoI fragment. This process fuses DNA encoding the signal peptide from the OmpA protein to the genes encoding both light and heavy chains, conferring secretion of translated protein to the bacterial periplasm. The resultant expression plasmids were transformed into *E. coli* K-12 strain W3110 and used in induction experiments in small-scale shake flasks and for high cell density fermentation.

TABLE 1

Affinity of 342 Fab constructs by Biacore ® (Purified Fab from 1 L fermentation)

| Graft | ka (1/Ms) | kd(1/s) | KD(M) | KD(pM) |
|---|---|---|---|---|
| gL4gH1 | 1.53E+07 | 6.97E−05 | 4.55E−12 | 4.55 |

Selection of the optimum graft was made taking into account both activity in assay and expression levels of Fab in *E. coli* fermentation. An example of affinity determination by Biacore® is shown in Table 1. On this basis graft gL4gH1 was chosen.

A plasmid was made encoding a Fab' version of the graft gL4gH1. The DNA sequence of the insertion insert of this graft is shown in FIG. 8 (SEQ ID NO: 41). FIG. 8 also provides the sequence of an insert (SEQ ID NO: 28) for expression of a Fab fragment, which can be used to make a F(ab)$_2$ fragment.

Example 3

Creation of Aglycosylated Hu5C8 and Hu342 Antibodies By Site-Directed Mutagenesis Aglycosylated hu5c8 and hu342 antibodies used in subsequent experiments were created using standard recombinant DNA techniques. Aglycosylated hu5c8 was made substantially as described in US2006/0193856, except for substitution of the huIgG4 Fc domain for the IgG1 Fc domain previously used, in order to further reduce effector function. The kappa light chain sequence of aglycosylated hu5c8 is shown in FIG. 13 (SEQ ID NO: 62, SEQ ID NO: 63 and SEQ ID NO: 64). The heavy chain of aglycosylated hu5c8 contains two mutations made by site directed mutagenesis in the CH2 (T299A, Kabat EU) and hinge (S228P Kabat EU) domains (FIG. 14; SEQ ID NO: 65, SEQ ID NO: 66 and SEQ ID NO: 67). The T299A mutation modifies the N-glycosylation site in the CH2 domain so that it is no longer a substrate for N-glycosylation enzymes, rendering the molecule aglycosylated.

The aglycosylated hu342 antibody was derived from the 342 Fab fragment vector. This sequence was modified by addition of human signal sequences and the appropriate human constant domain sequences. The aglycosylated hu342 antibody also comprises a huIgG4 Fc domain. The kappa light chain sequence of aglycosylated hu342 is shown in FIG. 15 (SEQ ID NO: 68, SEQ ID NO: 69 and SEQ ID NO: 70). The heavy chain of aglycosylated hu342 contains two mutations made by site directed mutagenesis in the CH2 (T299A, Kabat EU) and hinge (S228P Kabat EU) domains (FIG. 16; SEQ ID NO: 71, SEQ ID NO: 72 and SEQ ID NO: 73). The T299A mutation modifies the N-glycosylation site in the CH2 domain so that it is no longer a substrate for N-glycosylation enzymes, rendering the molecule aglycosylated. Both aglycosylated hu5c8 and hu342 were stably expressed in CHO cells.

Example 4

Binding to CD154: Binding Affinity Measurements

The Biacore® technology monitors the binding between biomolecules in real time and without the requirement for labeling. One of the interactants, termed the ligand, is either immobilized directly or captured on the immobilized surface while the other, termed the analyte, flows in solution over the captured surface. The sensor detects the change in mass on the sensor surface as the analyte binds to the ligand to form a complex on the surface. This corresponds to the association process. The dissociation process is monitored when the analyte is replaced by buffer. In the affinity Biacore® assay, the ligand is an anti-CD154 antibody such as 342 antibody and the analyte is the extracellular domain of human CD154. Details of the method are as follows:

Instrument: Biacore® 3000, Biacore AB, Uppsala, Sweden.
Sensor chip: CM5 (research grade) Catalogue Number: BR-1001-14, Biacore AB, Uppsala, Sweden. Chips were stored at 4° C.
BIAnormalising solution: 70% (w/w) Glycerol. Part of BIAmaintenance Kit Catalogue
Number: BR-1002-51, Biacore AB, Uppsala, Sweden. The BIAmaintenance kit was stored at 4° C.
Amine Coupling Kit: Catalogue Number: BR-1000-50, Biacore AB, Uppsala, Sweden. Ethyl-3-(3-dimethylaminopropyl) carbodiimide hydrochloride (EDC). Made up to 75 mg/mL in distilled water and stored in 200 µL aliquots at −70° C. N-Hydroxysuccinimide (NHS). Made up to 11.5 mg/mL in distilled water and stored in 200 µL aliquots at −70° C. 1 M Ethanolamine hydrochloride-NaOH pH 8.5. Stored in 200 µL aliquots at −70° C.
Buffers: Running buffer is HBS-EP (being 0.01 M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C. Immobilization buffer is Acetate 5.0 (being 10 mM sodium acetate pH 5.0). Catalogue number: BR-1003-51, Biacore AB, Uppsala, Sweden. Buffer stored at 4° C.
Ligand capture: Affinipure F(ab')$_2$ fragment goat anti-human IgG, Fab' fragment specific (Catalogue number: 109-006-097) or Fc fragment specific (Catalogue number: 109-006-098), Jackson ImmunoResearch Inc (Pennsylvania, USA). Reagents stored at 4° C.
Ligand: anti-CD154 antibodies.
Analyte: Recombinant extracellular domain of human CD154. Material was prepared at 2 mg/mL (40 µM) in phosphate-buffered saline, stored at 4° C., and diluted in HBE-EP running buffer for the assays. Typically CD154 was diluted from ~1 nM to ~100 pM by doubling dilutions for the affinity assay.
Regeneration Solution: 40 mM HCl prepared by dilution with distilled water from an 11.6 M stock solution (BDH, Poole, England. Catalogue number: 101254H). 5 mM NaOH prepared by dilution with distilled water from a 50 mM stock solution. Catalogue number: BR-1003-58, Biacore AB, Uppsala, Sweden.
Assay Method: BIA (Biamolecular Interaction Analysis) was performed using a Biacore® 3000 (Biacore AB). Affinipure F(ab')$_2$ fragment goat anti-human IgG, Fc- or Fab'-fragment specific (Jackson ImmunoResearch) were immobilized on a CM5 Sensor Chip via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 µl/min. Anti-CD154 antibodies or Fab fragments were used at concentrations such that, once captured by the immobilized anti-human IgG-Fc (or anti-human IgG Fab') surface, gave a signal of ≈200 RUs. Human CD154 was titrated over the captured antibody, at various concentrations. 90 µL of CD154 was injected over the surface (association phase), followed by a 240 second dissociation phase, all at a flow rate of 30 µL/min. The surface was regenerated by two 10 µL injections of 40 mM HCl, followed by a 5 µL injection of 5 mM NaOH at a flowrate of 10 µL/min. Background subtraction binding curves were analyzed using the BIAevaluation software (version 3.2) following standard procedures. Kinetic parameters were determined from the fitting algorithm.

This method may be used to assess the affinity for a CD154 protein, or a fragment thereof, of any of the antibody, antibody derivative or antibody fragment of this invention. Kd values obtained by Biacore® for anti-CD154 antibodies isolated by SLAM are shown in FIGS. 12 and 18.

Example 5

Inhibition of CD40 Binding

A flow cytometry-based assay was used to assess the binding of labeled CD40 to CD154-expressing D1.1 cells. D1.1 Jurkat cells (American Type Culture Collection) were maintained in RPMI 1640 medium (Gibco, 31870-025)) containing 10% (v/v) fetal calf serum (FCS), 2 mM glutamine (Invitrogen, 23030024), 1 mM sodium pyruvate (Invitrogen, 11360-039), 1% (v/v) D-(+)-glucose (Sigma, G8769) & 10 mM HEPES (Sigma, H0887). At time of assay, 100,000 D1.1 cells were incubated in 100 µL RPMI 1640 medium+10% FCS, in the presence or absence of serially diluted anti-CD154 antibody for 15 minutes at room temperature. 5 µL of a 1:75 dilution of hCD40-mFc-PE (Alexis Corp, ANC-504-050) was then added and incubated for a further 30 minutes at room temperature. After washing twice in phosphate-buffered saline (PBS) containing 1% (w/v) bovine serum albumin (BSA fraction V, Serologicals Proteins Inc, 81-068-5) and 0.02% (w/v) sodium azide (BDH, 103692K), cells were resuspended in 200 µL PBS/1% BSA/0.02% sodium azide and flow cytometry performed on a Becton Dickinson FACScan. The values for geometric mean fluorescence (FL2) were assessed in all cases. The inhibition of hCD40-mFc-PE binding was calculated relative to the signal in the absence of antibody (0% inhibition) and in the signal in the absence of hCD40-mFc-PE (100% inhibition), using the formula:

$$\left[\frac{0\% \text{ Inhibition} - \% \text{ Test}}{0\% \text{ Inhibition} - 100\% \text{ Inhibition}}\right] \times 100.$$

IC50 values from the data were obtained using XLfit as part of the Activity Base package.
The CD40 binding IC50 values for anti-CD154 antibodies isolated by SLAM are shown in FIGS. 12 and 18.

Example 6

Competition Binding Assay

A flow cytometry-based assay was used to assess the binding of anti-CD154 antibody to CD154-expressing D1.1 cells. D1.1 Jurkat cells (American Type Culture Collection) were maintained in RPMI 1640 medium (Gibco, 31870-025) containing 10% (v/v) fetal calf serum (FCS), 2 mM glutamine (BioWhittaker, 17-605E) and 1 Penicillin-Streptomycin (Mediatech, 30002107). At time of assay, 100,000 D1.1 cells were incubated in 10 mL PBS, 0.1% BSA, 0.02% sodium azide (FACS buffer), in the presence or absence of serially diluted anti-CD154 antibody and biotinylated anti-CD154 Fab (clone 342) for 2 hours at 4° C. The cells were washed three times in FACS buffer with centrifugation at 290×g for 3 minutes in between washes. A 1:500 dilution of streptavadin-R-phycoerythrin conjugate (Jackson Immunoresearch, 016-110-084) in 150 µM FACS buffer was added and the cells were incubated for one hour at 4° C. The cells were washed once and fixed in PBS with 3% formaldehyde at room temperature for 10 minutes. The cells were resuspended in FACS buffer and run on a FacsCalibur (BD). The values for geometric mean fluorescence (FL2) were assessed in all cases. Biotin 342 Fab binding was plotted against the concentration of competing antibody to obtain sigmoidal inhibition curves that were fit to a four parameter curve fit using GraphPad Prism. The $IC_{50}$ values generated in this assay are shown in FIG. 18.

Example 7

ICAM-1 Upregulation Assay

The ability of the anti-CD154 antibodies to inhibit CD40L:CD40 cell surface interactions was measured in an in vitro co-culture potency assay. Ligation (e.g., binding) of CD40 with CD154 (CD40L) activates B lymphocytes resulting in an upregulation of CD54 (ICAM-1) on the cell surface and this contact dependent CD40L:CD40 B cell activation can be blocked by anti-CD154. Briefly, D1.1 Jurkat T lymphoma cells (CRL-10915, American Type Culture Collection (ATCC), Manassas, Va., USA) expressing CD154 and Ramos 2G6.4C10 B lymphoma cells (CRL-1923, ATCC) expressing CD40 were co-cultured in a 37° C. incubator with 5% $CO_2$ overnight at a 1:4 ratio with titrations of anti-CD154 Fabs or a control intact Ab (hu5C8). The assay was performed in 96-well round bottom plates at a concentration of $1\times10^6$ cells/ml in RPMI complete media (RPMI with 10% FBS, 1% L-glutamine, 1% sodium pyruvate and 10 mM HEPES pH 6.8, Gibco BRL, Rockville, Md., USA). The following day the cells were stained for one hour at 4° C. with CD20 FITC (#555622) and CD54 APC (#559771) from BD Pharmingen (San Diego, Calif., USA) at a concentration of 1:100 and 1:200 respectively in PBS containing 1% BSA and 0.1% sodium azide. The cells were washed and fixed with 1% paraformaldehyde and analyzed on a FACScan Calibur Cytometer (BD Biosciences). The geometric mean fluorescence of the Ramos cells (double positive cells) versus the concentration of anti-CD154 (CD40L) was fit to a 4-parameter curve using DeltaGraph software (Red Rock Software, Salt Lake City, Utah, USA) (FIGS. 12 and 18). The IC50 values were used to determine the relative potency of the anti-CD154 antibodies.

Example 8

Activity in Cynomolgus Monkey Model of Immune Response

The model used to demonstrate activity in vivo is described in Gobburu et al. (1998) *J Pharmacol Exp Therapeutics* 286:925. Cynomolgus monkeys received single i.v. doses of either saline, Hu5c8 antibody or a dose response of 342 Fab'-PEG, 4 hours prior to challenge with a single i.m. dose of 0.5 mL tetanus toxoid (TT). Each treatment group contained 3 males and 3 females. On day 30, a second dose of inhibitor was given, and the animals were re-challenged with TT (the secondary response). Blood samples were taken at selected time periods for up to 50 days for analysis of both IgG and IgM anti-TT titers (FIGS. 19 and 21). The data show that 342 Fab'-PEG inhibits the IgG and IgM immune response to TT in a dose-dependent manner.

The IgG anti-TT titers in cynomolgus monkeys were also measured after treatment with a single dose (20 mg/kg for hu5c8, aglycosyl 5c8 and aglycosyl 342 and 40 mg/kg for 342 Fab'-PEG and 342 DFM-PEG) of various forms of anti-CD154 antibodies (FIG. 20). Inhibition of the TT immune response was observed with all antibodies evaluated.

Example 9

Fluorescence Activated Cell Sorting Cross-Blocking Assay

Figure 23:
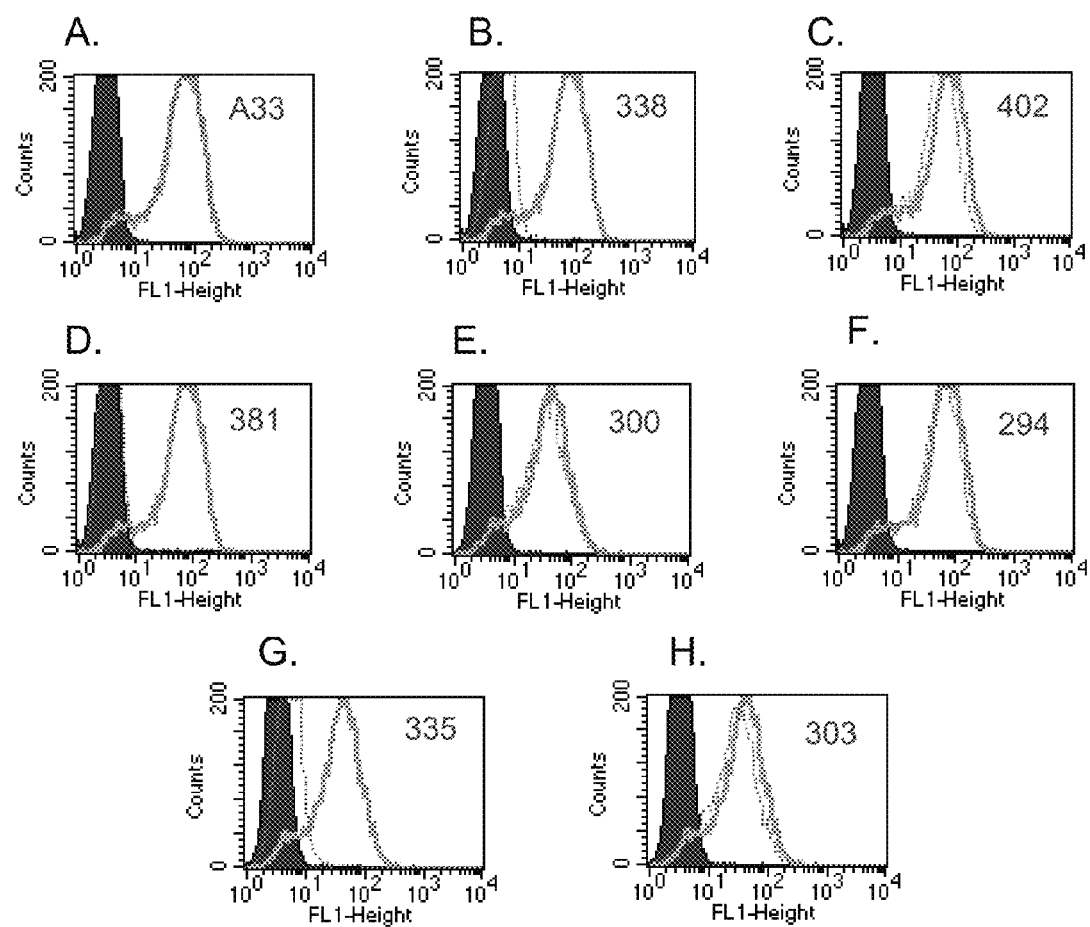
FIGS. 23A-23H show the results of flow cytometry analysis of cross-blocking of labeled 342 Fab' binding to CD154-expressing D1.1 Jurkat cells pre-bound with an unlabeled first anti-CD154 Fab', as indicated in each panel (23A—A33; 23B—338; 23C—402; 23D—381; 23E—300; 23F—294; 23G—335; 23H—303) (see Example 9). A33 is an isotype-matched control antibody and confirms that there is no non-specific cross-blocking.
Figure 24:
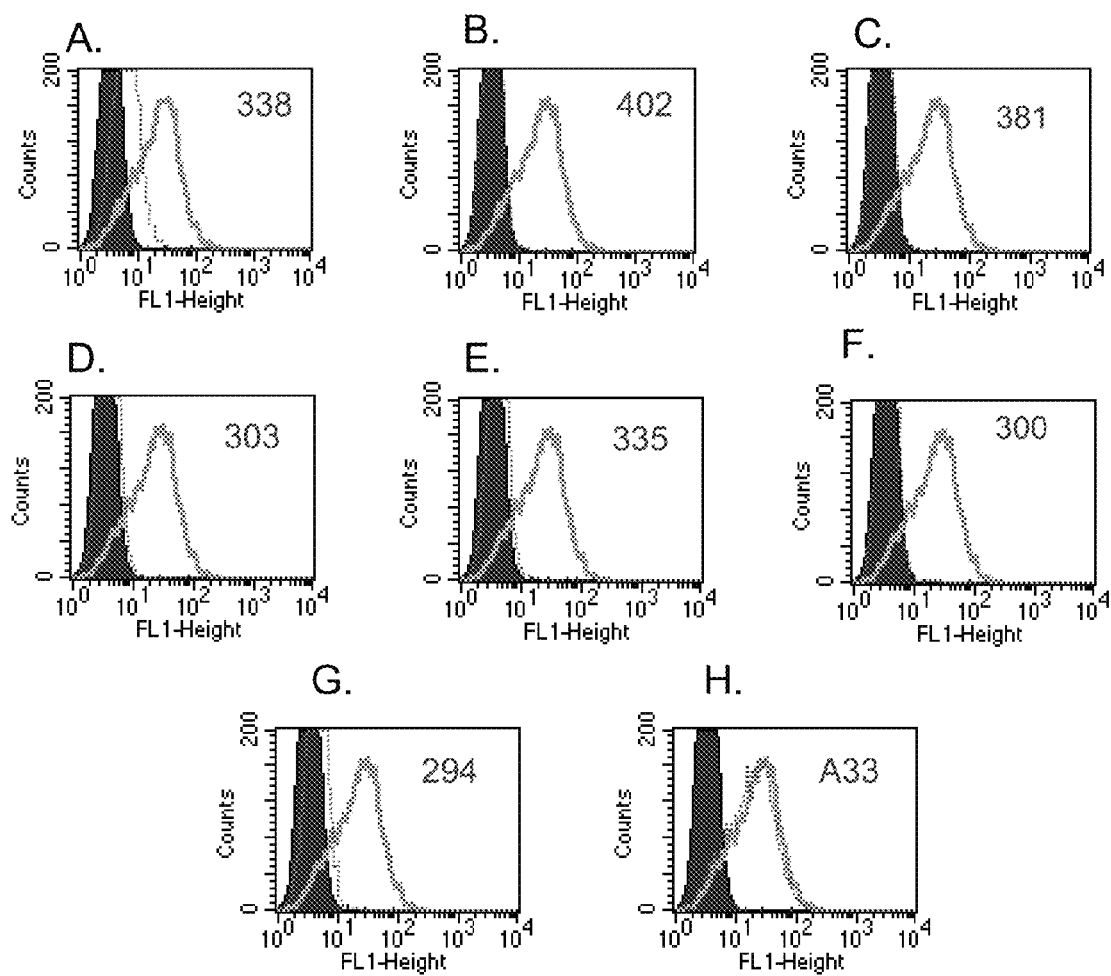
FIGS. 24A-24H shows the results of flow cytometry analysis of cross-blocking of labeled Hu5c8 Fab' binding to CD154-expressing D1.1 Jurkat cells pre-bound with an unlabeled first anti-CD154 Fab', as indicated in each panel (24A—338; 24B—402; 24C—381; 24D—303; 24E—335; 24F—300; 24G—294; 24H—A33) (see Example 9). A33 is an isotype-matched control antibody and confirms that there is no non-specific cross-blocking.

The binding properties of the anti-CD154 Fab' fragments of the invention were studied by cross-blocking antibody assays. Briefly, CD154-expressing D1.1 Jurkat cells were incubated with either medium or 10 μg/ml unlabeled first anti-CD154 Fab' for 60 minutes at room temperature. After no washing, an optimal dilution of an Alexa Fluor 488-labeled second anti-CD154 Fab' (300 ng/ml) was added for 60 minutes. Cells were then washed and analyzed by flow cytometry. If the first and second Fab' bind to the same epitope, the first Fab' will competitively block the binding of the second Fab'. If the two antibodies bind to different epitopes, the first Fab' will not block the binding of the second Fab'. If the labeled second Fab' tested is 342, it can be demonstrated that the 342 Fab' is cross-blocked by 338 (FIG. 23B), 381 (FIG. 23D) and 335 (FIG. 23G) Fab's but is not cross-blocked by 295 (not shown), 402 (FIG. 23C), 300 (FIG. 23E), 303 (FIG. 23H) or 294 (FIG. 23F) Fab's. When the labeled Fab' is hu5c8, cross-blocking by 338 (FIG. 24A), 402 (FIG. 24B), 381 (FIG. 24C), 303 (FIG. 24D), 335 (FIG. 24E), 300 (FIG. 24F) and 294 (FIG. 24G) Fab's can be demonstrated. Testing with A33 (an isotype-matched control antibody) confirms there is no non-specific cross-blocking (FIGS. 23A and 24H). Antibodies 342 and hu5c8 competed with each other for CD154 binding regardless of which was the unlabeled (first) and labeled (second) Fab'.

Example 10

Biacore® Analysis of Antibody Binding

Figure 25:
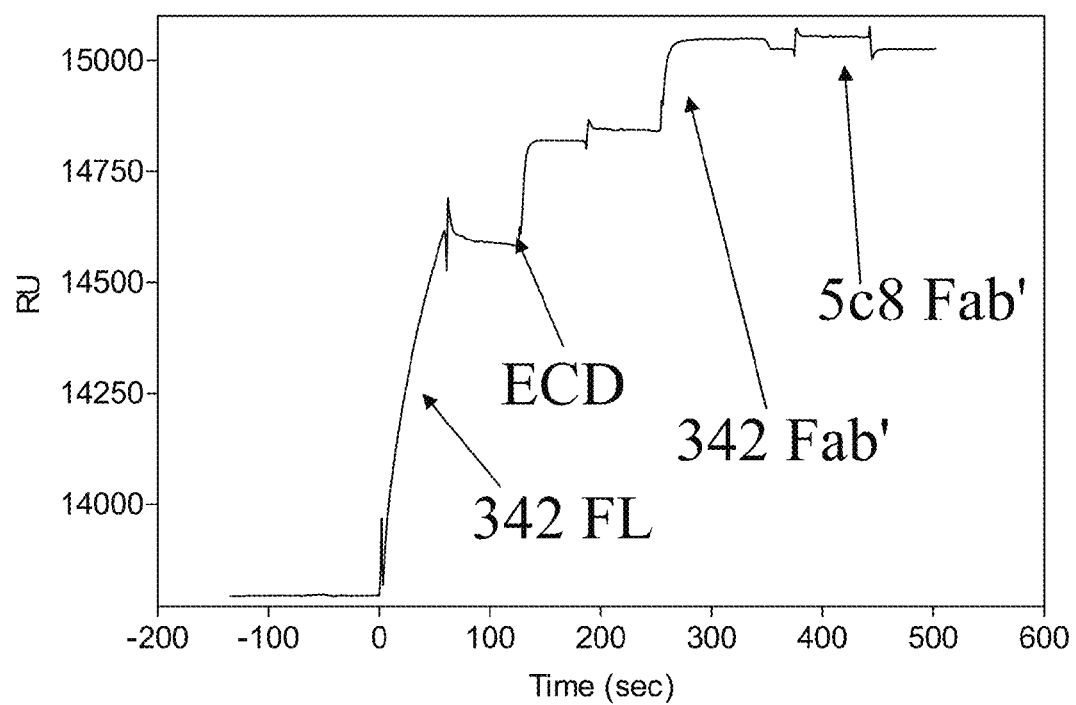
FIGS. 25A-F show the results of Biacore® analysis of competitive binding of various forms of the 342 and Hu5c8 antibodies to soluble CD154 protein (ECD) or a CD40:CD154 complex. FL—full length. CD40hFc—human CD40 fusion protein.

Biacore® analysis of 342 and hu5c8 antibody binding to soluble CD154 protein (sCD154) (extracellular domain; ECD) indicated that 342 displaced hu5c8 binding to sCD154 when added to the sCD154 second (FIGS. 25 A and B). 5c8 was not able to displace 342 from sCD154 when added to the sCD154 second (FIG. 25 C). Antibody 338 behaved similarly to 342 with respect to non-reciprocal results in hu5c8 competition assay.

Hu5c8 Fab can bind to a 342 full length (FL)/sCD154 complex (FIG. 25D). This result suggests that hu5c8 Fab does not compete with the 342 FL binding site when 342 FL is added first. Without being bound by theory, these results suggest that binding of one or two arms of the sCD154 trimer by 342 does not prevent hu5c8 binding to the "free" arm(s).

There is a slight (~20RU) increase in binding when hu5c8 Fab is followed by 342 Fab' (FIG. 25E). This result raises the possibility that either hu5c8 Fab' has blocked binding of 342 Fab' or that 342 Fab' has replaced hu5c8 Fab' on the captured sCD154.

Neither 342 Fab' nor hu5c8 Fab' bind to a CD40:sCD154 complex or affect the dissociation of the complex in a protein assay. The fact that neither Fab' can bind the CD40:sCD154 complex suggests either that the complex uses all three sCD154 arms or that the complex sterically hinders access of either Fab' to a "free" arm.

Example 11

Human Platelet Activation

Assay 1

Figure 26:
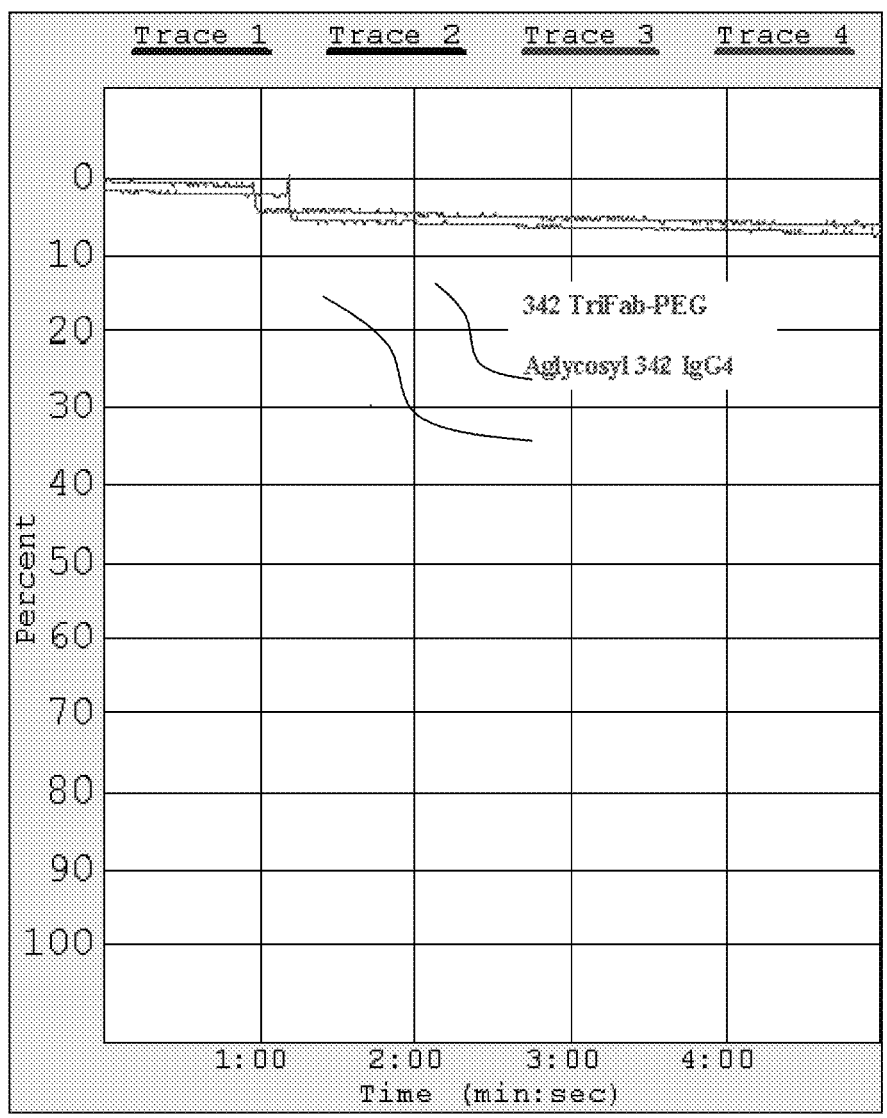
FIG. 26 is a graph showing the results of a platelet aggregation assay described in Example 11 (Assay 1) performed with the Hu5c8 anti-CD154 antibody, 342 Fab'-PEG anti-CD154 antibody, and control antibodies. The first panel shows results obtained with CD40L complexes formed with whole IgG and the second panel shows complexes formed with Fab'-PEG or diFab'-PEG. The third panel shows results obtained with triFab'-PEG and aglycosylated anti-CD154 antibody hu342.

Platelet aggregation can be measured using published assays (e.g., Florian et al. (2005) *Thrombosis Hemostasis* 93: 1137). In one assay, platelets were washed from normal donor platelet-rich plasma in HEPES-buffered saline in BSA coated tubes and adjusted to 250,000 per microliter (μl). Washed platelets were then pipetted into an aggregometer cuvette (Chrono-Log 490D) and the trace signal was calibrated to zero percent aggregation, using HEPES (assay) buffer for blanking. In this instrument the cuvette is maintained at 37.0° C. and a siliconized magnetic bar stirs the platelets at 1000 rpm. Fully formed immune complexes (i.e., antibody plus recombinant human soluble CD40L (rhsCD40L), in 1:1 stoichiometry where rhsCD40L was treated as trimeric) were added to platelets and aggregation was assessed as a trace derived from the solution's optical density. Specifically, 15 μl of immune complex was added to 285 μl of washed platelet suspension such that after adding to the cuvette, the final concentration of sCD40L was 10 μg/ml and that of IgG antibody was 27.8 μg/ml or 16.7 μg/ml for Fab'-PEG. The data show that aggregation occurs in the presence of the intact IgG anti-CD40L antibody Hu5c8, but not with 342 Fab'-PEG (FIG. 26).

Assay 2

In another assay described in WO 07/59332, platelet aggregation is measured by contacting platelets with a platelet activating agent (e.g., adenosine diphosphate (ADP), collagen, thrombin, thromboxane, neurophil elastase, p-selectin, or convulxin), contacting the activated platelets with an anti-CD154 antibody, and then contacting the activated platelets with a cross-linking agent (e.g., soluble CD154 (sCD154), anti-human IgG antibody, anti-hFc antibody, RF, Fc receptor-positive accessory cell, soluble protein A, or soluble human Fc receptor). Aggregation is then quantified by sedimentation of platelets, where sedimentation of platelets is indicative of aggregation of the platelets. The aggregation assay was performed on platelet rich plasma (PRP). Approximately 50 mL of whole blood was collected in aliquots in 4.5 mL vacutainer tubes containing 0.5 mL of 3.8% sodium citrate. PRP was prepared by centrifuging the anticoagulated blood at 200 g for 10 minutes and harvesting the supernatant. To perform the assay, the Biodata 4-channel platelet aggregation profiler (PAP-4; Biodata Corp., Hatboro, Pa.) was blanked using a cuvette containing only platelet poor plasma (PPP). A 350 μL aliquot of PRP, containing approximately 2 to 5×10$^8$/mL platelets, was added to a cuvette containing a stir bar. Anti-CD40L antibody, human IgG, normal human serum, CD40-Fc, or anti-hFc were added in a total volume of 100 μL. The loaded cuvette was placed in the machine and the reaction components mixed prior to the addition of ADP.

Aggregation was initiated with the addition of sub-optimal concentration of ADP in 50 μL (final concentration varies for each individual sample). The aggregation profiler has four ports, which can run simultaneously. An aggregation tracing was generated for each sample for four minutes following the addition of ADP. At the end of the tracing, the instrument calculates the percentage of aggregation by comparing the transmission of light through the sample to the transmission of light through the PPP blank. A titration was performed at the beginning of each experiment, and subsequent runs were performed at a suboptimal ADP concentration.

The results from this assay are shown in FIG. 27. PRP was obtained from one healthy individual. Aggregation was induced with 0.75 μM ADP, which was determined to be suboptimal for this donor. A positive control anti-CD154 antibody and a negative control hIgG were evaluated at 200 μg/mL and sCD154 at 30 μg/mL. Anti-CD154 antibody or hIgG was mixed with recombinant sCD154 for no less than 20 minutes prior to addition to the PRP-containing cuvette. Bars represent the means and standard deviations of two data points. The results show that while negative control human IgG (hIgG) and sCD154 together had no effect on platelet aggregation, the positive control anti-CD154 antibody enhanced platelet aggregation. The results from this assay using a positive and negative control demonstrate that this assay may be used to compare the relative effect of the antibodies of the present invention on platelet aggregation.

To determine if the platelets express CD154 on their surface, the platelets may be incubated with a biotin-conjugated anti-CD154 antibody and the presence of surface CD154 determined by quantifying the bound biotinylated anti-CD40L antibody. Accordingly, surface expression of CD154 was evaluated after 1, 10, 20, 40, and 60 minutes of incubation with or without 10 μM ADP. Surface expression of CD40L was detectable on ADP-activated platelets as early as one minute after activation and increased over time. The binding of biotin-conjugated anti-CD154 antibody is specific for CD154, as preincubation of biotin-conjugated anti-CD154 antibody with sCD154 inhibited binding to activated platelets. The amount of surface CD154 detected on inactivated ("resting") platelets also increased over time. This phenomenon is likely attributable to the basal level of platelet activation under the experimental conditions.

Example 12

Methods for Determining Altered Effector Function of Aglycosylated and Other Variant Antibodies The following example describes assays useful for determining and characterizing effector function(s) of the aglycosylated and other modified variant antibodies of the invention.

The effector function of the aglycosylated and other modified variant antibodies of the invention may be characterized by the antibodies' ability to bind an antigen and also bind an Fc receptor or a complement molecule such as C1q. In particular, the FcγR binding affinities may be measured with assays based on the ability of the antibody to form a "bridge" between the CD154 antigen and a cell bearing an Fc receptor. The C1q binding affinity may be measured based on the ability of the antibody to form a "bridge" between the CD154 antigen and C1q. The interaction of the antibodies of the present invention with an FcR or with complement can also be measured by the bead-based AlphaScreen® technology (Perkin Elmer®).

Fc Receptor Binding Assays

The FcγR bridging assay may be performed by coating 96-well Maxisorb ELISA plates (Nalge-Nunc Rochester, N.Y., USA) with recombinant soluble human CD154 ligand (e.g., at a concentration of 1 μg/ml overnight at 4° C. in PBS; Karpusas et al. 1995 *Structure* 3(10): 1031-1039 and 3(12): 1426 and Karpusas et al. 2001 *Structure* 9(4): 321-329). Titrations of glycosylated or aglycosylated forms of anti-CD154 antibody are bound to CD154 for 30 minutes at 37° C., the plates are then washed, and the binding of fluorescently labeled U937 (CD64+) cells are measured. The U937 cells may be grown in RPMI medium with 10% FBS, 10 mM HEPES, L-glutamine, and penicillin/streptomycin, split 1:2, and activated for one day prior to the assay with 1000 units/ml of IFNγ to increase Fc receptor (FcγRI) expression.

In another variation of the assay, the ability of the antibodies of the invention to bind to, or rather, fail to bind to, yet another Fc receptor, such as, FcγRIII (CD16) may be performed using the above bridging assay against fluorescently labeled human T cells (Jurkat cells) transfected with a CD16 expression construct. The ligand may be produced by a monolayer of CD154-expressing Chinese Hamster Ovary (CHO) cells grown in 96-well tissue culture plates (Corning Life Sciences Acton, Mass., USA). For example, the CHO-CD 154+ cells are seeded into 96 well plates at I×105 cells/ml and grown to confluency in oc-MEM with 10% dialyzed FBS, 100 nM methotrexate, L-glutamine, and penicillin/streptomycin (Gibco-BRL Rockville, Md., USA). The CD 16+ Jurkat cells are grown in RPMI with 10% FBS, 400 pg/ml Geneticin, 10 mM HEPES, sodium pyruvate, L-glutamine, and penicillin/streptomycin (Gibco-BRL) and split 1:2 one day prior to performing the assay.

In the assays for both receptors, the Fc receptor-bearing cells may be labeled with 2',7'-bis-(2-carboxyethyl)-5-(and-6)-carboxyfluorescein acetoxymethyl ester (BCECF-AM) (Molecular Probes Eugene, Oreg., USA) for 20 minutes at 37° C. After washing to remove excess label, 1×10$^5$ of the labeled cells are incubated in the assay for 30 minutes at 37° C. Unbound FcγR positive cells are removed by washing several times and plates are read on a microplate reader (Cytofluor 2350 Fluorescent Microplate Reader, Millipore Corporation Bedford, Mass., USA) at an excitation wavelength of 485 nm and an emission wavelength of 530 nm.

In addition to the assays described above, binding of the antibodies of the present invention to Fc receptors can be measured in a competition format using an AlphaScreen™ (Amplified Luminescent Proximity Homogeneous Assay; Perkin Elmer) or directly using Surface Plasmon Resonance (Biacore®). Biacore assays can monitor binding of analyte receptor to antibody captured on a protein A/G chip using a Biacore® 3000 instrument. Biacore® is a well-established method for characterizing protein-protein interactions (Myszka 1997 *Curr Opin Biotechnol.* 8:50-57; Malmborg & Borrebaeck 1995 *J Immunol Methods* 183:7-13), and has been used successfully to measure the binding of IgG antibodies to FcγRIII (Galon et al., 1997 *Eur J Immunol.* 27:1928-1932). For example, protein A/G is coupled covalently to a sensor chip (e.g., a CM5 sensor chip using NHS chemistry). A running buffer (e.g., HBS-EP (0.01 M HEPES pH 7.4, 0.15 M NaCl, 3 mM EDTA, 0.005% v/v Surfactant P20, Biacore®)), and a chip regeneration buffer (e.g., Glycine 1.5 (10 mM glycine-HCl, pH 1.5, Biacore®)) are used in the assay. Variant anti-CD154 antibodies with reduced effector function and wildtype or native anti-CD154 antibodies are diluted to 100 nM in running buffer (e.g., HBS-EP buffer) and are bound to the protein A/G chip for 5 min. Receptors are bound in the association phase in concentration series, followed by a dissociation phase with buffer. A cycle with no antibody provides a baseline response. Sensorgrams may be globally fit to a 1:1 Langmuir binding model to obtain equilibrium dissociation constants ($K_D$s) using BIAevaluation software v4.1 (Biacore®), for example.

AlphaScreen assays use untagged antibody to compete the interaction between biotinylated IgG bound to streptavidin donor beads and FcγR-His-GST bound to anti-GST acceptor beads. A wildtype or native anti-CD154 antibody (such as an IgG1 antibody) is biotinylated using standard methods and dialyzed in PBS. Anti-GST acceptor beads and streptavidin donor beads are available from commercial vendors and can be used at 20 µg/ml final concentration. FcγRI-His-GST, FcγRIIIa-His-GST, FcγRIIa-His-GST, or any other tagged FcR, in 1× assay buffer (e.g., 25 mM HEPES, 100 mM NaCl, 0.1% BSA, 0.01% Tween-20, pH 7.4) is distributed into each well of a 96-well plate to 0.5 nM final concentration. Wildtype or native anti-CD154 antibody, variant anti-CD154 antibody, or buffer is prepared as ½ log dilutions in 1× assay buffer, and aliquoted directly into each well. After brief centrifugation, biotinylated wildtype anti-CD154 antibody (e.g., an IgG1 antibody) in 1× assay buffer is added to each well to 5 nM final concentration. 100 µg/ml anti-GST acceptor beads are added to each well, and the plate is incubated in the dark for 1 hour at room temperature. 100 µg/ml streptavidin donor beads are added to each plate, and after brief centrifugation the plate is incubated at room temperature for 1.5 hours. Reaction samples are transferred to white opaque plates, and fluorescence is read in a Fusion™ Alpha-FP HT microplate reader (Perkin Elmer). Data may be normalized to the highest signal (no competition) and fit to a one-site competition model using nonlinear regression with the software GraphPad Prism (GraphPad Software), for example.

The skilled artisan may perform the above or similar assays to measure binding of antibody variants to any FcR, including, for example, FcγRIIa.

C1q Binding Assays

The C1q binding assay may be performed by coating 96-well Maxisorb ELISA plates (Nalge-Nunc Rochester, N.Y., USA) with 50 µl recombinant soluble human CD154 ligand (Karpusas et al. *Structure,* 15; 3 (12): 1426 (1995) at 10 µg/ml overnight at 4° C. in PBS. The wells are aspirated and washed three times with wash buffer (PBS, 0.05% Tween 20) and blocked for at least 1 hour with 200 µl/well of block/diluent buffer (0.1 M Na$_2$HPO$_4$, pH 7.0, 1 M NaCl, 0.05% Tween 20, 0.1% gelatin). The antibody to be tested is diluted in block/diluent buffer starting at 15 µg/ml with 3-fold dilutions. 50 µl is added per well, and the plates are incubated for 2 hours at room temperature.

After aspirating and washing as above, 50 µl/well of 2 µg/ml of Sigma human C1q (C0660) diluted in block/diluent buffer is added and incubated for 1.5 hours at room temperature. After aspirating and washing as above, 50 µl/well of sheep anti C1q (Serotec AHP033), diluted 3,560-fold in block/diluent buffer, is added. After incubation for 1 hour at room temperature, the wells are aspirated and washed as above. 50 µl/well of donkey anti-sheep IgG HRP conjugate (Jackson *ImmunoResearch,* 713-035-147) diluted to 1:10,000 in block/diluent is then added, and the wells are incubated for 1 hour at room temperature.

After aspirating and washing as above, 100 µl TMB substrate (420 µM TMB, 0.004% H$_2$O$_2$ in 0.1 M sodium acetate/citric acid buffer, pH 4.9) is added and incubated for 2 min before the reaction is stopped with 100 µl 2 N sulfuric acid. The absorbance is read at 450 nm with a Softmax PRO instrument, and Softmax software is used to determine the relative binding affinity (C value) with a 4-parameter fit.

An alternative C1q binding assay uses ELISA to determine anti-CD154 binding to C1q but does not use CD154 as a bridge. Briefly, assay plates may be coated overnight at 4° C. with a variant antibody or a parent antibody (control) in coating buffer. The plates may then be washed and blocked. Following washing, an aliquot of human C1q may be added to each well and incubated for 2 hours at room temperature. Following a further wash, 100 µl of a sheep anti-complement C1q peroxidase conjugated antibody may be added to each well and incubated for 1 hour at room temperature. The plate may again be washed with wash buffer and 100 µl of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 µl of 4.5 $NH_2SO_4$. The absorbance may then read at (492-405) nm.

An exemplary antibody variant is one that displays a "significant reduction in C1q binding" in this assay. A significant reduction may be, in some embodiments, about 100 µg/ml of the antibody variant displays about 50-fold or more reduction in C1q binding compared to 100 μg/ml of a control antibody having a nonmutated IgG1 Fc region. In the most preferred embodiment, the polypeptide (i.e., antibody) variant does not bind C1q, i.e., 100 μg/ml of the antibody variant displays about 100-fold or more reduction in C1q binding compared to 100 μg/ml of the control antibody.

Complement Activation and CDC

To assess complement activation, a complement dependent cytotoxicity (CDC) assay may be performed, e.g. as described in Gazzano-Santoro et al., *J. Immunol. Methods* 202:163 (1996). Briefly, various concentrations of the polypeptide (i.e., antibody) variant and human complement may be diluted with buffer. Cells which express the antigen to which the polypeptide variant binds may be diluted to a density of about $1\times10^6$ cells/ml. Mixtures of polypeptide variant, diluted human complement and cells expressing the antigen may be added to a flat bottom tissue culture 96 well plate and allowed to incubate for 2 hours at 37° C. and 5% $CO_2$ to facilitate complement mediated cell lysis. 50 μl of alamar blue (Accumed International) may then be added to each well and incubated overnight at 37° C. The absorbance is measured using a 96-well fluorometer with excitation at 530 nm and emission at 590 nm. The results may be expressed in relative fluorescence units (RFU). The sample concentrations may be computed from a standard curve and the percent activity as compared to nonvariant polypeptide is reported for the polypeptide variant of interest.

Example 13

Mapping of 342 Antibody Binding Site on CD154 Protein

Experiments were carried out to identify the amino acid residues in human CD154 that are important in the binding of 342 using human-mouse chimeric CD154 proteins. 342 binds with high affinity to human CD154 but does not bind to mouse CD154. Therefore, by mutating CD154 mouse residues to those of the corresponding human residues and measuring the change in the affinity of the mutated protein for 342, important binding residues can be identified. Six groups of mutants were selected where human residues at selected regions were introduced into soluble mouse CD154 (marked 1-6 in FIG. 28). Non-mutated human and mouse soluble CD154 (sCD154) proteins were also evaluated. The different sCD154 proteins were used in Biacore® experiments using 342 (in an IgG format) immobilized on the chip and with the sCD154 supernatants in the solution phase. The results demonstrated that 342 binding only occurs with the introduction of human Group 5 residues into mouse CD154.

Example 14

Competition ELISA Cross-Blocking Assay

To demonstrate cross blocking of 342 and 5c8 Fab's, we used a competition ELISA. In this assay, anti-Myc antibody 9E10 was coated onto an ELISA plate. Myc-tagged CD154 was captured by this antibody. A dilution series of unlabeled 342 or 5c8 Fab' was incubated with either 1 nM biotin 342 Fab' or 0.3 nM biotin 5c8 on the plate for two hours at room temperature in PBS, 0.05% Tween-20, 1% BSA. The plate was washed and the amount of biotinylated 5c8 Fab bound was determined using streptavidin HRP as a secondary. The signal was graphed and fit using either a one site binding hyperbola or a two site binding hyperbola curve fit in Prism software (Graph Pad).

A titration of biotin 342 Fab' on CD154 to determine the appropriate concentration for cross-blocking analysis was performed (FIG. 29A). A 1 nM concentration was found to be on the linear part of the curve. A titration of biotin 5c8 Fab' on CD154 to determine the appropriate concentration for cross-blocking analysis was also performed (FIG. 29B). A 0.3 nM concentration was found to be on the linear part of the curve. In an experiment to analyze cross-blocking of biotin 342 and biotin 5c8 Fab's by unlabeled 342 Fab', 342 Fab' inhibited biotin 342 Fab' binding with an affinity of 0.09 nM (FIG. 29C). 342 Fab' inhibits biotin 5c8 binding with two affinities, 0.134 nM and 76 nM (FIG. 29C). Cross-blocking of biotin 342 by unlabeled 5c8 Fab' is shown in FIG. 29D. The maximum concentration of 5c8 Fab' on this curve, 50 nM, is well above the saturation point for 5c8 and is also well above the 1 nM concentration of biotin 342. The lack of complete inhibition at these concentrations suggests that 5c8 is unable to completely block all of the 342 binding sites on CD40L.

We claim:

1. An isolated nucleic acid molecule encoding a chimeric or humanized CD154 binding antibody comprising heavy chain CDR1, CDR2 and CDR3 sequences selected from:
   (a) SEQ ID NO: 3, SEQ ID NO: 4 and SEQ ID NO: 5, respectively;
and comprising light chain CDR1, CDR2 and CDR3 sequences selected from:
   (a) SEQ ID NO: 6, SEQ ID NO: 7 and SEQ ID NO: 8, respectively.

2. The isolated nucleic acid molecule according to claim 1, wherein said nucleic acid molecule is a DNA molecule comprising a sequence selected from SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 41, SEQ ID NO: 70 or SEQ ID NO: 73 or comprising a sequence selected from a sequence at least 90% identical to SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 41, SEQ ID NO: 70 or SEQ ID NO: 73.

3. The isolated nucleic acid according to claim 1, wherein said nucleic acid encodes an chimeric or humanized CD154 binding antibody that is engineered to have reduced effector functions.

4. An isolated vector comprising a nucleic acid molecule of claim 1.

5. An isolated host cell comprising a vector of claim 4.

6. The isolated host cell according to claim 5, wherein the host cell is a prokaryotic cell.

7. The isolated host cell according to claim 5, wherein the host cell is a eukaryotic cell.

8. A method for producing a chimeric or humanized CD154 binding antibody comprising the steps of:
   (a) culturing a host cell of claim 5 under conditions suitable for expression of the chimeric or humanized antibody by the host cell; and
   (b) recovering the chimeric or humanized antibody.

9. The method according to claim 8, wherein the host cell is a prokaryotic or a eukaryotic cell.

10. An isolated vector comprising a DNA molecule of claim 2.

11. An isolated host cell comprising a vector of claim 10.

12. The isolated host cell according to claim 11, wherein the host cell is a prokaryotic cell.

13. The isolated host cell according to claim 11, wherein the host cell is a eukaryotic cell.

14. A method for producing a chimeric or humanized CD 154 binding antibody comprising the steps of:
   (a) culturing a host cell of claim 11 under conditions suitable for expression of the chimeric or humanized antibody by the host cell; and
   (b) recovering the chimeric or humanized antibody.

15. The method according to claim 14, wherein the host cell is a prokaryotic or a eukaryotic cell.

\* \* \* \* \*

SEQUENCE LISTING

```
<160> NUMBER OF SEQ ID NOS: 77

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45
```

```
Gly Val Ile Trp Gly Asp Gly Asp Thr Ser Tyr Asn Ser Val Leu Lys
 50                  55                  60

Ser Arg Phe Thr Ile Ser Arg Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Gln Leu Thr His Tyr Tyr Val Leu Ala Ala Trp Gly Gln Gly Thr
            100                 105                 110

Leu Val Thr Val Ser
            115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asp Leu Tyr Tyr Asn
                 20                  25                  30

Leu Ala Trp Tyr Gln Arg Lys Pro Gly Lys Ala Pro Lys Leu Leu Ile
             35                  40                  45

Tyr Asp Thr Tyr Arg Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Ser Tyr Tyr Cys Gln Gln Tyr Tyr Lys Phe Pro Phe
                 85                  90                  95

Thr Phe Gly Gln Gly Thr Lys Val Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Ser Ser Thr Asn Tyr His Val His
 1               5                  10

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Ile Trp Gly Asp Gly Asp Thr Ser Tyr Asn Ser Val Leu Lys Ser
 1               5                  10                  15

<210> SEQ ID NO 5
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Leu Thr His Tyr Tyr Val Leu Ala Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Glu Asp Leu Tyr Tyr Asn Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Thr Tyr Arg Leu Ala Asp
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Tyr Lys Phe Pro Phe Thr
1               5

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Thr Asn Tyr
            20                  25                  30

His Val His Trp Ile Arg Gln Pro Pro Gly Lys Gly Leu Glu Trp Ile
        35                  40                  45

Gly Val Ile Trp Gly Asp Gly Asp Thr Ser Tyr Asn Ser Val Leu Lys
    50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ser Thr Asn Tyr
            20                  25                  30

His Val His Trp Val Arg Gln Ala Pro Gly Lys Gly Leu Glu Trp Val
        35                  40                  45

Ser Val Ile Trp Gly Asp Gly Asp Thr Ser Tyr Asn Ser Val Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ser Thr Asn Tyr
            20                  25                  30

His Val His Trp Ile Arg Gln Pro Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115
```

```
<210> SEQ ID NO 12
<211> LENGTH: 221
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 13
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65                  70                  75                  80
```

```
Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30

Leu Ala Trp Tyr Gln Gln Lys Pro Gly Lys Ala Pro Lys Leu Leu Ile
        35                  40                  45

Tyr Asp Thr Tyr Arg Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Lys Phe Pro Phe
                85                  90                  95

Thr Phe Gly Gln Gly Thr Lys Val Glu Ile Lys
            100                 105

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30
```

Leu Ala Trp Tyr Gln Arg Lys Pro Gly Lys Ala Pro Lys Leu Leu Ile
            35                  40                  45

Tyr Asp Thr Tyr Arg Leu Ala Asp Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Ser Tyr Tyr Cys Gln Gln Tyr Tyr Lys Phe Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gatatccaga tgacccagag tccaagcagt ctctccgcca gcgtaggcga tcgtgtgact        60
attacctgtc gtgccagtga ggacctctat tacaacctgg cctggtatca gcaaaaaccg       120
ggcaaagccc cgaagctgct catctatgat acgtaccgcc tggctgacgg tgtgccaagc       180
cgtttcagtg gcagtggcag cggtactgac tttacccctca caatttcgtc tctccagccg      240
gaagatttcg ccacttacta ttgtcagcaa tattacaagt tccctttcac cttcggtcag       300
ggcactaaag tagaaatcaa a                                                 321

<210> SEQ ID NO 17
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gatatccaga tgacccagag tccaagcagt ctctccgcca gcgtaggcga tcgtgtgact        60
attacctgtc gtgccagtga ggacctctat tacaacctgg cctggtatca gcgtaaaccg       120
ggcaaagccc cgaagctgct catctatgat acgtaccgcc tggctgacgg tgtgccaagc       180
cgtttcagtg gcagtggcag cggtactgac tataccctca caatttcgtc tctccagccg      240
gaagatttcg cctcttacta ttgtcagcaa tattacaagt tccctttcac cttcggtcag       300

```
ggcactaaag tagaaatcaa a                                            321
```

<210> SEQ ID NO 18
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgaaaaaga cagctatcgc aattgcagtg gccttggctg gtttcgctac cgtagcgcaa    60
gctgatatcc agatgaccca gagtccaagc agtctctccg ccagcgtagg cgatcgtgtg   120
actattacct gtcgtgccag tgaggacctc tattacaacc tggcctggta tcagcgtaaa   180
ccgggcaaag ccccgaagct gctcatctat gatacgtacc gcctggctga cggtgtgcca   240
agccgtttca gtggcagtgg cagcggtact gactataccc tcacaatttc gtctctccag   300
ccggaagatt tcgcctctta ctattgtcag caatattaca agttcccttt caccttcggt   360
cagggcacta agtagaaat caaacgtacg gtagcggccc catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagacta cgagaaacac aaagtctacg cctgcgaagt cacccatcag   660
ggcctgagct caccagtaac aaaaagtttt aatagagggg agtgt               705
```

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
caggtgcagc tgcaggagtc tggaccgggg cttgtcaagc ctagtgagac cctgagcctc    60
acttgtaccg tgagcggctt cagctctacc aattaccatg tgcactggat cgtcagcca   120
cctgggaagg gcctggagtg gattggtgtt atttggggcg acggcgatac atcctacaac   180
tccgtcctga gagccgtgt caccatttcc gttgacacct caaagaatca attttccctc   240
aagttgagct ctgtcaccgc agcggacaca gcagtctatt actgtgcacg tcaactgacc   300
cactattacg ttttggcagc ctggggtcaa gggactctgg tcacagtctc g           351
```

<210> SEQ ID NO 20
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
gaggtgcagc tggtcgagtc tggaggcggg cttgtccagc ctggtgggag cctgcgtctc    60
tcttgtgcag cgagcggctt cagctctacc aattaccatg tgcactgggt gcgtcaggca   120
cctgggaagg gcctggagtg ggtgagtgtt atttggggcg acggcgatac atcctacaac   180
tccgtcctga gagccgtttt caccatttcc cgtgacaact caaagaatac cctttacctc   240
```

```
cagatgaact ctctccgcgc agaggacaca gcagtctatt actgtgcacg tcaactgacc    300
cactattacg ttttggcagc ctggggtcaa gggactctgg tcacagtctc g             351

<210> SEQ ID NO 21
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtgcagc tgcaggagtc tggaccgggg cttgtcaagc ctagtgagac cctgagcctc    60
acttgtaccg tgagcggctt cagctctacc aattaccatg tgcactggat tcgtcagcca    120
cctgggaagg gcctggagtg gatgggtgtt atttggggcg acggcgatac atcctacaac    180
tccgtcctga agagccgtgt caccatttcc cgtgacacct caaagaatca gtttccctc     240 aagttgagct ctgtcaccgc agcggacaca gcagtctatt actgtgcacg tcaactgacc    300
cactattacg ttttggcagc ctggggtcaa gggactctgg tcacagtctc g             351

<210> SEQ ID NO 22
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gaggtgcagc tggtcgagtc tggaggcggg cttgtccagc ctggtgggag cctgcgtctc    60
tcttgtgcag tgagcggctt cagctctacc aattaccatg tgcactgggt gcgtcaggca    120
cctgggaagg gcctggagtg gatgggtgtt atttggggcg acggcgatac atcctacaac    180
tccgtcctga agagccgttt caccatttcc cgtgacacct caaagaatac cgtttacctc    240
cagatgaact ctctccgcgc agaggacaca gcagtctatt actgtgcacg tcaactgacc    300
cactattacg ttttggcagc ctggggtcaa gggactctgg tcacagtctc g             351

<210> SEQ ID NO 23
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gaggttcagc tggtcgagtc tggaggcggg cttgtccagc ctggtgggag cctgcgtctc    60
tcttgtgcag tgagcggctt cagctctacc aattaccatg tgcactgggt gcgtcaggca    120
cctgggaagg gcctggagtg gatgggtgtt atttggggcg acggcgatac atcctacaac    180
tccgtcctga agagccgttt caccatttcc cgtgacacct caaagaatac cgtttacctc    240
cagatgaact ctctccgcgc agaggacaca gcagtctatt actgtgcacg tcaactgacc    300
cactattacg ttttggcagc ctggggtcaa gggactctgg tcacagtctc gagcgcttct    360
acaaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
```

```
tactccctca gcagcgtggt gaccgtgccc tccagcagct gggcaccca gacctacatc    600 tgcaacgtga atcacaagcc cagcaacacc aaggtcgaca agaaagttga gcccaaatct    660
tgt                                                                  663
```

<210> SEQ ID NO 24
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gaggttcagc tggtcgagtc tggaggcggg cttgtccagc ctggtgggag cctgcgtctc     60
tcttgtgcag tgagcggctt cagctctacc aattaccatg tgcactgggt gcgtcaggca    120
cctgggaagg gcctggagtg gatgggtgtt atttggggcg acggcgatac atcctacaac    180
tccgtcctga gagccgtttt caccattttc cgtgacacct caaagaatac cgtttacctc    240
cagatgaact ctctccgcgc agaggacaca gcagtctatt actgtgcacg tcaactgacc    300
cactattacg ttttggcagc ctggggtcaa gggactctgg tcacagtctc gagcgcttct    360
acaaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca  gacctacatc    600 tgcaacgtga atcacaagcc cagcaacacc aaggtcgaca agaaagttga gcccaaatct    660
tgtgacaaaa ctcacacatg cgccgcg                                        687
```

<210> SEQ ID NO 25
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
atgaaaaaga cagctatcgc aattgcagtg gccttggctg gtttcgctac cgtagcgcaa     60
gctgatatcc agatgaccca gagtccaagc agtctctccg ccagcgtagg cgatcgtgtg    120
actattacct gtcgtgccag tgaggacctc tattacaacc tggcctggta tcagcgtaaa    180
ccgggcaaag ccccgaagct gctcatctat gatacgtacc gcctggctga cggtgtgcca    240
agccgtttca gtggcagtgg cagcggtact gactatacccc tcacaatttc gtctctccag    300
ccggaagatt tcgcctctta ctattgtcag caatattaca gttcccttt caccttcggt    360 cagggcacta aagtagaaat caaa                                           384
```

<210> SEQ ID NO 26
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atgaagaaga ctgctatagc aattgcagtg gcgctagctg gtttcgccac cgtggcgcaa     60
```

```
gctgaggttc agctggtcga gtctggaggc gggcttgtcc agcctggtgg gagcctgcgt      120
ctctcttgtg cagtgagcgg cttcagctct accaattacc atgtgcactg ggtgcgtcag      180
gcacctggga agggcctgga gtggatgggt gttatttggg gcgacggcga tacatcctac      240
aactccgtcc tgaagagccg tttcaccatt tcccgtgaca cctcaaagaa taccgtttac      300
ctccagatga actctctccg cgcagaggac acagcagtct attactgtgc acgtcaactg      360
acccactatt acgttttggc agcctggggt caagggactc tggtcacagt ctcgagcgct      420
tctacaaagg gcccatcggt cttccccctg gcacctcct ccaagagcac ctctgggggc       480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtcg acaagaaagt tgagcccaaa     720
tcttgt                                                                 726

<210> SEQ ID NO 27
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgaagaaga ctgctatagc aattgcagtg gcgctagctg gtttcgccac cgtggcgcaa       60
gctgaggttc agctggtcga gtctggaggc gggcttgtcc agcctggtgg gagcctgcgt      120
ctctcttgtg cagtgagcgg cttcagctct accaattacc atgtgcactg ggtgcgtcag      180
gcacctggga agggcctgga gtggatgggt gttatttggg gcgacggcga tacatcctac      240
aactccgtcc tgaagagccg tttcaccatt tcccgtgaca cctcaaagaa taccgtttac      300
ctccagatga actctctccg cgcagaggac acagcagtct attactgtgc acgtcaactg      360
acccactatt acgttttggc agcctggggt caagggactc tggtcacagt ctcgagcgct      420
tctacaaagg gcccatcggt cttccccctg gcacctcct ccaagagcac ctctgggggc       480
acagcggccc tgggctgcct ggtcaaggac tacttccccg aaccggtgac ggtgtcgtgg      540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtcg acaagaaagt tgagcccaaa     720
tcttgtgaca aaactcacac atgcgccgcg                                       750

<210> SEQ ID NO 28
<211> LENGTH: 1438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
atgaaaaaga cagctatcgc aattgcagtg gccttggctg tttcgctac cgtagcgcaa        60 gctgatatcc agatgaccca gagtccaagc agtctctccg ccagcgtagg cgatcgtgtg      120
actattacct gtcgtgccag tgaggacctc tattacaacc tggcctggta tcagcgtaaa      180
```

```
ccgggcaaag ccccgaagct gctcatctat gatacgtacc gcctggctga cggtgtgcca    240
agccgtttca gtggcagtgg cagcggtact gactataccc tcacaatttc gtctctccag    300
ccggaagatt tcgcctctta ctattgtcag caatattaca agttcccttt caccttcggt    360
cagggcacta aagtagaaat caaacgtacg gtagcggccc catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct caccagtaac aaaaagtttt aatagagggg agtgttaaaa tgaagaagac    720
tgctatagca attgcagtgg cgctagctgg tttcgccacc gtggcgcaag ctgaggttca    780
gctggtcgag tctggaggcg gccttgtcca gcctggtggg agcctgcgtc tctcttgtgc    840
agtgagcggc ttcagctcta ccaattacca tgtgcactgg gtgcgtcagg cacctgggaa    900 gggcctgag tggatgggtg ttatttgggg cgacggcgat acatcctaca actccgtcct    960
gaagagccgt ttcaccattt cccgtgacac ctcaaagaat accgtttacc tccagatgaa   1020
ctctctccgc gcagaggaca cagcagtcta ttactgtgca cgtcaactga cccactatta   1080
cgttttggca gcctggggtc aagggactct ggtcacagtc tcgagcgctt ctacaaaggg   1140
cccatcggtc ttccccctgg caccctcctc caagagcacc tctgggggca gcggccct   1200 gggctgcctg gtcaaggact acttccccga accggtgacg gtgtcgtgga actcaggcgc   1260
cctgaccagc ggcgtgcaca ccttcccggc tgtcctacag tcctcaggac tctactccct   1320
cagcagcgtg gtgaccgtgc cctccagcag cttgggcacc cagacctaca tctgcaacgt   1380
gaatcacaag cccagcaaca ccaaggtcga caagaaagtt gagcccaaat cttgttaa     1438
```

<210> SEQ ID NO 29
<211> LENGTH: 117
<212> TYPE: PRT
<213> ORGANISM: Rattus sp.

<400> SEQUENCE: 29

Gln Val Gln Leu Lys Glu Ser Gly Pro Gly Leu Val Gln Pro Ser Glu
1               5                   10                  15

Thr Leu Ser Leu Thr Cys Thr Val Ser Gly Phe Ser Ser Thr Asn Tyr
            20                  25                  30

His Val His Trp Val Arg Gln Pro Pro Gly Lys Ser Leu Glu Trp Met
        35                  40                  45

Gly Val Ile Trp Gly Asp Gly Asp Thr Ser Tyr Asn Ser Val Leu Lys
    50                  55                  60

Ser Arg Leu Ser Ile Thr Arg Asp Thr Ser Arg Ser Gln Val Phe Leu
65                  70                  75                  80

Lys Met Ser Ser Leu Gln Thr Glu Asp Thr Ala Thr Tyr Tyr Cys Ala
                85                  90                  95

Arg Gln Leu Thr His Tyr Tyr Val Leu Ala Ala Trp Gly Gln Gly Ala
            100                 105                 110

Ser Val Thr Val Ser
        115

<210> SEQ ID NO 30
<211> LENGTH: 107
<212> TYPE: PRT
<213> ORGANISM: Rattus sp.

<400> SEQUENCE: 30

Asp Ile Gln Met Thr Gln Ser Pro Ala Ser Leu Ser Ala Ser Leu Gly
1               5                   10                  15

Glu Thr Val Thr Val Glu Cys Arg Ala Ser Glu Asp Leu Tyr Tyr Asn
            20                  25                  30

Leu Ala Trp Tyr Gln Arg Lys Pro Gly Asn Ser Pro Gln Leu Leu Ile
        35                  40                  45

Tyr Asp Thr Tyr Arg Leu Ala Asp Gly Val Pro Ser Arg Phe Ser Gly
    50                  55                  60

Ser Gly Ser Gly Thr Gln Tyr Ser Leu Lys Ile Asn Thr Leu Pro Ser
65              70                  75                  80

Gly Asp Val Ala Ser Tyr Phe Cys Gln Gln Tyr Tyr Lys Phe Pro Phe
            85                  90                  95

Thr Phe Gly Ser Gly Thr Lys Leu Glu Leu Lys
            100                 105

<210> SEQ ID NO 31
<211> LENGTH: 321
<212> TYPE: DNA
<213> ORGANISM: Rattus sp.

<400> SEQUENCE: 31
gacatccaga tgacacagtc tccagcttcc ctgtctgcat ctctgggaga aactgtcacc      60
gtcgaatgtc gagcaagtga ggacctttac tataatttag cgtggtatca gcggaaacca     120
gggaactctc ctcaactcct gatctatgat acatataggt tggcagatgg ggtcccatca     180
cggttcagtg gcagtgggtc tggcacacag tattctctaa agataaacac cctgccatct     240
ggagatgtcg caagttattt ctgtcaacag tattacaaat tccattcac gttcggctca      300 gggaccaagc tggaactgaa a                                                321

<210> SEQ ID NO 32
<211> LENGTH: 351
<212> TYPE: DNA
<213> ORGANISM: Rattus sp.

<400> SEQUENCE: 32
caggtgcagc tgaaggagtc aggacctggc ctggtgcagc cctcagagac cctgtctctc      60
acctgcactg tctctgggtt ctcatcaacc aattatcatg tgcactgggt tcgacagcct     120
ccaggaaaaa gtcttgagtg gatgggagta atatggggtg atggagacac atcatataat     180
tcagttctca aatcccgact gagcatcacc agggacacct ccaggagcca agttttctta     240
aaaatgagca gtctgcaaac ggaggacact gccacctact attgtgccag gcaattgact     300
cattactatg ttctggctgc ctggggtcaa ggagcttcag tcactgtctc g               351

<210> SEQ ID NO 33
<211> LENGTH: 381
<212> TYPE: DNA
<213> ORGANISM: Rattus sp.

<400> SEQUENCE: 33
atgggtgtgc ccactcatct cctgggggttg ttgctactgt ggattacaga tgccatatgt     60
gacatccaga tgacacagtc tccagcttcc ctgtctgcat ctctgggaga aactgtcacc     120
gtcgaatgtc gagcaagtga ggacctttac tataatttag cgtggtatca gcggaaacca    180
gggaactctc ctcaactcct gatctatgat acatataggt tggcagatgg ggtcccatca    240

```
cggttcagtg gcagtgggtc tggcacacag tattctctaa agataaacac cctgccatct    300
ggagatgtcg caagttattt ctgtcaacag tattacaaat ttccattcac gttcggctca    360
gggaccaagc tggaactgaa a                                              381
```

<210> SEQ ID NO 34
<211> LENGTH: 408
<212> TYPE: DNA
<213> ORGANISM: Rattus sp.

<400> SEQUENCE: 34

```
atggctgtcc tggtgctgtt gctctgcctg atgacatttc caagctgtgt cctgtcccag     60
gtgcagctga aggagtcagg acctggcctg gtgcagccct cagagaccct gtctctcacc    120
tgcactgtct ctgggttctc atcaaccaat tatcatgtgc actgggttcg acagcctcca    180
ggaaaaagtc ttgagtggat gggagtaata tggggtgatg agacacatc atataattca    240 gttctcaaat cccgactgag catcaccagg gacacctcca ggagccaagt tttcttaaaa    300
atgagcagtc tgcaaacgga ggacactgcc acctactatt gtgccaggca attgactcat    360
tactatgttc tggctgcctg gggtcaagga gcttcagtca ctgtctcg                 408
```

<210> SEQ ID NO 35
<211> LENGTH: 107
<212> TYPE: PRT
<213> ORGANISM: Homo sapiens

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105
```

<210> SEQ ID NO 36
<211> LENGTH: 321
<212> TYPE: DNA
<213> ORGANISM: Homo sapiens

<400> SEQUENCE: 36

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccttggac gttcggccaa    300 gggaccaagg tggaaatcaa a                                              321
```

-continued

```
<210> SEQ ID NO 37
<211> LENGTH: 111
<212> TYPE: PRT
<213> ORGANISM: Homo sapiens

<400> SEQUENCE: 37
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Phe Asp Tyr Trp Gly Gln Gly Thr Leu Val Thr Val Ser
            100                 105                 110

```
<210> SEQ ID NO 38
<211> LENGTH: 333
<212> TYPE: DNA
<213> ORGANISM: Homo sapiens
<400> SEQUENCE: 38
gaggtgcagc tggtggagtc tgggggaggc ttggtccagc ctggggggtc cctgagactc      60
tcctgtgcag cctctggatt caccgtcagt agcaactaca tgagctgggt ccgccaggct     120
ccagggaagg gctggagtg gtctcagtt atttatagcg gtggtagcac atactacgca     180
gactccgtga aggcagatt caccatctcc agagacaatt ccaagaacac gctgtatctt     240
caaatgaaca gcctgagagc cgaggacacg gctgtgtatt actgtgcgag atactttgac     300
tactggggcc agggaaccct ggtcaccgtc tcc                                  333

<210> SEQ ID NO 39
<211> LENGTH: 111
<212> TYPE: PRT
<213> ORGANISM: Homo sapiens

<400> SEQUENCE: 39
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Phe Asp Tyr Trp Gly Gln Gly Thr Leu Val Thr Val Ser
            100                 105                 110

```
<210> SEQ ID NO 40
```

<211> LENGTH: 333
<212> TYPE: DNA
<213> ORGANISM: Homo sapiens

<400> SEQUENCE: 40

| | | |
|---|---|---|
| caggtgcagc tgcaggagtc gggcccagga ctggtgaagc cttcggagac cctgtccctc | 60 |
| acctgcactg tctctggtgg ctccatcagt agttactact ggagctggat ccggcagccc | 120 |
| ccagggaagg gactggagtg gattgggtat atctattaca gtgggagcac caactacaac | 180 |
| ccctccctca agagtcgagt caccatatca gtagacacgt ccaagaacca gttctccctg | 240 |
| aagctgagct ctgtgaccgc tgcggacacg gccgtgtatt actgtgcgag atactttgac | 300 |
| tactggggcc agggaaccct ggtcaccgtc tcc | 333 |

<210> SEQ ID NO 41
<211> LENGTH: 1459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

| | | |
|---|---|---|
| atgaaaaaga cagctatcgc aattgcagtg gccttggctg gtttcgctac cgtagcgcaa | 60 |
| gctgatatcc agatgaccca gagtccaagc agtctctccg ccagcgtagg cgatcgtgtg | 120 |
| actattacct gtcgtgccag tgaggacctc tattacaacc tggcctggta tcagcgtaaa | 180 |
| ccgggcaaag ccccgaagct gctcatctat gatacgtacc gcctggctga cggtgtgcca | 240 |
| agccgtttca gtggcagtgg cagcggtact gactataccc tcacaatttc gtctctccag | 300 |
| ccggaagatt tcgcctctta ctattgtcag caatattaca agttcccttt caccttcggt | 360 |
| cagggcacta agtagaaat caaacgtacg gtagcggccc catctgtctt catcttcccg | 420 |
| ccatctgatg agcagttgaa atctggaact gcctctgttg tgtgcctgct gaataacttc | 480 |
| tatcccagag aggccaaagt acagtggaag gtggataacg ccctccaatc gggtaactcc | 540 |
| caggagagtg tcacagagca ggacagcaag gacagcacct acagcctcag cagcaccctg | 600 |
| acgctgagca agcagactac gagaaacac aaagtctacg cctgcgaagt cacccatcag | 660 |
| ggcctgagct caccagtaac aaaaagtttt aatagagggg agtgttaaaa tgaagaagac | 720 |
| tgctatagca attgcagtgg cgctagctgg tttcgccacc gtggcgcaag ctgaggttca | 780 |
| gctggtcgag tctggaggcg ggcttgtcca gcctggtggg agcctgcgtc tctcttgtgc | 840 |
| agtgagcggc ttcagctcta ccaattacca tgtgcactgg gtgcgtcagg cacctgggaa | 900 |
| gggcctggag tggatgggtg ttatttgggg cgacggcgat acatcctaca actccgtcct | 960 |
| gaagagccgt ttcaccattt cccgtgacac ctcaaagaat accgtttacc tccagatgaa | 1020 |
| ctctctccgc gcagaggaca cagcagtcta ttactgtgca cgtcaactga cccactatta | 1080 |
| cgttttggca gcctggggtc aagggactct ggtcacagtc tcgagcgctt ctacaaaggg | 1140 |
| cccatcggtc ttccccctgg caccctcctc aagagcacc tctggggca gcggccct | 1200 |
| gggctgcctg gtcaaggact acttccccga accggtgacg gtgtcgtgga actcaggcgc | 1260 |
| cctgaccagc ggcgtgcaca ccttcccggc tgtcctacag tcctcaggac tctactccct | 1320 |
| cagcagcgtg gtgaccgtgc cctccagcag cttgggcacc cagacctaca tctgcaacgt | 1380 |
| gaatcacaag cccagcaaca ccaaggtcga caagaaagtt gagcccaaat cttgtgacaa | 1440 |
| aactcacaca tgcgccgcg | 1459 |

```
<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Phe Thr Phe Ser Asp Tyr Tyr Met Ala
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ile Ser Tyr Glu Gly Ser Ser Thr Tyr Tyr Gly Asp Ser Val Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Asp Asp Ser Pro Gly Tyr Tyr Phe Asp Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Ala Gly Glu Asp Ile Ser Asn Val Leu Ala
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Asn Arg Leu Gln Asp
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 47

Gln Gln Thr Phe Arg Tyr Pro Leu Thr
1               5

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Phe Ser Leu Thr Ser His His Ile Ser
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Met Trp Asn Asp Gly Gly Thr Leu Tyr Asn Ser Ala Leu Lys Ser
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Lys Met His Tyr Tyr Val Leu Asp Ala
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Thr Ser Glu Asp Ile Tyr Ser Asn Leu Ala
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Thr Asn Arg Leu Ala Asp
1               5

<210> SEQ ID NO 53

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln His Tyr Ser Asn Phe Pro Trp Thr
1               5

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Thr Ser Leu Ser Ala Ser Leu Gly
1               5                   10                  15

Glu Thr Val Ser Ile Glu Cys Leu Ala Gly Glu Asp Ile Ser Asn Val
            20                  25                  30

Leu Ala Trp Tyr Gln Gln Lys Ser Gly Gly Ser Pro Gln Leu Leu Ile
        35                  40                  45

Tyr Ala Ala Asn Arg Leu Gln Asp Gly Val Pro Ser Arg Phe Ser Gly
    50                  55                  60

Ser Gly Ser Gly Thr Arg Tyr Ser Leu Lys Ile Ser Gly Met Arg Pro
65                  70                  75                  80

Glu Asp Glu Ala Asp Tyr Phe Cys Gln Gln Thr Phe Arg Tyr Pro Leu
                85                  90                  95

Thr Phe Gly Ser Gly Thr Lys Leu Glu Leu Lys
            100                 105

<210> SEQ ID NO 55
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gacatccaga tgacacagtc tccaacttcc ctgtctgcat ctctcggaga aactgtctcc      60
atcgaatgtc tagcaggtga agacatttcc aatgttttag cgtggtatca gcagaagtca    120 gggggggtctc ctcagctcct gatctatgct gcaaataggt tacaagacgg ggtcccctca   180
cggttcagtg gcagtggatc tggcacacgg tattctctca agatcagtgg catgcgacct    240
gaagatgaag cagattattt ctgtcaacag actttcaggt atccgctcac gttcggttct    300
gggaccaagc tggaattgaa a                                              321

<210> SEQ ID NO 56
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Pro Leu Val Glu Ser Gly Gly Gly Leu Val Gln Pro Gly Arg
```

```
 1               5                   10                  15
Ser Met Lys Leu Ser Cys Val Ala Ser Gly Phe Thr Phe Ser Asp Tyr
                20                  25                  30

Tyr Met Ala Trp Val Arg Gln Ala Pro Lys Lys Gly Leu Glu Trp Val
                35                  40                  45

Ala Ser Ile Ser Tyr Glu Gly Ser Ser Thr Tyr Tyr Gly Asp Ser Val
                50                  55                  60

Lys Gly Arg Phe Thr Val Ser Arg Asp Ile Ala Lys Ser Thr Leu Tyr
65                  70                  75                  80

Leu Gln Met His Ser Leu Lys Ser Glu Asp Thr Ala Ile Tyr Tyr Cys
                85                  90                  95

Ala Arg His Asp Asp Ser Pro Gly Tyr Tyr Phe Asp Tyr Trp Gly Gln
                100                 105                 110

Gly Val Met Val Thr Val Ser
        115
```

<210> SEQ ID NO 57
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gaggtgccgc tggtggagtc tgggggaggc ttagtgcagc ctggaaggtc catgaaactt      60
tcctgtgtag cctcaggatt cactttcagt gactattaca tggcctgggt ccgccaggct     120
ccaaagaagg gtctggagtg gtcgcatcc attagttatg agggtagtag tacttactat      180
ggagactccg tgaagggccg attcactgtc tccagagata ttgcaaaaag caccctatac     240
cttcaaatgc acagtctgaa gtctgaggat acggccattt attattgtgc acgacatgac     300
gatagtccag atactacttt tgattattgg ggccaaggag tcatggtcac agtctcg       357
```

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Asp Ile Gln Met Thr Gln Ser Pro Ala Ser Leu Ser Ala Ser Leu Gly
1               5                   10                  15

Glu Thr Val Thr Ile Glu Cys Arg Thr Ser Glu Asp Ile Tyr Ser Asn
                20                  25                  30

Leu Ala Trp Tyr Arg Gln Arg Pro Gly Lys Ser Pro Gln Leu Leu Ile
                35                  40                  45

Tyr Asp Thr Asn Arg Leu Ala Asp Gly Val Pro Ser Arg Phe Ser Gly
                50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln His Tyr Ser Asn Phe Pro Trp
                85                  90                  95

Thr Phe Gly Gly Asp Thr Lys Leu Glu Leu Lys
                100                 105
```

```
<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gacatccaga tgacacagtc tccggcttcc ctgtctgcat ctctgggaga aactgtcacc      60
atcgaatgtc gaacaagtga ggacatttac agtaatttag cgtggtatcg gcagagacca    120
gggaagtctc ctcagctcct gatctatgat acaaatagat ggctgatgg ggtcccgtca     180 cggttcagtg gcagtggatc tggcacacaa tattctctaa agataaacag cctgcaatct    240
gaagatgtcg ccagctattt ctgtcaacac tatagcaatt ttccgtggac cttcggtgga    300
gacaccaagc tggaattgaa a                                              321

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Thr Glu Ser Gly Pro Gly Leu Val Gln Pro Ser Gln
1               5                  10                   15

Thr Leu Ser Leu Thr Cys Thr Val Ser Gly Phe Ser Leu Thr Ser His
            20                  25                  30

His Ile Ser Trp Val Arg Gln Pro Pro Gly Lys Gly Leu Glu Trp Val
        35                  40                  45

Gly Val Met Trp Asn Asp Gly Gly Thr Leu Tyr Asn Ser Ala Leu Lys
    50                  55                  60

Ser Arg Pro Ser Ile Ser Arg Asp Thr Ser Lys Ser Gln Val Phe Leu
65                  70                  75                  80

Lys Met Ser Ser Leu Gln Thr Glu Asp Thr Ala Thr Tyr Tyr Cys Ala
                85                  90                  95

Arg Gly Lys Met His Tyr Tyr Val Leu Asp Ala Trp Gly Gln Gly Ala
            100                 105                 110

Ser Val Thr Val Ser
        115

<210> SEQ ID NO 61
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caggtgcagc tgacggagtc agggcctggc ctggtgcagc cctcacagac cctgtctctc      60
acctgcactg tctctgggtt ctcattaacc agccatcata tatcctgggt tcgacagcct    120
ccaggaaaag gtctggagtg gtgggagtc atgtggaatg atggaggcac attatataat     180
tcagctctca agtctcgacc gagcatcagt aggacacct ccaagagtca ggtcttctta     240
aaaatgagca gtctgcaaac tgaagacaca gccacttact actgtgccag ggcaaaatg     300 cattactatg ttctggatgc ctggggtcaa ggagcttcag tcactgtctc g             351
```

<210> SEQ ID NO 62
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Thr Leu Ser
            20                  25                  30

Val Ser Pro Gly Glu Arg Ala Thr Ile Ser Cys Arg Ala Ser Gln Arg
        35                  40                  45

Val Ser Ser Ser Thr Tyr Ser Tyr Met His Trp Tyr Gln Gln Lys Pro
    50                  55                  60

Gly Gln Pro Pro Lys Leu Leu Ile Lys Tyr Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Thr Ile Ser Ser Val Glu Pro Glu Asp Phe Ala Thr Tyr Tyr Cys
            100                 105                 110

Gln His Ser Trp Glu Ile Pro Pro Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 63
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
            85                  90                  95

Glu Ile Pro Pro Thr Phe Gly Gly Gly Thr Lys Leu Glu Ile Lys Arg
        100                 105                 110

Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 717
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggagacag acacactcct gttatgggtg ctgctgctct gggttccagg ttccactggt      60
gacattgtac tgacacagtc tcctgctacc ttatctgtat ctccgggaga gagggccacc     120
atctcatgca gggccagcca acgtgtcagt tcatctacct atagttatat gcactggtac     180
caacagaaac aggacagcc acccaaactc ctcatcaagt atgcatccaa cctagaatct     240
ggggtccctg ccaggttcag tggcagtggg tctgggactg acttcaccct caccatctct     300
tctgtggagc cggaggattt tgcaacatat tactgtcagc acagttggga gattcctccg     360
acgttcggtg agggaccaa gctggagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag acagcaagg acagcaccta cagcctcagc     600
agcaccctga cgctgagcaa agcagactac gagaacaca aagtctacgc ctgcgaagtc     660
acccatcagg gcctgagctc gcccgtcaca aagagcttca caggggaga gtgttag        717

<210> SEQ ID NO 65
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Asp Trp Thr Trp Arg Val Phe Cys Leu Leu Ala Val Ala Pro Gly
1               5                   10                  15

```
Ala His Ser Gln Val Gln Leu Val Gln Ser Gly Ala Glu Val Val Lys
            20                  25                  30
Pro Gly Ala Ser Val Lys Leu Ser Cys Lys Ala Ser Gly Tyr Ile Phe
        35                  40                  45
Thr Ser Tyr Tyr Met Tyr Trp Val Lys Gln Ala Pro Gly Gln Gly Leu
    50                  55                  60
Glu Trp Ile Gly Glu Ile Asn Pro Ser Asn Gly Asp Thr Asn Phe Asn
65                  70                  75                  80
Glu Lys Phe Lys Ser Lys Ala Thr Leu Thr Val Asp Lys Ser Ala Ser
                85                  90                  95
Thr Ala Tyr Met Glu Leu Ser Ser Leu Arg Ser Glu Asp Thr Ala Val
            100                 105                 110
Tyr Tyr Cys Thr Arg Ser Asp Gly Arg Asn Asp Met Asp Ser Trp Gly
        115                 120                 125
Gln Gly Thr Leu Val Thr Val Ser Ser Ala Ser Thr Lys Gly Pro Ser
    130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
            180                 185                 190
Val Leu Gln Ser Ser Gly Leu Tyr Ser Leu Ser Ser Val Val Thr Val
        195                 200                 205
Pro Ser Ser Ser Leu Gly Thr Lys Thr Tyr Thr Cys Asn Val Asp His
    210                 215                 220
Lys Pro Ser Asn Thr Lys Val Asp Lys Arg Val Glu Ser Lys Tyr Gly
225                 230                 235                 240
Pro Pro Cys Pro Pro Cys Pro Ala Pro Glu Phe Leu Gly Gly Pro Ser
                245                 250                 255
Val Phe Leu Phe Pro Pro Lys Pro Lys Asp Thr Leu Met Ile Ser Arg
            260                 265                 270
Thr Pro Glu Val Thr Cys Val Val Val Asp Val Ser Gln Glu Asp Pro
        275                 280                 285
Glu Val Gln Phe Asn Trp Tyr Val Asp Gly Val Glu Val His Asn Ala
    290                 295                 300
Lys Thr Lys Pro Arg Glu Glu Gln Phe Asn Ser Ala Tyr Arg Val Val
305                 310                 315                 320
Ser Val Leu Thr Val Leu His Gln Asp Trp Leu Asn Gly Lys Glu Tyr
                325                 330                 335
Lys Cys Lys Val Ser Asn Lys Gly Leu Pro Ser Ser Ile Glu Lys Thr
            340                 345                 350
Ile Ser Lys Ala Lys Gly Gln Pro Arg Glu Pro Gln Val Tyr Thr Leu
        355                 360                 365
Pro Pro Ser Gln Glu Glu Met Thr Lys Asn Gln Val Ser Leu Thr Cys
    370                 375                 380
Leu Val Lys Gly Phe Tyr Pro Ser Asp Ile Ala Val Glu Trp Glu Ser
385                 390                 395                 400
Asn Gly Gln Pro Glu Asn Asn Tyr Lys Thr Thr Pro Pro Val Leu Asp
                405                 410                 415
Ser Asp Gly Ser Phe Phe Leu Tyr Ser Arg Leu Thr Val Asp Lys Ser
            420                 425                 430
```

-continued

Arg Trp Gln Glu Gly Asn Val Phe Ser Cys Ser Val Met His Glu Ala
435 440 445

Leu His Asn His Tyr Thr Gln Lys Ser Leu Ser Leu Ser Leu Gly
450 455 460

<210> SEQ ID NO 66
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
                20                  25                  30

Tyr Met Tyr Trp Val Lys Gln Ala Pro Gly Gln Gly Leu Glu Trp Ile
            35                  40                  45

Gly Glu Ile Asn Pro Ser Asn Gly Asp Thr Asn Phe Asn Glu Lys Phe
        50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Ala Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 67
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atggactgga cctggagggt cttctgcttg ctggctgtag caccaggtgc ccactcccag      60
gtccaactgg tgcagtcagg ggctgaagtg gtgaagcctg gggcttcagt gaagttgtcc    120
tgcaaggctt ctggctacat cttcaccagt tattatatgt actgggtgaa gcaggcgccc    180
ggacaaggcc ttgagtggat tggagagatt aatcctagca atggtgatac taacttcaat    240
gagaagttca agagtaaggc cacactgact gtagacaaat ccgccagcac agcatacatg    300
gagctcagca gcctgaggtc tgaggacact gcggtctatt actgtacaag atcggacggt    360
agaaatgata tggactcctg gggccaaggg accctggtca ccgtctcctc agcttccacc    420
aagggcccat ccgtcttccc cctggcgccc tgctccagat ctacctccga gagcacagcc    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacgaagac ctacacctgc    660
aacgtagatc acaagcccag caacaccaag gtggacaaga gagttgagtc caaatatggt    720
cccccatgcc caccgtgccc agcacctgag ttcctggggg gaccatcagt cttcctgttc    780
cccccaaaac ccaaggacac tctcatgatc tcccggaccc ctgaggtcac gtgcgtggtg    840
gtggacgtga gccaggaaga cccgaggtc cagttcaact ggtacgtgga tggcgtggag    900
gtgcataatg ccaagacaaa gccgcgggag gagcagttca acagcgcgta ccgtgtggtc    960
agcgtcctca ccgtcctgca ccaggactgg ctgaacggca aggagtacaa gtgcaaggtc   1020
tccaacaaag gcctcccgtc ctccatcgag aaaaccatct ccaaagccaa agggcagccc   1080
cgagagccac aagtgtacac cctgccccca tcccaggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acgcctcccg tcctcgattc cgacggctcc   1260
ttcttcctct acagcaggct aaccgtggac aagagcaggt ggcaggaggg gaatgtcttc   1320
tcatgctccg tgatgcatga ggctctgcac aaccactaca cacagaagag cctctcccta   1380
tctctgggtt ga                                                              1392

<210> SEQ ID NO 68
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Glu Asp Leu Tyr Tyr Asn Leu Ala Trp Tyr Gln Arg Lys Pro Gly Lys
    50                  55                  60

Ala Pro Lys Leu Leu Ile Tyr Asp Thr Tyr Arg Leu Ala Asp Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Ser Tyr Tyr Cys Gln Gln
            100                 105                 110

Tyr Tyr Lys Phe Pro Phe Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 69
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Leu Tyr Tyr Asn
            20                  25                  30

Leu Ala Trp Tyr Gln Arg Lys Pro Gly Lys Ala Pro Lys Leu Leu Ile
        35                  40                  45

Tyr Asp Thr Tyr Arg Leu Ala Asp Gly Val Pro Ser Arg Phe Ser Gly

```
              50                  55                  60
Ser Gly Ser Gly Thr Asp Tyr Thr Leu Thr Ile Ser Ser Leu Gln Pro
 65                  70                  75                  80

Glu Asp Phe Ala Ser Tyr Tyr Cys Gln Gln Tyr Tyr Lys Phe Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 70
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atggacatga gggtccccgc tcagctcctg gggctcctgc tactctggct ccgaggtgcc      60
agatgtgata tccagatgac ccagagtcca agcagtctct ccgccagcgt aggcgatcgt     120
gtgactatta cctgtcgtgc cagtgaggac ctctattaca acctggcctg gtatcagcgt     180
aaaccgggca agccccgaa gctgctcatc tatgatacgt accgcctggc tgacggtgtg     240
ccaagccgtt tcagtggcag tggcagcggt actgactata ccctcacaat ttcgtctctc     300
cagccggaag atttcgcctc ttactattgt cagcaatatt acaagttccc tttcaccttc     360
ggtcagggca ctaaagtaga aatcaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g              711

<210> SEQ ID NO 71
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Asp Trp Thr Trp Arg Val Phe Cys Leu Leu Ala Val Ala Pro Gly
```

-continued

```
  1               5                  10                 15
Ala His Ser Glu Val Gln Leu Val Glu Ser Gly Gly Gly Leu Val Gln
                 20                 25                 30
Pro Gly Gly Ser Leu Arg Leu Ser Cys Ala Val Ser Gly Phe Ser Ser
                 35                 40                 45
Thr Asn Tyr His Val His Trp Val Arg Gln Ala Pro Gly Lys Gly Leu
                 50                 55                 60
Glu Trp Met Gly Val Ile Trp Gly Asp Gly Asp Thr Ser Tyr Asn Ser
 65                 70                 75                 80
Val Leu Lys Ser Arg Phe Thr Ile Ser Arg Asp Thr Ser Lys Asn Thr
                 85                 90                 95
Val Tyr Leu Gln Met Asn Ser Leu Arg Ala Glu Asp Thr Ala Val Tyr
                100                105                110
Tyr Cys Ala Arg Gln Leu Thr His Tyr Val Leu Ala Ala Trp Gly
                115                120                125
Gln Gly Thr Leu Val Thr Val Ser Ser Ala Ser Thr Lys Gly Pro Ser
                130                135                140
Val Phe Pro Leu Ala Pro Cys Ser Arg Ser Thr Ser Glu Ser Thr Ala
145                150                155                160
Ala Leu Gly Cys Leu Val Lys Asp Tyr Phe Pro Glu Pro Val Thr Val
                165                170                175
Ser Trp Asn Ser Gly Ala Leu Thr Ser Gly Val His Thr Phe Pro Ala
                180                185                190
Val Leu Gln Ser Ser Gly Leu Tyr Ser Leu Ser Ser Val Val Thr Val
                195                200                205
Pro Ser Ser Leu Gly Thr Lys Thr Tyr Thr Cys Asn Val Asp His
                210                215                220
Lys Pro Ser Asn Thr Lys Val Asp Lys Arg Val Glu Ser Lys Tyr Gly
225                230                235                240
Pro Pro Cys Pro Pro Cys Pro Ala Pro Glu Phe Leu Gly Gly Pro Ser
                245                250                255
Val Phe Leu Phe Pro Pro Lys Pro Lys Asp Thr Leu Met Ile Ser Arg
                260                265                270
Thr Pro Glu Val Thr Cys Val Val Val Asp Val Ser Gln Glu Asp Pro
                275                280                285
Glu Val Gln Phe Asn Trp Tyr Val Asp Gly Val Glu Val His Asn Ala
                290                295                300
Lys Thr Lys Pro Arg Glu Glu Gln Phe Asn Ser Ala Tyr Arg Val Val
305                310                315                320
Ser Val Leu Thr Val Leu His Gln Asp Trp Leu Asn Gly Lys Glu Tyr
                325                330                335
Lys Cys Lys Val Ser Asn Lys Gly Leu Pro Ser Ser Ile Glu Lys Thr
                340                345                350
Ile Ser Lys Ala Lys Gly Gln Pro Arg Glu Pro Gln Val Tyr Thr Leu
                355                360                365
Pro Pro Ser Gln Glu Glu Met Thr Lys Asn Gln Val Ser Leu Thr Cys
                370                375                380
Leu Val Lys Gly Phe Tyr Pro Ser Asp Ile Ala Val Glu Trp Glu Ser
385                390                395                400
Asn Gly Gln Pro Glu Asn Asn Tyr Lys Thr Thr Pro Pro Val Leu Asp
                405                410                415
Ser Asp Gly Ser Phe Phe Leu Tyr Ser Arg Leu Thr Val Asp Lys Ser
                420                425                430
```

```
Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly
    450                 455                 460

<210> SEQ ID NO 72
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Ser Thr Asn Tyr
            20                  25                  30

His Val His Trp Val Arg Gln Ala Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Ala Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
```

```
                     325                 330                 335
Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 73
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
atggactgga cctggagggt cttctgcttg ctggctgtag caccaggtgc ccactccgaa      60
gtacaattgg tcgagtctgg aggcgggctt gtccagcctg gtgggagcct gcgtctctct     120
tgtgcagtga gcggcttcag ctctaccaat taccatgtgc actgggtgcg tcaggcacct     180
gggaagggcc tggagtggat gggtgttatt tggggcgacg gcgatacatc ctacaactcc     240
gtcctgaaga gccgtttcac catttcccgt gacacctcaa agaataccgt ttacctccag     300
atgaactctc tccgcgcaga ggacacagca gtctattact gtgcacgtca actgacccac     360
tattacgttt tggcagcctg ggtcaaggg actctggtca cagtctcgag cgcttcaacc     420
aagggcccat ccgtcttccc cctggcgccc tgctccagat ctacctccga gagcacagcc     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacgaagac ctacacctgc     660
aacgtagatc acaagcccag caacaccaag gtggacaaga gagttgagtc caaatatggt     720
cccccatgcc caccgtgccc agcacctgag ttcctggggg gaccatcagt cttcctgttc     780
cccccaaaac ccaaggacac tctcatgatc tcccggaccc ctgaggtcac gtgcgtggtg     840
gtggacgtga gccaggaaga ccccgaggtc cagttcaact ggtacgtgga tggcgtggag     900
gtgcataatg ccaagacaaa gccgcgggag gagcagttca acagcgcgta ccgtgtggtc     960
agcgtcctca ccgtcctgca ccaggactgg ctgaacggca aggagtacaa gtgcaaggtc    1020
tccaacaaag gcctcccgtc ctccatcgag aaaaccatct ccaaagccaa agggcagccc    1080
cgagagccac aagtgtacac cctgccccca tcccaggagg agatgaccaa gaaccaggtc    1140
agcctgacct gcctggtcaa aggcttctac cccagcgaca tcgccgtgga gtgggagagc    1200
aatgggcagc cggagaacaa ctacaagacc acgcctcccg tcctcgattc gacggctcc     1260 ttcttcctct acagcaggct aaccgtggac aagagcaggt ggcaggaggg gaatgtcttc    1320
tcatgctccg tgatgcatga ggctctgcac aaccactaca cacagaagag cctctcccctg   1380
```
tctctgggtt ga                                                    1392

<210> SEQ ID NO 74
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ser Thr Asn Tyr
            20                  25                  30

His Val His Trp Ile Arg Gln Pro Pro Gly Lys Gly Leu Glu Trp Ile
        35                  40                  45

Gly Val Ile Trp Gly Asp Gly Asp Thr Ser Tyr Asn Ser Val Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115

<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ser Thr Asn Tyr
            20                  25                  30

His Val His Trp Ile Arg Gln Pro Pro Gly Lys Gly Leu Glu Trp Met
        35                  40                  45

Gly Val Ile Trp Gly Asp Gly Asp Thr Ser Tyr Asn Ser Val Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Gln Leu Thr His Tyr Tyr Val Leu Ala Ala Trp Gly Gln Gly Thr
            100                 105                 110

Leu Val Thr Val Ser
        115

<210> SEQ ID NO 76
<211> LENGTH: 146
<212> TYPE: PRT
<213> ORGANISM: Homo sapiens

<400> SEQUENCE: 76

Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Gly Leu Tyr Tyr Ile Tyr Ala Gly Val Thr Phe Cys Ser
    50                  55                  60

Asn Arg Glu Ala Ser Ser Gln Ala Pro Phe Ile Ala Ser Leu Cys Leu
65                  70                  75                  80

Lys Ser Pro Gly Arg Phe Glu Arg Ile Leu Leu Arg Ala Ala Asn Thr
                85                  90                  95

His Ser Ala Lys Pro Cys Gly Gln Gln Ser Ile His Leu Gly Gly
            100                 105                 110

Val Phe Glu Leu Gln Pro Gly Ala Ser Val Phe Val Asn Val Thr Asp
        115                 120                 125

Pro Ser Gln Val Ser His Gly Thr Gly Phe Thr Ser Phe Gly Leu Leu
    130                 135                 140

Lys Leu
145

<210> SEQ ID NO 77
<211> LENGTH: 146
<212> TYPE: PRT
<213> ORGANISM: Mus musculus

<400> SEQUENCE: 77

Gly Asp Glu Asp Pro Gln Ile Ala Ala His Val Val Ser Glu Ala Asn
1               5                   10                  15

Ser Asn Ala Ala Ser Val Leu Gln Trp Ala Lys Lys Gly Tyr Tyr Thr
            20                  25                  30

Met Lys Ser Asn Leu Val Met Leu Glu Asn Gly Lys Gln Leu Thr Val
        35                  40                  45

Lys Arg Glu Gly Leu Tyr Tyr Val Tyr Thr Gln Val Thr Phe Cys Ser
    50                  55                  60

Asn Arg Glu Pro Ser Ser Gln Arg Pro Phe Ile Val Gly Leu Trp Leu
65                  70                  75                  80

Lys Pro Ser Ser Gly Ser Glu Arg Ile Leu Leu Lys Ala Ala Asn Thr
                85                  90                  95

His Ser Ser Ser Gln Leu Cys Glu Gln Gln Ser Val His Leu Gly Gly
            100                 105                 110

Val Phe Glu Leu Gln Ala Gly Ala Ser Val Phe Val Asn Val Thr Glu
        115                 120                 125

Ala Ser Gln Val Ile His Arg Val Gly Phe Ser Ser Phe Gly Leu Leu
    130                 135                 140

Lys Leu
145